United States Patent
Repetti et al.

(10) Patent No.: US 8,895,305 B2
(45) Date of Patent: Nov. 25, 2014

(54) WATER DEFICIT-INDUCIBLE PROMOTERS

(75) Inventors: Peter P. Repetti, Emeryville, CA (US); Hans E. Holtan, Emeryville, CA (US); Roderick W. Kumimoto, Norman, OK (US); Oliver J. Ratcliffe, Oakland, CA (US)

(73) Assignee: Mendel Biotechnology, Inc., Hayward, CA (US)

( * ) Notice: Subject to any disclaimer, the term of this patent is extended or adjusted under 35 U.S.C. 154(b) by 1347 days.

(21) Appl. No.: 12/526,042

(22) PCT Filed: Feb. 7, 2008

(86) PCT No.: PCT/US2008/053354
§ 371 (c)(1),
(2), (4) Date: Sep. 13, 2010

(87) PCT Pub. No.: WO2008/098148
PCT Pub. Date: Aug. 14, 2008

(65) Prior Publication Data
US 2011/0010796 A1     Jan. 13, 2011

Related U.S. Application Data

(60) Provisional application No. 60/900,497, filed on Feb. 8, 2007.

(51) Int. Cl.
| | | |
|---|---|---|
| C12N 5/10 | (2006.01) | |
| A01H 5/00 | (2006.01) | |
| C12N 15/63 | (2006.01) | |
| C12N 15/82 | (2006.01) | |
| C12N 15/00 | (2006.01) | |
| C07H 21/04 | (2006.01) | |

(52) U.S. Cl.
CPC ........ C12N 15/8237 (2013.01); C12N 15/8273 (2013.01)
USPC ........... 435/419; 800/298; 800/278; 435/468; 435/320.1; 536/24.1

(58) Field of Classification Search
None
See application file for complete search history.

(56) References Cited

U.S. PATENT DOCUMENTS

| 7,511,130 B2 * | 3/2009 | Heck et al. ............. 536/24.1 |
| 2004/0123347 A1 * | 6/2004 | Hinchey et al. ........ 800/279 |
| 2005/0097631 A1 | 5/2005 | Sun |

FOREIGN PATENT DOCUMENTS

| EP | 1 209 228 | 5/2002 |
| WO | WO 2005/047516 | 5/2005 |
| WO | WO2005/047516 A3 * | 5/2005 |

OTHER PUBLICATIONS

NM_121528. *Arabidopsis thaliana* amino acid transporter family protein (AT5G15240) mRNA, complete cds. (Jan. 29, 2002).
prAT1G16850, found in GenBank acc. NC_003070. *Arabidopsis thaliana* chromosome 1, complete sequence. (Aug. 13, 2001).
prAt5g52300, found in Genbank acc. No. AB019226, GI:3869065. *Arabidopsis thaliana* strain Columbia chromosome 5 clone K24M7 (Nov. 10, 1998).
prAt3g46230, found in Genbank acc. No. AL355775, GI:7798991. *Arabidopsis thaliana* DNA chromosome 3, BAC clone F12M12. (May 10, 2000).
prAT1G52690, found in Genbank acc. AC008016. *Arabidopsis thaliana* chromosome 1, * Sequencing in Progress *, 6 unordered pieces.(Jul. 10, 1999).
prAt2g37870, found in Genbank acc. No. AC007661, GI:6598780. *Arabidopsis thaliana* chromosome II BAC T8P21 genomic sequence, complete sequence.(May 27, 1999).
prAT5G43840 or prG1947, found in Genbank acc. AB026651, GI:4757407. *Arabidopsis thaliana* genomic DNA, chromosome 5, P1 clone: MQD19,complete sequence.(May 6, 1999).
prAt5g66780, found in Genbank acc. No. AB010700, GI:2828185. *Arabidopsis thaliana* genomic DNA, chromosome 5, P1 clone: MUD21,complete sequence. (Feb. 2, 1998).
prAt3g17520, found in Genbank acc. No. AB022219, GI:7321075. *Arabidopsis thaliana* genomic DNA, chromosome 3, P1 clone: MKP6, complete sequence. (Jan. 14, 1999).
prAt4g09600, found in Genbank acc. No. AL161831, GI:7321075. *Arabidopsis thaliana* DNA chromosome 4, BAC clone T25P22 (ESSA project). (Feb. 22, 2000).

* cited by examiner

*Primary Examiner* — Brent T Page
*Assistant Examiner* — Russell Boggs
(74) *Attorney, Agent, or Firm* — Dentons US LLP

(57) ABSTRACT

Water deficit-inducible promoter sequences were identified that may be used to produce transgenic plants that are more tolerant to water deficit and related hyperosmotic stresses than control plants, and yet are wild-type or nearly wild type in appearance. Any of these water deficit-inducible promoters may be incorporated into an expression vector that comprises a polynucleotide regulated by one such promoter and which encodes a polypeptide that, when ectopically expressed, improves water deficit tolerance in plants that are similar to control plants in their morphology and development.

19 Claims, 3 Drawing Sheets

```
                          SEQUENCE LISTING

<160> NUMBER OF SEQ ID NOS: 74

<210> SEQ ID NO 1
<211> LENGTH: 766
<212> TYPE: DNA
<213> ORGANISM: Arabidopsis thaliana
<220> FEATURE:
<223> OTHER INFORMATION: SEQ ID NO: 1  Contains promoter fragment from
      prAT1G16850, found in GenBank acc. NC_003070)

<400> SEQUENCE: 1
attgggtacg attttcatag gtctttcctc acgccagaag tgttgtttta ttttgttgat      60
tgagttatta attattggaa gcttttcttt caagcaaagt aaaatgcgta ataatgatta     120
gtcacatcca atggttagtc agtctattac accgttaatc aagctctggt catataattt     180
ttttattttt ggaactaaca cttattagtt taggtttcca tcacctattt aattcgtaat     240
tcttatacat gcatataata gagatacata tatacaaatt tatgatcatt tttgcacaac     300
atgtgatctc attcattagt atgcattatg cgaaaacctc gacgcgcaaa agacacgtaa     360
tagctaataa tgttactcat ttataatgat tgaagcaaga cgaaaacaac aacatatata     420
tcaaattgta aactagatat ttcttaaaag tgaaaaaaaa caaagaaata taaaggacaa     480
ttttgagtca gtctcttaat attaaaacat atatacataa ataagcacaa acgtggttac     540
ctgtcttcat gcaatgtgga ctttagttta tctaatcaaa atcaaaataa aaggtgtaat     600
agttctcgtc attttttcaaa ttttaaaaat cagaaccaag tgattttgt ttgagtattg     660 atccattgtt taaacaattt aacacagtat atacgtctct tgagatgttg acatgatgat     720
aaaatacgag atcgtctctt ggttttcgaa ttttgaactt taatag                    766

<210> SEQ ID NO 2
<211> LENGTH: 605
<212> TYPE: DNA
<213> ORGANISM: Arabidopsis thaliana
<220> FEATURE:
<223> OTHER INFORMATION: SEQ ID NO: 2  Contains promoter fragment from
      prAt5g52300, found in Genbank acc. no. AB019226, GI:3869065)

<400> SEQUENCE: 2
tgatgatgat gatgaagaag agaacgaatt ttgaaattgg cggttttgaa ttttaagaa       60
```

```
attaaaaaat atccccgtc gatttcaaga gggagatgga gataccaaag caactctcgc    120
cacttgtcgt cttttaattt taattgagta cgttatgccg ttttaaatgt tcaaaacagc    180
acacagttga tagctgaatt gatttttct tttgccgttt tgttatattt aaacaacaca    240
cagtgcattt gccaataac tacatgatgg gccaataaac gtggaccgac taaaactaaa    300
taatagaaga tacatcgata ggcttctcta aagatcggat aaaagataat gtcgcatagc    360
cacgtagaga gcaactggct gagacgtggc aggacgaaac ggacgcatcg tacgtgtcag    420
aatcctacag aagtaaagag acagaagcca gagagaggtg gttcggccat atgtcatcgt    480
tctctctata aactttatgg aactttgttc tgattttctc agacacgga aaagaaagaa    540 aacaacacta gaacaaagag ggtttgattg attcacttga aaagagaaa acacagcttt    600 ggaaa                                                                605

<210> SEQ ID NO 3
<211> LENGTH: 907
<212> TYPE: DNA
<213> ORGANISM: Arabidopsis thaliana
<220> FEATURE:
<223> OTHER INFORMATION: SEQ ID NO: 3  Contains promoter fragment from
      prAt3g46230, found in Genbank acc. no. AL355775, GI:7798991)

<400> SEQUENCE: 3
ttatttattc tcaattttcc catacgaatt ttttgtcttt atatttatca caaaaaaga    60 gtttgctctt taaaaaacta tactaatgta attttttat tttatttct ctatcttaat    120 cggatattaa tccgactctt cttcttccca aaaattaata ttagtttcaa atccaaagca    180
acccacctca ttcaactttc cttcgatttt cttcaaattt ccagtttcca cttgctttca    240
ttgcttcttt cccgccgttt ctagatcttc aatcgagaaa gggatttgca acttttcaca    300
caaaaatctt agattaattg ttattaataa cttgttcatc aaaccactaa aaatcccgtg    360
tcatcttcga cttcttggtt aaaattcaat aaagagtgta actttttcatt gctataactt    420 aataatttgt ttgtgagaag agaactctag tcttacaggg accaacacca acaatcaaaa    480
tttagataat gaagaatagt tgctgatgca tgattaagat tgaatttatc aacaaaagat    540
aagtgttcat tatacaacac gtgattaatt gcatggtgta ttaaggccca ttaacgaagt    600
ccatggtaaa atgaaacggc atggcgttca ctaccccacc taatgaactg catgtcgtct    660
caaccatcaa catagaagct tcttgaagcc acctgagaaa tctggtagcg acactcttga    720
aagacacgtt ataagaaac ggaagaaga aacctgaaat ttcaagaaac ttgcagagct    780
ttctatctct tatcctcttc tctaccatca tttctcccta taaatacgcc aacgcacata    840
agtgtttgca ttcgaagaga gttctagcaa aacaaaacaa aacagagcaa acagagtaag    900
cgaaacg                                                               907

<210> SEQ ID NO 4
<211> LENGTH: 780
<212> TYPE: DNA
<213> ORGANISM: Arabidopsis thaliana
<220> FEATURE:
<223> OTHER INFORMATION: SEQ ID NO: 4  Contains promoter fragment from
      prAT1G52690, found in Genbank acc. AC008016)

<400> SEQUENCE: 4
agaaagtgta tatttagta aaatcctaaa tctaagcatt acactaacac gtggaaaata    60
acataccatt gacgattgac atggctaatt ttttgtggag gtgaatagtt tgaggattta    120
```

```
ttaccctaac gttgcttggt caagaagtga agtaggatga caggcaatag gaagatctta      180 aaccttttt  tccggtgaca attatttatg acttttatt gttgtcaaaa aatatattat      240
cagtaatata tcaataacga atacaataaa aactcatccg atcgattttc aagaatttat     300
agctatatta aaattacttc gaatccatgt aagaattgtg tattggttct ttttagaaaa     360
aagtaaatat ctatgcagta atggcggttg cataatatat gccttgagta gatgaatatc     420
caatatcaag ataacgtgag tcaccacgtg tctaacatct tccgtagctc cgttttacc     480 atgacgtgtc acatagatat aggtcatcat gaaaacgaga aacctaactt taacactcgc     540
acataactcc aagtttcgaa acttcgtcac atcaacctaa tcggggcacg tacctacaca     600
cctgtcgcga aactgcaaca cctatcttgt tctctcgccg accaagactt gctataaata     660
actctgacta acgagtcgga gacaactcac agttccaaac acacaaaaaa cacaagatct     720
aaaaaaaaaa gcttttatca tttagaaaaa tttggtttcg aatttcttcg aagagtgaaa     780
```

<210> SEQ ID NO 5
<211> LENGTH: 447
<212> TYPE: DNA
<213> ORGANISM: Arabidopsis thaliana
<220> FEATURE:
<223> OTHER INFORMATION: SEQ ID NO: 5  Contains promoter fragment from
      prAt2g37870, found in Genbank acc. no. AC007661, GI:6598780)

<400> SEQUENCE: 5

```
aaaccatatg ttgttgtagc ctactcattt ctatctgttt tactacattt ccgttgttat      60
atctaataat aagaattttc agctcgaatg ttgaatcctt atagtgtcta tattgaaaca     120
atgaaaacca aaagtgttct gaaacaaaga gagtgcaaaa agttgttgga gcctgtttta     180
tgaaagaaaa gtaagagag  aaacaaaaac aaacacgcaa gaaatcaaac gactaaacac     240
acaacagatg gtgaaatcta atcaaagta  agcataaatc aaatgattac agaatggggg     300
aaaaaattaa acggtataac cgtacacgtc accaaaacac aaccacccca ctaaaacatc     360
ttactagtta ctagtatata agaatcatca acgcactaag taagacactc aacaaaacaa     420
aacaagaagg agaatataag aagaagc                                          447
```

<210> SEQ ID NO 6
<211> LENGTH: 776
<212> TYPE: DNA
<213> ORGANISM: Arabidopsis thaliana
<220> FEATURE:
<223> OTHER INFORMATION: SEQ ID NO: 6  Contains promoter fragment from
      prAT5G43840 or prG1947, found in Genbank acc. AB026651,
      GI:4757407)

<400> SEQUENCE: 6

```
cgattttcga ataaattatt tgagcttttcc aaactgtaat tcaagtatta ttacttatat      60
agtgttagtg tacttcaaaa gttaaagcat aaattttctt atatttgaaa tgacctcttc     120
tttacaaaat cttcttaaaa ttatgcatta tcaatatatt aattgtatat atatatataa     180
tgtataattc tgcttgtgtc gtgcttaacc gtttgatttg gtgtggttag atctggtttt     240
cccccaaccc aattcaattg aatcaaggat caatcaaatt ttcaaaggat actcttgttc     300
tctacacaaa tctttcaaag ggttccacca aaatcccat  cattctgact tcagaataaa     360
caaacaaacc acgaaacgta tctctatgca ttcactacaa cgtgtcatgg gcgaaaacga     420
agcttataaa tgttggagca tagtcactaa atttataatg attaattaaa ttttagattt     480
tctgatattc atagaagaca aaagaacaca aaagtagcat cttccaatga atgtatgaca     540
```

-continued

```
ctatgatctc tcatttccat ttatagcaaa tcggctttgt ccacatcaaa gataactaat      600
aaatagactt atccaaaaca ctcaaaagca atacatttct atccaaaaat attaaacccc      660
aaaaatatag acagcataaa agcatcctca agcttcagct attcatcaca actattctct     720
cctctctctt tttttattaa aaaagctcaa atttatatag gttttttgtt cacaaa          776

<210> SEQ ID NO 7
<211> LENGTH: 928
<212> TYPE: DNA
<213> ORGANISM: Arabidopsis thaliana
<220> FEATURE:
<223> OTHER INFORMATION: SEQ ID NO: 7  Contains promoter fragment from
      prAt5g66780, found in Genbank acc. no. AB010700, GI:2828185)

<400> SEQUENCE: 7
tagtcttgtt gttttctcat tagataattt aaactggttt gcttctttat ttttggttgg       60
ataaagtgac cggttctggt catctgtttg agatgtaatt actatttcat aaaattagga     120
agttgaaagc caaatatatt tgtaactact ctttatttg taattttgct caaaaagtg       180 atgaaatgta gttttgatat atgaatatct accattatac ataagtatat ctgaacatgg    240
tacaacttat gaaagctaaa tgtcaatact tgcaaagata taacaaatac aagttacatg     300
aataagagat gtgtgttgaa tttataagtg tcattttctt ttcactttaa aacaaacttc     360
atcttctttt gtttcttatg tgtcaaagtt gccacagttg ctctatttga gtctttcagt     420
gtcagtctca gtcactgtac tgattttact ttttttgtt gagtgtgcca atgatgacat     480
cactcccacg tcctccatcc gtcttctttt aacggtcacg tggctcccac cctcttttct     540
cgatgtcttt accgacttgt tctagcccaa cttacttggg ccatttagat tttttggtgg     600
cccaagttgc taaaagagga tttatcatag aaatctgaac ccgttgcagc gctcaacaca     660
tgtcacagtc ctgacaaaca cgtattcaaa tccttgttaa gtcccgccac ctgtcaccag     720
agcaccacga ggcaaactct gatcaggaca ccgtcgtact attatgtcgg aagacaggaa     780
agcttaatta agcttaaacc tgacgtattt aacttcgtta actctacctt actaaagggt     840
tttaatttaa aacttatcat ctcctcgtaa gaataaaaac tacttactct ataaatttaa     900
gcttcaagaa acctccaaaa gcagagaa                                        928

<210> SEQ ID NO 8
<211> LENGTH: 460
<212> TYPE: DNA
<213> ORGANISM: Arabidopsis thaliana
<220> FEATURE:
<223> OTHER INFORMATION: SEQ ID NO: 8  Contains promoter fragment from
      prAt3g17520, found in Genbank acc. no. AB022219, GI:7321075)

<400> SEQUENCE: 8
gggttttact tacaataagc ccttactatt cattgaaaag ctcactaaac ttgtttatga       60
aaagcccact ggttattgta tacaagccca ttagcttcac agatgtgttt cagttgaagc     120
ctctctttgt ttttgcgagt cggttttccg caaaaagcaa tcgcttgcct cgttgtttgt     180
gtaacacgtg tcaagaacca cttaacacga atccaaaatc gagaagccaa agaagctgg     240 tactcgccac gtacttagcc acgcgtccta aacctatctc ttttcaact aatacataac     300 agagaagcaa tcacagcacc attcctcgga gaacacatca cagtaaacag aggtttttt     360 cttcttctga aacttgatat aagttatata accatataat attttgtgtt cgattagtgt     420
aacaaaaatg gggttagaga ggaaagtgta cggtttggtt                            460
```

<210> SEQ ID NO 9
<211> LENGTH: 936
<212> TYPE: DNA
<213> ORGANISM: Arabidopsis thaliana
<220> FEATURE:
<223> OTHER INFORMATION: SEQ ID NO: 9  Contains promoter fragment from
      prAt4g09600, found in Genbank acc. no. AL161831, GI:7321075)

<400> SEQUENCE: 9

```
gttaaatcct cactaggatc tctctttata ttaatggtta aaaacatatg catgttttgt    60
gtttttgcat cttcttttc atagacaaaa gcaagatgag tcttagaagg acatcaatgt    120
catagacatg gctttagtat cttttgagtg tgctttaaat gatgatgatt taccctgaac    180
ctgaaatttt acctattaat taatttaagt gtgcgttaaa ccataaacca tatactctga    240
acctgaaatt ggttctaaag cacaacctaa acttgagatt ggagaatgct ttaaaaggaa    300
aaaaaaatca aggaaaacca ttaatgagcc atcaaaaaat attcactaat atgacaagat    360
gcattgttta ttttttcttt cagaatcctc agaaactacc actaaactcc tcaaggaaca    420
aaaccatatc atgaattagg ctggcaattt aactctgaga cgtctttctt gtatagagaa    480
taaaacatac gcgtgtaaaa gaaaacgcgt gaatcgaatg atgagtgtta acgttcgatc    540
gagatgccac caaatctttt cattaaaatg aattgtggag gacataccac ttttaacgag    600
gtcatttcca ctgggtgaca tgtggactct actttgggtg gcatgttcat atctttccac    660
atcaccatgt aaacgtgaaa acacccacca cactcactta catctcaaac acatgtcttc    720
attatcgtac gtagctccaa aaaaaaaaat gaaaactagg tttagtgatt ctatttcgca    780
atgtataata tacaacttgt aaaaataaaa tatttgaata agcattataa ataaacccaa    840
agaggtgtta gatttatata cttaattgta gctactaaat agagaatcag agagaatagt    900
tttatatctt gcacgaaact gcatgctttt tgagac                               936
```

<210> SEQ ID NO 10
<211> LENGTH: 1192
<212> TYPE: DNA
<213> ORGANISM: artificial sequence
<220> FEATURE:
<223> OTHER INFORMATION: SEQ ID NO: 10  P26849 Drought inducible
      promoter-G481 combination vector, comprises the promoter sequence
      from the drought-inducible gene AT1G16850 fused to a G481 coding
      sequence lacking UTR sequences, and the plasmid also carries a
      kanamycin resistance marker

<400> SEQUENCE: 10

```
attgggtacg attttcatag gtctttcctc acgccagaag tgttgtttta ttttgttgat    60
tgagttatta attattggaa gcttttcttt caagcaaagt aaaatgcgta ataatgatta    120
gtcacatcca atggttagtc agtctattac accgttaatc aagctctggt catataattt    180
ttttattttt ggaactaaca cttattagtt taggtttcca tcacctattt aattcgtaat    240
tcttatacat gcatataata gagatacata tatacaaatt tatgatcatt tttgcacaac    300
atgtgatctc attcattagt atgcattatg cgaaaacctc gacgcgcaaa agacacgtaa    360
tagctaataa tgttactcat ttataatgat tgaagcaaga cgaaaacaac aacatatata    420
tcaaattgta aactagatat ttcttaaaag tgaaaaaaaa caaagaaata taaggacaa    480
ttttgagtca gtctcttaat attaaaacat atatacataa ataagcacaa acgtggttac    540
ctgtcttcat gcaatgtgga ctttagttta tctaatcaaa atcaaaataa aaggtgtaat    600
agttctcgtc atttttcaaa ttttaaaaat cagaaccaag tgattttgt ttgagtattg    660
atccattgtt taaacaattt aacacagtat atacgtctct tgagatgttg acatgatgat    720
```

```
aaaatacgag atcgtctctt ggttttcgaa ttttgaactt taatagatgg cggatacgcc      780
ttcgagccca gctggagatg gcggagaaag cggcggttcc gttagggagc aggatcgata      840
ccttcctata gctaatatca gcaggatcat gaagaaagcg ttgcctccta atggtaagat      900
tggaaaagat gctaaggata cagttcagga atgcgtctct gagttcatca gcttcatcac      960
tagcgaggcc agtgataagt gtcaaaaaga gaaaggaaa actgtgaatg gtgatgattt      1020
gttgtgggca atggcaacat taggatttga ggattacctg gaacctctaa agatatacct     1080
agcgaggtac agggagttgg agggtgataa taagggatca ggaaagagtg gagatggatc     1140
aaatagagat gctggtggcg gtgtttctgg tgaagaaatg ccgagctggt aa             1192
```

<210> SEQ ID NO 11
<211> LENGTH: 1031
<212> TYPE: DNA
<213> ORGANISM: artificial sequence
<220> FEATURE:
<223> OTHER INFORMATION: SEQ ID NO: 11  P26851 Ddrought inducible
  promoter-G481 combination vector, comprises the promoter sequence
  from the drought-inducible gene AT5G52300 fused to a G481 coding
  sequence lacking UTR sequences, and the plasmid also carries a
  kanamycin resistance marker

<400> SEQUENCE: 11

```
tgatgatgat gatgaagaag agaacgaatt ttgaaattgg cggttttgaa tttttaagaa       60
attaaaaaat atccccgtc gatttcaaga gggagatgga gataccaaag caactctcgc      120
cacttgtcgt cttttaattt taattgagta cgttatgccg ttttaaatgt tcaaaacagc      180
acacagttga tagctgaatt gatttttct tttgccgttt tgttatattt aaacaacaca      240
cagtgcattt gccaaataac tacatgatgg gccaataaac gtggaccgac taaaactaaa      300
taatagaaga tacatcgata ggcttctcta aagatcggat aaaagataat gtcgcatagc      360
cacgtagaga gcaactggct gagacgtggc aggacgaaac ggacgcatcg tacgtgtcag      420
aatcctacag aagtaaagag acagaagcca gagagaggtg gttcggccat atgtcatcgt      480
tctctctata aactttatgg aactttgttc tgattttctc agagacacga aaagaaagaa      540
aacaacacta gaacaaagag ggtttgattg attcacttga aaaagagaaa acacagcttt      600
ggaaaatggc ggatacgcct tcgagcccag ctggagatgg cggagaaagc ggcggttccg      660
ttagggagca ggatcgatac cttcctatag ctaatatcag caggatcatg aagaaagcgt      720
tgcctcctaa tggtaagatt ggaaaagatg ctaaggatac agttcaggaa tgcgtctctg      780
agttcatcag cttcatcact agcgaggcca gtgataagtg tcaaaaagag aaaggaaaa      840 ctgtgaatgg tgatgatttg ttgtgggcaa tggcaacatt aggatttgag gattacctgg      900
aacctctaaa gatataccta gcgaggtaca gggagttgga gggtgataat aagggatcag      960
gaaagagtgg agatggatca aatagagatg ctggtggcgg tgtttctggt gaagaaatgc     1020
cgagctggta a                                                         1031
```

<210> SEQ ID NO 12
<211> LENGTH: 1333
<212> TYPE: DNA
<213> ORGANISM: artificial sequence
<220> FEATURE:
<223> OTHER INFORMATION: SEQ ID NO: 12  P26852 (Drought inducible
  promoter-G481 combination vector, comprises the promoter sequence
  from the drought-inducible gene AT3G46230 fused to a G481 coding
  sequence lacking UTR sequences, and the plasmid also carries a
  kanamycin resistance marker

<400> SEQUENCE: 12

```
ttatttattc tcaattttcc catacgaatt ttttgtcttt atatttatca caaaaaaga      60
gtttgctctt taaaaaacta tactaatgta atttttttat tttattttct ctatcttaat    120
cggatattaa tccgactctt cttcttccca aaaattaata ttagtttcaa atccaaagca    180
acccacctca ttcaactttc cttcgatttt cttcaaattt ccagtttcca cttgctttca    240
ttgcttcttt cccgccgttt ctagatcttc aatcgagaaa gggatttgca acttttcaca    300
caaaaatctt agattaattg ttattaataa cttgttcatc aaaccactaa aaatcccgtg    360
tcatcttcga cttcttggtt aaaattcaat aaagagtgta acttttcatt gctataactt    420
aataatttgt ttgtgagaag agaactctag tcttacaggg accaacacca acaatcaaaa    480
tttagataat gaagaatagt tgctgatgca tgattaagat tgaatttatc aacaaaagat    540
aagtgttcat tatacaacac gtgattaatt gcatggtgta ttaaggccca ttaacgaagt    600
ccatggtaaa atgaaacggc atggcgttca ctaccccacc taatgaactg catgtcgtct    660
caaccatcaa catagaagct tcttgaagcc acctgagaaa tctggtagcg acactcttga    720
aagacacgtt ataagaaac ggaaagaaga aacctgaaat ttcaagaaac ttgcagagct    780
ttctatctct tatcctcttc tctaccatca tttctcccta taaatacgcc aacgcacata    840
agtgtttgca ttcgaagaga gttctagcaa aacaaaacaa acagagcaa acagagtaag    900
cgaaacgatg gcggatacgc cttcgagccc agctggagat ggcggagaaa gcggcggttc    960
cgttagggag caggatcgat accttcctat agctaatatc agcaggatca tgaagaaagc   1020
gttgcctcct aatggtaaga ttggaaaaga tgctaaggat acagttcagg aatgcgtctc   1080
tgagttcatc agcttcatca ctagcgaggc cagtgataag tgtcaaaaag agaaaggaa   1140
aactgtgaat ggtgatgatt tgttgtgggc aatggcaaca ttaggatttg aggattacct   1200
ggaacctcta aagatatacc tagcgaggta cagggagttg gagggtgata ataagggatc   1260
aggaaagagt ggagatggat caaatagaga tgctggtggc ggtgtttctg gtgaagaaat   1320
gccgagctgg taa                                                      1333
```

<210> SEQ ID NO 13
<211> LENGTH: 1206
<212> TYPE: DNA
<213> ORGANISM: artificial sequence
<220> FEATURE:
<223> OTHER INFORMATION: SEQ ID NO: 13 P26850 Drought inducible promoter-G481 combination vector, comprises the promoter sequence from the drought-inducible gene prAT1G52690 fused to a G481 coding sequence lacking UTR sequences, and the plasmid also carries a kanamycin resistance marker

<400> SEQUENCE: 13

```
agaaagtgta tattttagta aaatcctaaa tctaagcatt acactaacac gtggaaaata     60
acataccatt gacgattgac atggctaatt ttttgtggag gtgaatagtt tgaggattta    120
ttaccctaac gttgcttggt caagaagtga agtaggatga caggcaatag gaagatctta    180
aaccttttttt tccggtgaca attatttatg acttttttatt gttgtcaaaa aatatattat   240
cagtaatata tcaataacga atacaataaa aactcatccg atcgattttc aagaatttat    300
agctatatta aaattacttc gaatccatgt aagaattgtg tattggttct ttttagaaaa    360
aagtaaatat ctatgcagta atggcggttg cataatatat gccttgagta gatgaatatc    420
caatatcaag ataacgtgag tcaccacgtg tctaacatct tccgtagctc cgttttttacc   480
atgacgtgtc acatagatat aggtcatcat gaaaacgaga aacctaactt taacactcgc    540
```

```
acataactcc aagtttcgaa acttcgtcac atcaacctaa tcggggcacg tacctacaca    600
cctgtcgcga aactgcaaca cctatcttgt tctctcgccg accaagactt gctataaata    660
actctgacta acgagtcgga gacaactcac agttccaaac acacaaaaaa cacaagatct    720
aaaaaaaaaa gcttttatca tttagaaaaa tttggtttcg aatttcttcg aagagtgaaa    780
atggcggata cgccttcgag cccagctgga gatggcggag aaagcggcgg ttccgttagg    840
gagcaggatc gataccttcc tatagctaat atcagcagga tcatgaagaa agcgttgcct    900
cctaatggta agattggaaa agatgctaag gatacagttc aggaatgcgt ctctgagttc    960
atcagcttca tcactagcga ggccagtgat aagtgtcaaa aagagaaaag gaaaactgtg   1020
aatggtgatg atttgttgtg ggcaatggca acattaggat ttgaggatta cctggaacct   1080
ctaaagatat acctagcgag gtacaggagt tggagggtg ataataaggg atcaggaaag   1140
agtggagatg gatcaaatag agatgctggt ggcggtgttt ctggtgaaga aatgccgagc   1200
tggtaa                                                              1206
```

<210> SEQ ID NO 14
<211> LENGTH: 873
<212> TYPE: DNA
<213> ORGANISM: artificial sequence
<220> FEATURE:
<223> OTHER INFORMATION: SEQ ID NO: 14  P26853 Drought inducible
      promoter-G481 combination vector, comprises the promoter sequence
      from the drought-inducible gene AT2G37870 fused to a G481 coding
      sequence lacking UTR sequences, and the plasmid also carries a
      kanamycin resistance marker

<400> SEQUENCE: 14

```
aaaccatatg ttgttgtagc ctactcattt ctatctgttt tactacattt ccgttgttat     60
atctaataat aagaattttc agctcgaatg ttgaatcctt atagtgtcta tattgaaaca    120
atgaaaacca aaagtgttct gaaacaaaga gagtgcaaaa agttgttgga gcctgtttta    180
tgaaagaaaa gtaagagagag aaacaaaaac aaacacgcaa gaaatcaaac gactaaacac    240
acaacagatg gtgaaatcta atcaaagta agcataaatc aaatgattac agaatggggg    300
aaaaaattaa acggtataac cgtacacgtc accaaaacac aaccacccca ctaaaacatc    360
ttactagtta ctagtatata agaatcatca acgcactaag taagacactc aacaaaacaa    420
aacaagaagg agaatataag aagaagcatg gcggatacgc cttcgagccc agctggagat    480
ggcggagaaa gcggcggttc cgttagggag caggatcgat accttcctat agctaatatc    540
agcaggatca tgaagaaagc gttgcctcct aatggtaaga ttggaaaaga tgctaaggat    600
acagttcagg aatgcgtctc tgagttcatc agcttcatca ctagcgaggc cagtgataag    660
tgtcaaaaag agaaaaggaa aactgtgaat ggtgatgatt tgttgtgggc aatggcaaca    720
ttaggatttg aggattacct ggaacctcta aagatatacc tagcgaggta cagggagttg    780
gagggtgata ataagggatc aggaaagagt ggagatggat caaatagaga tgctggtggc    840
ggtgtttctg gtgaagaaat gccgagctgg taa                                 873
```

<210> SEQ ID NO 15
<211> LENGTH: 1202
<212> TYPE: DNA
<213> ORGANISM: artificial sequence
<220> FEATURE:
<223> OTHER INFORMATION: SEQ ID NO: 15  P26844 Drought inducible
      promoter-G481 combination vector, comprises the promoter sequence
      from the drought-inducible gene AT5G43840 (G1947) fused to a G481
      coding sequence lacking UTR sequences, and the plasmid also carries a kanamycin resistance marker

<400> SEQUENCE: 15

```
cgattttcga ataaattatt tgagctttcc aaactgtaat tcaagtatta ttacttatat    60
agtgttagtg tacttcaaaa gttaaagcat aaattttctt atatttgaaa tgacctcttc   120
tttacaaaat cttcttaaaa ttatgcatta tcaatatatt aattgtatat atatatataa   180
tgtataattc tgcttgtgtc gtgcttaacc gtttgatttg gtgtggttag atctggtttt   240
cccccaaccc aattcaattg aatcaaggat caatcaaatt ttcaaaggat actcttgttc   300
tctacacaaa tctttcaaag ggttccacca aaatcccat cattctgact tcagaataaa    360
caaacaaacc acgaaacgta tctctatgca ttcactacaa cgtgtcatgg gcgaaaacga   420
agcttataaa tgttggagca tagtcactaa atttataatg attaattaaa ttttagattt   480
tctgatattc atagaagaca aaagaacaca aaagtagcat cttccaatga atgtatgaca   540
ctatgatctc tcatttccat ttatagcaaa tcggctttgt ccacatcaaa gataactaat   600
aaatagactt atccaaaaca ctcaaaagca atacattct atccaaaaat attaaacccc    660
aaaatatag acagcataaa agcatcctca agcttcagct attcatcaca actattctct    720
cctctctctt tttttattaa aaaagctcaa atttatatag gttttttgtt cacaaaatgg   780
cggatacgcc ttcgagccca gctggagatg gcggagaaag cggcggttcc gttagggagc   840
aggatcgata ccttcctata gctaaatcga gcaggatcat gaagaaagcg ttgcctccta   900
atggtaagat tggaaaagat gctaaggata cagttcagga atgcgtctct gagttcatca   960
gcttcatcac tagcgaggcc agtgataagt gtcaaaaaga gaaaggaaa actgtgaatg    1020
gtgatgattt ttgtgggca atggcaacat taggatttga ggattacctg gaacctctaa   1080
agatataacct agcgaggtac agggagttgg agggtgataa taagggatca ggaaagagtg   1140
gagatggatc aaatagagat gctggtggcg gtgtttctgg tgaagaaatg ccgagctggt   1200
aa                                                                 1202
```

<210> SEQ ID NO 16
<211> LENGTH: 1354
<212> TYPE: DNA
<213> ORGANISM: artificial sequence
<220> FEATURE:
<223> OTHER INFORMATION: SEQ ID NO: 16  P26847 Drought inducible promoter-G481 combination vector, comprises the promoter sequence from the drought-inducible gene AT5G66780 fused to a G481 coding sequence lacking UTR sequences, and the plasmid also carries a kanamycin resistance marker

<400> SEQUENCE: 16

```
tagtcttgtt gttttctcat tagataattt aaactggttt gcttctttat ttttggttgg    60
ataaagtgac cggttctggt catctgtttg agatgtaatt actatttcat aaaattagga   120
agttgaaagc caaatatatt tgtaactact cttttatttg taattttgct caaaaaagtg   180
atgaaatgta gttttgatat atgaatatct accattatac ataagtatat ctgaacatgg   240
tacaacttat gaaagctaaa tgtcaatact tgcaaagata taacaaatac aagttacatg   300
aataagagat gtgtgttgaa tttataagtg tcattttctt ttcactttaa aacaaacttc   360
atcttctttt gtttcttatg tgtcaaagtt gccacagttg ctctatttga gtctttcagt   420
gtcagtctca gtcactgtac tgattttact ttttttgtt gagtgtgcca atgatgacat    480
cactcccacg tcctccatcc gtcttctttt aacggtcacg tggctcccac cctcttttct   540
cgatgtcttt accgacttgt tctagcccaa cttacttggg ccatttagat ttttggtgg    600
```

```
cccaagttgc taaaagagga tttatcatag aaatctgaac ccgttgcagc gctcaacaca    660
tgtcacagtc ctgacaaaca cgtattcaaa tccttgttaa gtcccgccac ctgtcaccag    720
agcaccacga ggcaaactct gatcaggaca ccgtcgtact attatgtcgg aagacaggaa    780
agcttaatta agcttaaacc tgacgtattt aacttcgtta actctacctt actaaagggt    840
tttaatttaa aacttatcat ctcctcgtaa gaataaaaac tacttactct ataaatttaa    900
gcttcaagaa acctccaaaa gcagagaaat ggcggatacg ccttcgagcc agctggaga    960 tggcggagaa agcggcggtt ccgttaggga gcaggatcga taccttccta tagctaatat   1020
cagcaggatc atgaagaaag cgttgcctcc taatggtaag attggaaaag atgctaagga   1080
tacagttcag gaatgcgtct ctgagttcat cagcttcatc actagcgagg ccagtgataa   1140
gtgtcaaaaa gagaaaagga aaactgtgaa tggtgatgat tgttgtggg caatggcaac   1200 attaggattt gaggattacc tggaacctct aaagatatac ctagcgaggt acaggagtt   1260 ggagggtgat aataagggat caggaaagag tggagatgga tcaaatagag atgctggtgg   1320
cggtgtttct ggtgaagaaa tgccgagctg gtaa                              1354
```

<210> SEQ ID NO 17
<211> LENGTH: 886
<212> TYPE: DNA
<213> ORGANISM: artificial sequence
<220> FEATURE:
<223> OTHER INFORMATION: SEQ ID NO: 17  P26846 Drought inducible
    promoter-G481 combination vector, comprises the promoter sequence
    from the drought-inducible gene AT3G17520 fused to a G481 coding
    sequence lacking UTR sequences, and the plasmid also carries a
    kanamycin resistance marker

<400> SEQUENCE: 17

```
gggttttact tacaataagc ccttactatt cattgaaaag ctcactaaac ttgtttatga     60
aaagcccact ggttattgta tacaagccca ttagcttcac agatgtgttt cagttgaagc    120
ctctctttgt ttttgcgagt cggttttccg caaaaagcaa tcgcttgcct cgttgtttgt    180
gtaacacgtg tcaagaacca cttaacacga atccaaaatc gagaagccaa aagaagctgg    240
tactcgccac gtacttagcc acgcgtccta aacctatctc tttttcaact aatacataac    300
agagaagcaa tcacagcacc attcctcgga gaacacatca cagtaaacag aggttttttt    360
cttcttctga aacttgatat aagttatata accatataat attttgtgtt cgattagtgt    420
aacaaaaatg gggttagaga ggaaagtgta cggtttggtt atggcggata cgccttcgag    480
cccagctgga gatggcggag aaagcggcgg ttccgttagg gagcaggatc gataccttcc    540
tatagctaat atcagcagga tcatgaagaa agcgttgcct cctaatggta agattggaaa    600
agatgctaag gatacagttc aggaatgcgt ctctgagttc atcagcttca tcactagcga    660
ggccagtgat aagtgtcaaa agagaaaag gaaaactgtg aatggtgatg atttgttgtg    720
ggcaatggca acattaggat ttgaggatta cctggaacct ctaaagatat acctagcgag    780
gtacagggag ttggagggtg ataataaggg atcaggaaag agtggagatg gatcaaatag    840
agatgctggt ggcggtgttt ctggtgaaga aatgccgagc tggtaa                   886
```

<210> SEQ ID NO 18
<211> LENGTH: 1362
<212> TYPE: DNA
<213> ORGANISM: artificial sequence
<220> FEATURE:
<223> OTHER INFORMATION: SEQ ID NO: 18  P26845 Drought inducible
    promoter-G481 combination vector, comprises the promoter sequence from the drought-inducible gene AT4G09600 fused to a G481 coding
sequence lacking UTR sequences, and the plasmid also carries a
kanamycin resistance marker

<400> SEQUENCE: 18

```
gttaaatcct cactaggatc tctctttata ttaatggtta aaaacatatg catgttttgt      60
gttttttgcat cttcttttc atagacaaaa gcaagatgag tcttagaagg acatcaatgt     120
catagacatg gctttagtat cttttgagtg tgctttaaat gatgatgatt taccctgaac    180
ctgaaatttt acctattaat taatttaagt gtgcgttaaa ccataaacca tatactctga    240
acctgaaatt ggttctaaag cacaacctaa acttgagatt ggagaatgct ttaaaaggaa    300
aaaaaaatca aggaaaacca ttaatgagcc atcaaaaaat attcactaat atgacaagat    360
gcattgttta ttttcttttt cagaatcctc agaaactacc actaaactcc tcaaggaaca    420
aaaccatatc atgaattagg ctggcaattt aactctgaga cgtctttctt gtatagagaa    480
taaaacatac gcgtgtaaaa gaaacgcgt gaatcgaatg atgagtgtta acgttcgatc     540
gagatgccac caaatctttt cattaaaatg aattgtggag acataccac ttttaacgag     600
gtcatttcca ctgggtgaca tgtggactct actttgggtg gcatgttcat atctttccac    660
atcaccatgt aaacgtgaaa acacccacca cactcactta catctcaaac acatgtcttc    720
attatcgtac gtagctccaa aaaaaaaaat gaaaactagg tttagtgatt ctatttcgca    780
atgtataata tacaacttgt aaaaataaaa tatttgaata agcattataa ataacccaa     840
agaggtgtta gatttatata cttaattgta gctactaaat agagaatcag agagaatagt    900
tttatatctt gcacgaaact gcatgctttt tgagacatgg cggatacgcc ttcgagccca    960
gctggagatg gcggagaaag cggcggttcc gttagggagc aggatcgata ccttcctata   1020
gctaatatca gcaggatcat gaagaaagcg ttgcctccta atggtaagat tggaaaagat   1080
gctaaggata cagttcagga atgcgtctct gagttcatca gcttcatcac tagcgaggcc   1140
agtgataagt gtcaaaaaga gaaaggaaa actgtgaatg tgatgatttt gttgtgggca    1200
atggcaacat taggatttga ggattacctg gaacctctaa agatatacct agcgaggtac   1260
agggagttgg agggtgataa taagggatca ggaaagagtg gagatggatc aaatagagat   1320
gctggtggcg gtgtttctgg tgaagaaatg ccgagctggt aa                      1362
```

<210> SEQ ID NO 19
<211> LENGTH: 1666
<212> TYPE: DNA
<213> ORGANISM: artificial sequence
<220> FEATURE:
<223> OTHER INFORMATION: SEQ ID NO: 19  P26859 Drought inducible
promoter-G1073 combination vector, comprises the promoter sequence
from the drought-inducible gene AT1G16850 fused to a G1073 coding
sequence lacking UTR sequences, and the plasmid also carries a
kanamycin resistance marker

<400> SEQUENCE: 19

```
attgggtacg attttcatag gtctttcctc acgccagaag tgttgtttta ttttgttgat     60
tgagttatta attattggaa gcttttcttt caagcaaagt aaaatgcgta ataatgatta   120
gtcacatcca atggttagtc agtctattac accgttaatc aagctctggt catataatt    180
ttttattttt ggaactaaca cttattagtt taggtttcca tcacctattt aattcgtaat   240
tcttatacat gcataaata gagatacata tatacaaatt tatgatcatt tttgcacaac    300
atgtgatctc attcattagt atgcattatg cgaaaacctc gacgcgcaaa agacacgtaa   360
tagctaataa tgttactcat ttataatgat tgaagcaaga cgaaaacaac aacatatata   420
```

```
tcaaattgta aactagatat ttcttaaaag tgaaaaaaaa caaagaaata taaaggacaa      480
ttttgagtca gtctcttaat attaaaacat atatacataa ataagcacaa acgtggttac      540
ctgtcttcat gcaatgtgga ctttagttta tctaatcaaa atcaaaataa aaggtgtaat      600
agttctcgtc atttttcaaa ttttaaaaat cagaaccaag tgattttttgt ttgagtattg     660 atccattgtt taaacaattt aacacagtat atacgtctct tgagatgttg acatgatgat      720
aaaatacgag atcgtctctt ggttttcgaa ttttgaactt taatagatgt ctagttatat      780
gcaccctctt ctagggcaag aactgcatct acagagacct gaagattcca gaaccccacc     840
tgatcaaaat aacatggaac ttaacagatc tgaagcagac gaagcaaagg ccgagaccac     900
tcccaccggt ggagccacca gctcagccac agcctctggc tcttcctccg gacgtcgtcc     960
acgtggtcgt cctgcaggtt ccaaaaacaa acccaaacct ccgacgatta taactagaga    1020
tagtcctaac gtccttagat cacacgttct tgaagtcacc tccggttcgg acatatccga    1080
ggcagtctcc acctacgcca ctcgtcgcgg ctgcggcgtt tgcattataa gcggcacggg    1140
tgcggtcact aacgtcacga tacggcaacc tgcggctccg gctggtggag gtgtgattac    1200
cctgcatggt cggtttgaca ttttgtcttt gaccggtact gcgcttccac cgcctgcacc    1260
accgggagca ggaggtttga cggtgtatct agccggaggt caaggacaag ttgtaggagg    1320
gaatgtggct ggttcgttaa ttgcttcggg accggtagtg ttgatggctg cttcttttgc    1380
aaacgcagtt tatgataggt taccgattga agaggaagaa accccaccgc cgagaaccac    1440
cggggtgcag cagcagcagc cggaggcgtc tcagtcgtcg gaggttacgg ggagtggggc    1500
ccaggcgtgt gagtcaaacc tccaaggtgg aaatggtgga ggaggtgttg ctttctacaa    1560
tcttggaatg aatatgaaca attttcaatt ctccggggga gatatttacg gtatgagcgg    1620
cggtagcgga ggaggtggtg gcggtgcgac tagacccgcg ttttag                   1666
```

<210> SEQ ID NO 20
<211> LENGTH: 1505
<212> TYPE: DNA
<213> ORGANISM: artificial sequence
<220> FEATURE:
<223> OTHER INFORMATION: SEQ ID NO: 20  P26861 Drought inducible
     promoter-G1073 combination vector, comprises the promoter sequence
     from the drought-inducible gene AT5G52300 fused to a G1073 coding
     sequence lacking UTR sequences, and the plasmid also carries a
     kanamycin resistance marker

<400> SEQUENCE: 20

```
tgatgatgat gatgaagaag agaacgaatt ttgaaattgg cggttttgaa tttttaagaa       60
attaaaaaat atccccccgtc gatttcaaga gggagatgga gataccaaag caactctcgc    120
cacttgtcgt cttttaattt taattgagta cgttatgccg ttttaaatgt tcaaaacagc    180
acacagttga tagctgaatt gatttttttct tttgccgttt tgttatattt aaacaacaca    240
cagtgcattt gccaaataac tacatgatgg gccaataaac gtggaccgac taaaactaaa    300
taatagaaga tacatcgata ggcttctcta aagatcggat aaaagataat gtcgcatagc    360
cacgtagaga gcaactggct gagacgtggc aggacgaaac ggacgcatcg tacgtgtcag    420
aatcctacag aagtaaagag acagaagcca gagagaggtg gttcggccat atgtcatcgt    480
tctctctata aactttatgg aactttgttc tgattttctc agagacacga aaagaaagaa    540
aacaacacta gaacaaagag ggtttgattg attcacttga aaaagagaaa acacagcttt    600
ggaaaatgtc tagttatatg caccctcttc tagggcaaga actgcatcta cagagacctg    660
```

-continued

| | |
|---|---|
| aagattccag aaccccacct gatcaaaata acatggaact taacagatct gaagcagacg | 720 |
| aagcaaaggc cgagaccact cccaccggtg gagccaccag ctcagccaca gcctctggct | 780 |
| cttcctccgg acgtcgtcca cgtggtcgtc ctgcaggttc aaaaacaaa cccaaacctc | 840 |
| cgacgattat aactagagat agtcctaacg tccttagatc acacgttctt gaagtcacct | 900 |
| ccggttcgga catatccgag gcagtctcca cctacgccac tcgtcgcggc tgcggcgttt | 960 |
| gcattataag cggcacgggt gcggtcacta acgtcacgat acggcaacct gcggctccgg | 1020 |
| ctggtggagg tgtgattacc ctgcatggtc ggtttgacat tttgtctttg accggtactg | 1080 |
| cgcttccacc gcctgcacca ccgggagcag gaggtttgac ggtgtatcta gccggaggtc | 1140 |
| aaggacaagt tgtaggaggg aatgtggctg gttcgttaat tgcttcggga ccggtagtgt | 1200 |
| tgatggctgc ttcttttgca aacgcagttt atgataggtt accgattgaa gaggaagaaa | 1260 |
| ccccaccgcc gagaaccacc ggggtgcagc agcagcagcc ggaggcgtct cagtcgtcgg | 1320 |
| aggttacggg gagtggggcc caggcgtgtg agtcaaacct ccaaggtgga atggtggag | 1380 |
| gaggtgttgc tttctacaat cttggaatga atatgaacaa ttttcaattc tccggggag | 1440 |
| atatttacgg tatgagcggc ggtagcggag gaggtggtgg cggtgcgact agacccgcgt | 1500 |
| tttag | 1505 |

<210> SEQ ID NO 21
<211> LENGTH: 1807
<212> TYPE: DNA
<213> ORGANISM: artificial sequence
<220> FEATURE:
<223> OTHER INFORMATION: SEQ ID NO: 21  P26862 Drought inducible
      promoter-G1073 combination vector, comprises the promoter sequence
      from the drought-inducible gene AT3G46230 fused to a G1073 coding
      sequence lacking UTR sequences, and the plasmid also carries a
      kanamycin resistance marker

<400> SEQUENCE: 21

| | |
|---|---|
| ttatttattc tcaattttcc catacgaatt ttttgtcttt atatttatca caaaaaaga | 60 |
| gtttgctctt taaaaaacta tactaatgta atttttttat tttattttct ctatcttaat | 120 |
| cggatattaa tccgactctt cttcttccca aaaattaata ttagtttcaa atccaaagca | 180 |
| acccacctca ttcaactttc cttcgatttt cttcaaattt ccagtttcca cttgctttca | 240 |
| ttgcttcttt cccgccgttt ctagatcttc aatcgagaaa gggatttgca acttttcaca | 300 |
| caaaaatctt agattaattg ttattaataa cttgttcatc aaaccactaa aaatcccgtg | 360 |
| tcatcttcga cttcttggtt aaaattcaat aaagagtgta acttttcatt gctataactt | 420 |
| aataatttgt ttgtgagaag agaactctag tcttacaggg accaacacca acaatcaaaa | 480 |
| tttagataat gaagaatagt tgctgatgca tgattaagat tgaatttatc aacaaaagat | 540 |
| aagtgttcat tatacaacac gtgattaatt gcatggtgta ttaaggccca ttaacgaagt | 600 |
| ccatggtaaa atgaaacggc atggcgttca ctaccccacc taatgaactg catgtcgtct | 660 |
| caaccatcaa catagaagct tcttgaagcc acctgagaaa tctggtagcg acactcttga | 720 |
| aagcacgtt ataagaaac ggaaagaaga aacctgaaat ttcaagaaac ttgcagagct | 780 |
| ttctatctct tatcctcttc tctaccatca tttctcccta taaatacgcc aacgcacata | 840 |
| agtgtttgca ttcgaagaga gttctagcaa aacaaaacaa aacagagcaa acagagtaag | 900 |
| cgaaacgatg tctagttata tgcaccctct tctagggcaa gaactgcatc tacagagacc | 960 |
| tgaagattcc agaaccccac ctgatcaaaa taacatggaa cttaacagat ctgaagcaga | 1020 |
| cgaagcaaag gccgagacca ctcccaccgg tggagccacc agctcagcca cagcctctgg | 1080 |

```
ctcttcctcc ggacgtcgtc cacgtggtcg tcctgcaggt tccaaaaaca aacccaaacc    1140
tccgacgatt ataactagag atagtcctaa cgtccttaga tcacacgttc ttgaagtcac    1200
ctccggttcg gacatatccg aggcagtctc cacctacgcc actcgtcgcg gctgcggcgt    1260
ttgcattata agcggcacgg gtgcggtcac taacgtcacg atacggcaac ctgcggctcc    1320
ggctggtgga ggtgtgatta ccctgcatgg tcggtttgac attttgtctt tgaccggtac    1380
tgcgcttcca ccgcctgcac caccgggagc aggaggtttg acggtgtatc tagccggagg    1440
tcaaggacaa gttgtaggag ggaatgtggc tggttcgtta attgcttcgg gaccggtagt    1500
gttgatggct gcttcttttg caaacgcagt ttatgatagg ttaccgattg aagaggaaga    1560
aaccccaccg ccgagaacca ccggggtgca gcagcagcag ccggaggcgt ctcagtcgtc    1620
ggaggttacg gggagtgggg cccaggcgtg tgagtcaaac ctccaaggtg gaaatggtgg    1680
aggaggtgtt gctttctaca atcttggaat gaatatgaac aattttcaat tctccggggg    1740
agatatttac ggtatgagcg gcggtagcgg aggaggtggt ggcggtgcga ctagacccgc    1800
gttttag                                                               1807

<210> SEQ ID NO 22
<211> LENGTH: 1680
<212> TYPE: DNA
<213> ORGANISM: artificial sequence
<220> FEATURE:
<223> OTHER INFORMATION: SEQ ID NO: 22  P26860 Drought inducible
      promoter-G1073 combination vector, comprises the promoter sequence
      from the drought-inducible gene AT1G52690 fused to a G1073 coding
      sequence lacking UTR sequences, and the plasmid also carries a
      kanamycin resistance marker

<400> SEQUENCE: 22
agaaagtgta tattttagta aaatcctaaa tctaagcatt acactaacac gtggaaaata      60
acataccatt gacgattgac atggctaatt ttttgtggag gtgaatagtt tgaggattta     120
ttaccctaac gttgcttggt caagaagtga agtaggatga caggcaatag gaagatctta     180
aacctttttt tccggtgaca attatttatg acttttatt gttgtcaaaa aatatattat     240
cagtaatata tcaataacga atacaataaa aactcatccg atcgattttc aagaatttat     300
agctatatta aaattacttc gaatccatgt aagaattgtg tattggttct ttttagaaaa     360
aagtaaatat ctatgcagta atggcggttg cataatatat gccttgagta gatgaatatc     420
caatatcaag ataacgtgag tcaccacgtg tctaacatct tccgtagctc cgttttttacc    480 atgacgtgtc acatagatat aggtcatcat gaaaacgaga aacctaactt taacactcgc     540
acataactcc aagtttcgaa acttcgtcac atcaacctaa tcggggcacg tacctacaca     600
cctgtcgcga aactgcaaca cctatcttgt tctctcgccg accaagactt gctataaata     660
actctgacta acgagtcgga gacaactcac agttccaaac acacaaaaaa cacaagatct     720
aaaaaaaaaa gcttttatca tttagaaaaa tttggtttcg aatttcttcg aagagtgaaa     780
atgtctagtt atatgcaccc tcttctaggg caagaactgc atctacagag acctgaagat     840
tccagaaccc cacctgatca aaataacatg gaacttaaca gatctgaagc agacgaagca     900
aaggccgaga ccactcccac cggtggagcc accagctcag ccacagcctc tggctcttcc     960
tccggacgtc gtccacgtgg tcgtcctgca ggttccaaaa acaaacccaa acctccgacg    1020
attataacta gagatagtcc taacgtcctt agatcacacg ttcttgaagt cacctccggt    1080
tcggacatat ccgaggcagt ctccacctac gccactcgtc gcggctgcgg cgtttgcatt    1140
```

```
ataagcggca cgggtgcggt cactaacgtc acgatacggc aacctgcggc tccggctggt    1200
ggaggtgtga ttaccctgca tggtcggttt gacattttgt ctttgaccgg tactgcgctt    1260
ccaccgcctg caccaccggg agcaggaggt tgacggtgt atctagccgg aggtcaagga     1320
caagttgtag gagggaatgt ggctggttcg ttaattgctt cgggaccggt agtgttgatg    1380
gctgcttctt ttgcaaacgc agtttatgat aggttaccga ttgaagagga agaaacccca   1440
ccgccgagaa ccaccggggt gcagcagcag cagccgagg cgtctcagtc gtcggaggtt     1500
acggggagtg gggcccaggc gtgtgagtca aacctccaag gtggaaatgg tggaggaggt    1560
gttgctttct acaatcttgg aatgaatatg aacaattttc aattctccgg gggagatatt    1620
tacggtatga gcggcggtag cggaggaggt ggtggcggtg cgactagacc cgcgttttag    1680
```

<210> SEQ ID NO 23
<211> LENGTH: 1347
<212> TYPE: DNA
<213> ORGANISM: artificial sequence
<220> FEATURE:
<223> OTHER INFORMATION: SEQ ID NO: 23  P26863 Drought inducible
      promoter-G1073 combination vector, comprises the promoter sequence
      from the drought-inducible gene AT2G37870 fused to a G1073 coding
      sequence lacking UTR sequences, and the plasmid also carries a
      kanamycin resistance marker

<400> SEQUENCE: 23

```
aaaccatatg ttgttgtagc ctactcattt ctatctgttt tactacattt ccgttgttat     60
atctaataat aagaattttc agctcgaatg ttgaatcctt atagtgtcta tattgaaaca    120
atgaaaacca aaagtgttct gaaacaaaga gagtgcaaaa agttgttgga gcctgtttta    180
tgaaagaaaa gtaagagag aaacaaaaac aaacacgcaa gaaatcaaac gactaaacac     240
acaacagatg gtgaaatcta atcaaagta agcataaatc aaatgattac agaatggggg    300
aaaaaattaa acggtataac cgtacacgtc accaaaacac aaccacccca ctaaaacatc    360
ttactagtta ctagtatata agaatcatca acgcactaag taagacactc aacaaaacaa    420
aacaagaagg agaatataag aagaagcatg tctagttata tgcaccctct tctagggcaa    480
gaactgcatc tacagagacc tgaagattcc agaaccccac ctgatcaaaa taacatggaa    540
cttaacagat ctgaagcaga cgaagcaaag gccgagacca ctcccaccgg tggagccacc    600
agctcagcca cagcctctgg ctcttcctcc ggacgtcgtc cacgtggtcg tcctgcaggt    660
tccaaaaaca acccaaaacc tccgacgatt ataactagag atagtcctaa cgtccttaga   720
tcacacgttc ttgaagtcac ctccggttcg gacatatccg aggcagtctc cacctacgcc    780
actcgtcgcg gctgcggcgt ttgcattata agcggcacgg gtgcggtcac taacgtcacg    840
atacggcaac ctgcggctcc ggctggtgga ggtgtgatta ccctgcatgg tcggtttgac    900
attttgtctt tgaccggtac tgcgcttcca ccgcctgcac caccgggagc aggaggtttg    960
acggtgtatc tagccggagg tcaaggacaa gttgtaggag gaatgtggc tggttcgtta    1020 attgcttcgg gaccggtagt gttgatggct gcttcttttg caaacgcagt ttatgatagg   1080
ttaccgattg aagaggaaga aaccccaccg ccgagaacca ccggggtgca gcagcagcag   1140
ccggaggcgt ctcagtcgtc ggaggttacg gggagtgggg cccaggcgtg tgagtcaaac   1200
ctccaaggtg gaaatggtgg aggaggtgtt gctttctaca atcttggaat gaatatgaac   1260
aattttcaat tctccggggg agatatttac ggtatgagcg gcggtagcgg aggaggtggt   1320
ggcggtgcga ctagacccgc gttttag                                       1347
```

<210> SEQ ID NO 24
<211> LENGTH: 1676
<212> TYPE: DNA
<213> ORGANISM: artificial sequence
<220> FEATURE:
<223> OTHER INFORMATION: SEQ ID NO: 24  P26854 Drought inducible
      promoter-G1073 combination vector, comprises the promoter sequence
      from the drought-inducible gene AT5G43840 (G1947) fused to a G1073
      coding sequence lacking UTR sequences, and the plasmid also
      carries a kanamycin resistance marker

<400> SEQUENCE: 24

```
cgattttcga ataaattatt tgagctttcc aaactgtaat tcaagtatta ttacttatat     60
agtgttagtg tacttcaaaa gttaaagcat aaatttctt atatttgaaa tgacctcttc    120
tttacaaaat cttcttaaaa ttatgcatta tcaatatatt aattgtatat atatatataa    180
tgtataattc tgcttgtgtc gtgcttaacc gtttgatttg gtgtggttag atctggtttt    240
cccccaaccc aattcaattg aatcaaggat caatcaaatt ttcaaaggat actcttgttc    300
tctacacaaa tctttcaaag ggttccacca aaaatcccat cattctgact tcagaataaa    360
caaacaaacc acgaaacgta tctctatgca ttcactacaa cgtgtcatgg gcgaaaacga    420
agcttataaa tgttggagca tagtcactaa atttataatg attaattaaa ttttagattt    480
tctgatattc atagaagaca aaagaacaca aaagtagcat cttccaatga atgtatgaca    540
ctatgatctc tcatttccat ttatagcaaa tcggctttgt ccacatcaaa gataactaat    600
aaatagactt atccaaaaca ctcaaaagca atacatttct atccaaaaat attaaacccc    660
aaaaatatag acagcataaa agcatcctca agcttcagct attcatcaca actattctct    720
cctctctctt tttttattaa aaaagctcaa atttatatag gttttttgtt cacaaaatgt    780
ctagttatat gcaccctctt ctagggcaag aactgcatct acagagacct gaagattcca    840
gaaccccacc tgatcaaaat aacatggaac ttaacagatc tgaagcagac gaagcaaagg    900
ccgagaccac tcccaccggt ggagccacca gctcagccac agcctctggc tcttcctccg    960
gacgtcgtcc acgtggtcgt cctgcaggtt ccaaaaacaa acccaaacct ccgacgatta   1020
taactagaga tagtcctaac gtccttagat cacacgttct tgaagtcacc tccggttcgg   1080
acatatccga ggcagtctcc acctacgcca ctcgtcgcgg ctgcggcgtt tgcattataa   1140
gcggcacggg tgcggtcact aacgtcacga tacggcaacc tgcggctccg gctggtggag   1200
gtgtgattac cctgcatggt cggtttgaca ttttgtcttt gaccggtact gcgcttccac   1260
cgcctgcacc accgggagca ggaggtttga cggtgtatct agccggaggt caaggacaag   1320
ttgtaggagg gaatgtggct ggttcgttaa ttgcttcggg accggtagtg ttgatggctg   1380
cttcttttgc aaacgcagtt tatgataggt taccgattga agaggaagaa accccaccgc   1440
cgagaaccac cggggtgcag cagcagcagc cggaggcgtc tcagtcgtcg gaggttacgg   1500
ggagtggggc ccaggcgtgt gagtcaaacc tccaaggtgg aaatggtgga ggaggtgttg   1560
cttttctacaa tcttggaatg aatatgaaca attttcaatt ctccggggga gatatttacg   1620
gtatgagcgg cggtagcgga ggaggtggtg gcggtgcgac tagacccgcg ttttag         1676
```

<210> SEQ ID NO 25
<211> LENGTH: 1828
<212> TYPE: DNA
<213> ORGANISM: artificial sequence
<220> FEATURE:
<223> OTHER INFORMATION: SEQ ID NO: 25  P26857 Drought inducible
      promoter-G1073 combination vector, comprises the promoter sequence
      from the drought-inducible gene AT5G66780 fused to a G1073 coding
      sequence lacking UTR sequences, and the plasmid also carries a

```
<400> SEQUENCE: 25
tagtcttgtt gttttctcat tagataattt aaactggttt gcttctttat ttttggttgg      60
ataaagtgac cggttctggt catctgtttg agatgtaatt actatttcat aaaattagga     120
agttgaaagc caaatatatt tgtaactact cttttatttg taattttgct caaaaagtg      180 atgaaatgta gttttgatat atgaaatatct accattatac ataagtatat ctgaacatgg    240
tacaacttat gaaagctaaa tgtcaatact tgcaaagata taacaaatac aagttacatg     300
aataagagat gtgtgttgaa tttataagtg tcattttctt ttcactttaa aacaaacttc     360
atcttctttt gtttcttatg tgtcaaagtt gccacagttg ctctatttga gtctttcagt    420
gtcagtctca gtcactgtac tgattttact ttttttgtt gagtgtgcca atgatgacat     480
cactcccacg tcctccatcc gtcttctttt aacggtcacg tggctcccac cctctttct    540 cgatgtcttt accgacttgt tctagcccaa cttacttggg ccatttagat tttttggtgg   600
cccaagttgc taaagagga tttatcatag aaatctgaac ccgttgcagc gctcaacaca    660
tgtcacagtc ctgacaaaca cgtattcaaa tccttgttaa gtcccgccac ctgtcaccag   720
agcaccacga ggcaaactct gatcaggaca ccgtcgtact attatgtcgg aagacaggaa   780
agcttaatta agcttaaacc tgacgtattt aacttcgtta actctacctt actaaagggt   840 tttaattttaa aacttatcat ctcctcgtaa gaataaaaac tacttactct ataaatttaa   900
gcttcaagaa acctccaaaa gcagagaaat gtctagttat atgcaccctc ttctagggca   960
agaactgcat ctacagagac ctgaagattc cagaacccca cctgatcaaa ataacatgga  1020
acttaacaga tctgaagcag acgaagcaaa ggccgagacc actcccaccg gtggagccac  1080
cagctcagcc acagcctctg gctcttcctc cggacgtcgt ccacgtggtc gtcctgcagg  1140
ttccaaaaac aaacccaaac ctccgacgat tataactaga gatagtccta acgtccttag  1200
atcacacgtt cttgaagtca cctccggttc ggacatatcc gaggcagtct ccacctacgc  1260
cactcgtcgc ggctgcggcg tttgcattat aagcggcacg ggtgcggtca ctaacgtcac  1320
gatacggcaa cctgcggctc cggctggtgg aggtgtgatt accctgcatg gtcggtttga  1380
cattttgtct ttgaccggta ctgcgcttcc accgcctgca ccaccgggag caggaggttt  1440
gacggtgtat ctagccggag gtcaaggaca agttgtagga gggaatgtgg ctggttcgtt  1500
aattgcttcg ggaccggtag tgttgatggc tgcttctttt gcaaacgcag tttatgatag  1560
gttaccgatt gaagaggaag aaaccccacc gccgagaacc accggggtgc agcagcagca  1620
gccggaggcg tctcagtcgt cggaggttac ggggagtggg gcccaggcgt gtgagtcaaa  1680
cctccaaggt ggaaatggtg gaggaggtgt tgctttctac aatcttggaa tgaatatgaa  1740
caattttcaa ttctccgggg gagatattta cggtatgagc ggcggtagcg gaggaggtgg  1800
tggcggtgcg actagacccg cgttttag                                     1828
```

<210> SEQ ID NO 26
<211> LENGTH: 1360
<212> TYPE: DNA
<213> ORGANISM: artificial sequence
<220> FEATURE:
<223> OTHER INFORMATION: SEQ ID NO: 26  P26856 Drought inducible
      promoter-G1073 combination vector, comprises the promoter sequence
      from the drought-inducible gene AT3G17520 fused to a G1073 coding
      sequence lacking UTR sequences, and the plasmid also carries a
      kanamycin resistance marker

<400> SEQUENCE: 26

```
gggtttact  tacaataagc  ccttactatt  cattgaaaag  ctcactaaac  ttgtttatga    60
aaagcccact  ggttattgta  tacaagccca  ttagcttcac  agatgtgttt  cagttgaagc   120
ctctctttgt  ttttgcgagt  cggttttccg  caaaaagcaa  tcgcttgcct  cgttgtttgt   180
gtaacacgtg  tcaagaacca  cttaacacga  atccaaaatc  gagaagccaa  agaagctgg    240 tactcgccac  gtacttagcc  acgcgtccta  aacctatctc  ttttcaact   aatacataac   300 agagaagcaa  tcacagcacc  attcctcgga  gaacacatca  cagtaaacag  aggttttttt   360
cttcttctga  aacttgatat  aagttatata  accatataat  attttgtgtt  cgattagtgt   420
aacaaaaatg  gggttagaga  ggaaagtgta  cggtttggtt  atgtctagtt  atatgcaccc   480
tcttctaggg  caagaactgc  atctacagag  acctgaagat  tccagaaccc  cacctgatca   540
aaataacatg  gaacttaaca  gatctgaagc  agacgaagca  aaggccgaga  ccactcccac   600
cggtggagcc  accagctcag  ccacagcctc  tggctcttcc  tccggacgtc  gtccacgtgg   660
tcgtcctgca  ggttccaaaa  acaaacccaa  acctccgacg  attataacta  gagatagtcc   720
taacgtcctt  agatcacacg  ttcttgaagt  cacctccggt  tcggacatat  ccgaggcagt   780
ctccacctac  gccactcgtc  gcggctgcgg  cgtttgcatt  ataagcggca  cgggtgcggt   840
cactaacgtc  acgatacggc  aacctgcggc  tccggctggt  ggaggtgtga  ttaccctgca   900
tggtcggttt  gacattttgt  ctttgaccgg  tactgcgctt  ccaccgcctg  caccaccggg   960
agcaggaggt  ttgacggtgt  atctagccgg  aggtcaagga  caagttgtag  gagggaatgt  1020
ggctggttcg  ttaattgctt  cgggaccggt  agtgttgatg  gctgcttctt  ttgcaaacgc  1080
agtttatgat  aggttaccga  ttgaagagga  agaaacccca  ccgccgagaa  ccaccggggt  1140
gcagcagcag  cagccggagg  cgtctcagtc  gtcggaggtt  acgggagtg   gggcccaggc  1200 gtgtgagtca  aacctccaag  gtggaaatgg  tggaggaggt  gttgctttct  acaatcttgg  1260
aatgaatatg  aacaattttc  aattctccgg  gggagatatt  tacggtatga  gcggcggtag  1320
cggaggaggt  ggtggcggtg  cgactagacc  cgcgttttag                          1360
```

<210> SEQ ID NO 27
<211> LENGTH: 1836
<212> TYPE: DNA
<213> ORGANISM: artificial sequence
<220> FEATURE:
<223> OTHER INFORMATION: SEQ ID NO: 27  P26855 Drought inducible
      promoter-G1073 combination vector, comprises the promoter sequence
      from the drought-inducible gene AT4G09600 fused to a G1073 coding
      sequence lacking UTR sequences, and the plasmid also carries a
      kanamycin resistance marker

<400> SEQUENCE: 27

```
gttaaatcct  cactaggatc  tctctttata  ttaatggtta  aaaacatatg  catgttttgt    60 gttttttgcat  cttctttttc  atagacaaaa  gcaagatgag  tcttagaagg  acatcaatgt   120
catagacatg  gctttagtat  cttttgagtg  tgcctttaaat gatgatgatt  taccctgaac   180
ctgaaatttt  acctattaat  taatttaagt  gtgcgttaaa  ccataaacca  tatactctga   240
acctgaaatt  ggttctaaag  cacaacctaa  acttgagatt  ggagaatgct  ttaaaggaa    300 aaaaaaatca  aaggaaaccca  ttaatgagcc  atcaaaaaat  attcactaat  atgacaagat   360
gcattgttta  tttttctttt  cagaatcctc  agaaactacc  actaaactcc  tcaaggaaca   420 aaccatatc   atgaattagg  ctggcaattt  aactctgaga  cgtctttctt  gtatagaaa    480 taaaacatac  gcgtgtaaaa  gaaaacgcgt  gaatcgaatg  atgagtgtta  acgttcgatc   540
```

```
gagatgccac caaatctttt cattaaaatg aattgtggag gacataccac ttttaacgag    600
gtcatttcca ctgggtgaca tgtggactct actttgggtg gcatgttcat atctttccac    660
atcaccatgt aaacgtgaaa acacccacca cactcactta catctcaaac acatgtcttc    720
attatcgtac gtagctccaa aaaaaaaaat gaaaactagg tttagtgatt ctatttcgca    780
atgtataata tacaacttgt aaaaataaaa tatttgaata agcattataa ataaacccaa    840
agaggtgtta gatttatata cttaattgta gctactaaat agagaatcag agagaatagt    900
tttatatctt gcacgaaact gcatgctttt tgagacatgt ctagttatat gcaccctctt    960
ctagggcaag aactgcatct acagagacct gaagattcca gaaccccacc tgatcaaaat   1020
aacatggaac ttaacagatc tgaagcagac gaagcaaagg ccgagaccac tcccaccggt   1080
ggagccacca gctcagccac agcctctggc tcttcctccg gacgtcgtcc acgtggtcgt   1140
cctgcaggtt ccaaaaacaa acccaaacct ccgacgatta aactagaga tagtcctaac    1200 gtccttagat cacacgttct tgaagtcacc tccggttcgg acatatccga ggcagtctcc   1260
acctacgcca ctcgtcgcgg ctgcggcgtt tgcattataa gcggcacggg tgcggtcact   1320
aacgtcacga tacggcaacc tgcggctccg gctggtggag gtgtgattac cctgcatggt   1380
cggtttgaca ttttgtcttt gaccggtact gcgcttccac cgcctgcacc accgggagca   1440
ggaggtttga cggtgtatct agccggaggt caaggacaag ttgtaggagg gaatgtggct   1500
ggttcgttaa ttgcttcggg accggtagtg ttgatggctg cttcttttgc aaacgcagtt   1560
tatgataggt taccgattga agaggaagaa accccaccgc cgagaaccac cggggtgcag   1620
cagcagcagc cggaggcgtc tcagtcgtcg gaggttacgg ggagtggggc ccaggcgtgt   1680
gagtcaaacc tccaaggtgg aaatggtgga ggaggtgttg cttttctacaa tcttggaatg   1740 aatatgaaca attttcaatt ctccggggga gatatttacg gtatgagcgg cggtagcgga   1800
ggaggtggtg gcggtgcgac tagacccgcg ttttag                             1836

<210> SEQ ID NO 28
<211> LENGTH: 1201
<212> TYPE: DNA
<213> ORGANISM: artificial sequence
<220> FEATURE:
<223> OTHER INFORMATION: SEQ ID NO: 28  Drought inducible promoter-G47
      combination vector, comprises the promoter sequence from the
      drought-inducible gene AT1G16850 fused to a G47 coding sequence
      lacking UTR sequences, and the plasmid also carries a kanamycin
      resistance marker

<400> SEQUENCE: 28
attgggtacg attttcatag gtctttcctc acgccagaag tgttgtttta ttttgttgat     60
tgagttatta attattggaa gcttttctttt caagcaaagt aaaatgcgta ataatgatta   120
gtcacatcca atggttagtc agtctattac accgttaatc aagctctggt catataattt    180
ttttattttt ggaactaaca cttattagtt taggtttcca tcacctattt aattcgtaat    240
tcttatacat gcatataata gagatacata tatacaaatt tatgatcatt tttgcacaac    300
atgtgatctc attcattagt atgcattatg cgaaaacctc gacgcgcaaa agacacgtaa    360
tagctaataa tgttactcat ttataatgat tgaagcaaga cgaaaacaac aacatatata    420
tcaaattgta aactagatat ttcttaaaag tgaaaaaaaa caaagaaata taaggacaa     480 ttttgagtca gtctcttaat attaaaacat atatacataa ataagcacaa acgtggttac    540
ctgtcttcat gcaatgtgga cttagtttta tctaatcaaa atcaaaataa aaggtgtaat    600
agttctcgtc attttttcaaa ttttaaaaat cagaaccaag tgattttttgt ttgagtattg   660
```

```
atccattgtt taaacaattt aacacagtat atacgtctct tgagatgttg acatgatgat      720
aaaatacgag atcgtctctt ggttttcgaa ttttgaactt taatagatgg attacagaga      780
atccaccggt gaaagtcagt caaagtacaa aggaatccgt cgtcggaaat ggggcaaatg      840
ggtatcagag attagagttc cgggaactcg tgaccgtctc tggttaggtt cattctcaac      900
agcagaaggt gccgccgtag cacacgacgt tgctttcttc tgtttacacc aacctgattc      960
tttagaatct ctcaatttcc ctcatttgct taatccttca ctcgtttcca gaacttctcc     1020
gagatctatc cagcaagctg cttctaacgc cggcatggcc attgacgccg aatcgtcca      1080 cagtaccagc gtgaactctg gatgcggaga tacgacgacg tattacgaga atggagctga     1140
tcaagtggag ccgttgaata tttcagtgta tgattatctg ggcggccacg atcacgtttg     1200
a                                                                     1201
```

<210> SEQ ID NO 29
<211> LENGTH: 1040
<212> TYPE: DNA
<213> ORGANISM: artificial sequence
<220> FEATURE:
<223> OTHER INFORMATION: SEQ ID NO: 29  Drought inducible promoter-G47 combination vector, comprises the promoter sequence from the drought-inducible gene AT5G52300 fused to a G47 coding sequence lacking UTR sequences, and the plasmid also carries a kanamycin resistance marker

<400> SEQUENCE: 29

```
tgatgatgat gatgaagaag agaacgaatt tgaaattggg cggttttgaa tttttaagaa        60
attaaaaaat atccccgtc gatttcaaga gggagatgga gataccaaag caactctcgc       120
cacttgtcgt cttttaattt taattgagta cgttatgccg ttttaaatgt tcaaaacagc      180
acacagttga tagctgaatt gatttttttct tttgccgttt tgttatattt aaacaacaca      240
cagtgcattt gccaaataac tacatgatgg gccaataaac gtggaccgac taaaactaaa      300
taatagaaga tacatcgata ggcttctcta aagatcggat aaaagataat gtcgcatagc      360
cacgtagaga gcaactggct gagacgtggc aggacgaaac ggacgcatcg tacgtgtcag      420
aatcctacag aagtaaagag acagaagcca gagagaggtg gttcggccat atgtcatcgt      480
tctctctata aactttatgg aactttgttc tgatttttctc agagacacga aaagaaagaa      540
aacaacacta gaacaaagag ggtttgattg attcacttga aaaagagaaa acacagcttt      600
ggaaaatgga ttacagagaa tccaccggtg aaagtcagtc aaagtacaaa ggaatccgtc      660
gtcggaaatg gggcaaatgg gtatcagaga ttagagttcc gggaactcgt gaccgtctct      720
ggttaggttc attctcaaca gcagaaggtg ccgccgtagc acacgacgtt gctttcttct      780
gtttacacca acctgattct ttagaatctc tcaatttccc tcatttgctt aatccttcac      840
tcgtttccag aacttctccg agatctatcc agcaagctgc ttctaacgcc ggcatggcca      900
ttgacgccgg aatcgtccac agtaccagcg tgaactctgg atgcggagat acgacgacgt      960
attacgagaa tggagctgat caagtggagc cgttgaatat ttcagtgtat gattatctgg     1020
gcggccacga tcacgtttga                                                  1040
```

<210> SEQ ID NO 30
<211> LENGTH: 1342
<212> TYPE: DNA
<213> ORGANISM: artificial sequence
<220> FEATURE:
<223> OTHER INFORMATION: SEQ ID NO: 30  Drought inducible promoter-G47 combination vector, comprises the promoter sequence from the -continued drought-inducible gene AT3G46230 fused to a G47 coding sequence
lacking UTR sequences, and the plasmid also carries a kanamycin
resistance marker

<400> SEQUENCE: 30

```
ttatttattc tcaattttcc catacgaatt ttttgtcttt atatttatca caaaaaaga      60
gtttgctctt taaaaaacta tactaatgta atttttttat tttattttct ctatcttaat    120
cggatattaa tccgactctt cttcttccca aaaattaata ttagtttcaa atccaaagca    180
acccacctca ttcaactttc cttcgatttt cttcaaattt ccagtttcca cttgctttca    240
ttgcttcttt cccgccgttt ctagatcttc aatcgagaaa gggatttgca acttttcaca    300
caaaaatctt agattaattg ttattaataa cttgttcatc aaaccactaa aaatcccgtg    360
tcatcttcga cttcttggtt aaaattcaat aaagagtgta acttttcatt gctataactt    420
aataatttgt ttgtgagaag agaactctag tcttacaggg accaacacca acaatcaaaa    480
tttagataat gaagaatagt tgctgatgca tgattaagat tgaatttatc acaaaaagat    540
aagtgttcat tatacaacac gtgattaatt gcatggtgta ttaaggccca ttaacgaagt    600
ccatggtaaa atgaaacggc atggcgttca ctaccccacc taatgaactg catgtcgtct    660
caaccatcaa catagaagct tcttgaagcc acctgagaaa tctggtagcg acactcttga    720
aagacacgtt ataagaaac ggaaagaaga aacctgaaat ttcaagaaac ttgcagagct    780
ttctatctct tatcctcttc tctaccatca tttctcccta taaatacgcc aacgcacata    840
agtgtttgca ttcgaagaga gttctagcaa aacaaaacaa aacagagcaa acagagtaag    900
cgaaacgatg gattacagag aatccaccgg tgaaagtcag tcaaagtaca aaggaatccg    960
tcgtcggaaa tggggcaaat gggtatcaga gattagagtt ccgggaactc gtgaccgtct   1020
ctggttaggt tcattctcaa cagcagaagg tgccgccgta gcacgacg ttgctttctt    1080
ctgtttacac caacctgatt ctttagaatc tctcaatttc cctcatttgc ttaatccttc   1140
actcgtttcc agaacttctc cgagatctat ccagcaagct gcttctaacg ccggcatggc   1200
cattgacgcc ggaatcgtcc acagtaccag cgtgaactct ggatgcggag atacgacgac   1260
gtattacgag aatggagctg atcaagtgga gccgttgaat atttcagtgt atgattatct   1320
gggcggccac gatcacgttt ga                                            1342
```

<210> SEQ ID NO 31
<211> LENGTH: 1215
<212> TYPE: DNA
<213> ORGANISM: artificial sequence
<220> FEATURE:
<223> OTHER INFORMATION: SEQ ID NO: 31 Drought inducible promoter-G47
combination vector, comprises the promoter sequence from the
drought-inducible gene AT1G52690 fused to a G47 coding sequence
lacking UTR sequences, and the plasmid also carries a kanamycin
resistance marker

<400> SEQUENCE: 31

```
agaaagtgta tattttagta aaatcctaaa tctaagcatt acactaacac gtggaaaata     60
acataccatt gacgattgac atggctaatt ttttgtggag gtgaatagtt tgaggattta   120
ttaccctaac gttgcttggt caagaagtga agtaggatga caggcaatag gaagatctta   180
aaccttttt tccggtgaca attatttatg acttttatt gttgtcaaaa aatatattat    240
cagtaatata tcaataacga atacaataaa aactcatccg atcgattttc aagaatttat    300
agctatatta aaattacttc gaatccatgt aagaattgtg tattggttct ttttagaaaa    360
aagtaaatat ctatgcagta atggcggttg cataatatat gccttgagta gatgaatatc    420
```

```
caatatcaag ataacgtgag tcaccacgtg tctaacatct tccgtagctc cgtttttacc      480
atgacgtgtc acatagatat aggtcatcat gaaaacgaga aacctaactt taacactcgc      540
acataactcc aagtttcgaa acttcgtcac atcaacctaa tcggggcacg tacctacaca      600
cctgtcgcga aactgcaaca cctatcttgt tctctcgccg accaagactt gctataaata      660
actctgacta acgagtcgga gacaactcac agttccaaac acacaaaaaa cacaagatct      720
aaaaaaaaaa gcttttatca tttagaaaaa tttggtttcg aatttcttcg aagagtgaaa      780
atggattaca gagaatccac cggtgaaagt cagtcaaagt acaaggaatc cgtcgtcgg       840 aaatggggca atgggtatc agagattaga gttccgggaa ctcgtgaccg tctctggtta      900
ggttcattct caacagcaga aggtgccgcc gtagcacacg acgttgcttt cttctgttta      960
caccaacctg attctttaga atctctcaat ttccctcatt tgcttaatcc ttcactcgtt     1020
tccagaactt ctccgagatc tatccagcaa gctgcttcta acgccggcat ggccattgac     1080
gccggaatcg tccacagtac cagcgtgaac tctggatgcg gagatacgac gacgtattac     1140
gagaatggag ctgatcaagt ggagccgttg aatatttcag tgtatgatta tctgggcggc     1200
cacgatcacg tttga                                                      1215
```

<210> SEQ ID NO 32
<211> LENGTH: 882
<212> TYPE: DNA
<213> ORGANISM: artificial sequence
<220> FEATURE:
<223> OTHER INFORMATION: SEQ ID NO: 32  Drought inducible promoter-G47 combination vector, comprises the promoter sequence from the drought-inducible gene AT2G37870 fused to a G47 coding sequence lacking UTR sequences, and the plasmid also carries a kanamycin resistance marker

<400> SEQUENCE: 32

```
aaaccatatg ttgttgtagc ctactcattt ctatctgttt tactacattt ccgttgttat       60
atctaataat aagaattttc agctcgaatg ttgaatcctt atagtgtcta tattgaaaca      120
atgaaaacca aaagtgttct gaaacaaaga gagtgcaaaa agttgttgga gcctgtttta      180
tgaaagaaaa gtaaagagag aaacaaaaac aaacacgcaa gaaatcaaac gactaaaacac     240 acaacagatg gtgaaatcta aatcaaagta agcataaatc aaatgattac agaatggggg     300
aaaaaattaa acggtataac cgtacacgtc accaaaacac aaccaccca ctaaaacatc      360 ttactagtta ctagtatata agaatcatca acgcactaag taagacactc aacaaaacaa     420
aacaagaagg agaatataag aagaagcatg gattacagag aatccaccgg tgaaagtcag     480
tcaaagtaca aaggaatccg tcgtcggaaa tggggcaaat gggtatcaga gattagagtt     540
ccgggaactc gtgaccgtct ctggttaggt tcattctcaa cagcagaagg tgccgccgta     600
gcacacgacg ttgctttctt ctgtttacac caacctgatt ctttagaatc tctcaatttc     660
cctcatttgc ttaatccttc actcgttttcc agaacttctc cgagatctat ccagcaagct     720
gcttctaacg ccggcatggc cattgacgcc ggaatcgtcc acagtaccag cgtgaactct     780
ggatgcggag atacgacgac gtattacgag aatggagctg atcaagtgga gccgttgaat     840
atttcagtgt atgattatct gggcggccac gatcacgttt ga                         882
```

<210> SEQ ID NO 33
<211> LENGTH: 1211
<212> TYPE: DNA
<213> ORGANISM: artificial sequence
<220> FEATURE:

<223> OTHER INFORMATION: SEQ ID NO: 33  P26869 Drought inducible
promoter-G47 combination vector, comprises the promoter sequence
from the drought-inducible gene AT5G43840 (G1947) fused to a G47
coding sequence lacking UTR sequences, and the plasmid also
carries a kanamycin resistance marker

<400> SEQUENCE: 33

```
cgattttcga ataaattatt tgagctttcc aaactgtaat tcaagtatta ttacttatat     60
agtgttagtg tacttcaaaa gttaaagcat aaattttctt atatttgaaa tgacctcttc    120
tttacaaaat cttcttaaaa ttatgcatta tcaatatatt aattgtatat atatatataa    180
tgtataattc tgcttgtgtc gtgcttaacc gtttgatttg gtgtggttag atctggtttt    240
cccccaaccc aattcaattg aatcaaggat caatcaaatt ttcaaaggat actcttgttc    300
tctacacaaa tctttcaaag ggttccacca aaaatcccat cattctgact tcagaataaa    360
caaacaaacc acgaaacgta tctctatgca ttcactacaa cgtgtcatgg gcgaaaacga    420
agcttataaa tgttggagca tagtcactaa atttataatg attaattaaa ttttagattt    480
tctgatattc atagaagaca aaagaacaca aaagtagcat cttccaatga atgtatgaca    540
ctatgatctc tcatttccat ttatagcaaa tcggctttgt ccacatcaaa gataactaat    600
aaatagactt atccaaaaca ctcaaaagca atacatttct atccaaaaat attaaacccc    660
aaaaatatag acagcataaa agcatcctca agcttcagct attcatcaca actattctct    720
cctctctctt tttttattaa aaaagctcaa atttatatag gttttttgtt cacaaaatgg    780
attacagaga atccaccggt gaaagtcagt caaagtacaa aggaatccgt cgtcggaaat    840
ggggcaaatg ggtatcagag attagagttc cgggaactcg tgaccgtctc tggttaggtt    900
cattctcaac agcagaaggt gccgccgtag cacacgacgt tgctttcttc tgtttacacc    960
aacctgattc tttagaatct ctcaatttcc ctcatttgct taatccttca ctcgtttcca   1020
gaacttctcc gagatctatc cagcaagctg cttctaacgc cggcatggcc attgacgccg   1080
gaatcgtcca cagtaccagc gtgaactctg gatgcggaga tacgacgacg tattacgaga   1140
atggagctga tcaagtggag ccgttgaata tttcagtgta tgattatctg ggcggccacg   1200
atcacgtttg a                                                       1211
```

<210> SEQ ID NO 34
<211> LENGTH: 1363
<212> TYPE: DNA
<213> ORGANISM: artificial sequence
<220> FEATURE:
<223> OTHER INFORMATION: SEQ ID NO: 34  P26872 Drought inducible
promoter-G47 combination vector, comprises the promoter sequence
from the drought-inducible gene AT5G66780 fused to a G47 coding
sequence lacking UTR sequences, and the plasmid also carries a
kanamycin resistance marker

<400> SEQUENCE: 34

```
tagtcttgtt gttttctcat tagataattt aaactggttt gcttctttat ttttggttgg     60
ataaagtgac cggttctggt catctgtttg agatgtaatt actatttcat aaaattagga    120
agttgaaagc caaatatatt tgtaactact cttttatttg taattttgct caaaaaagtg    180
atgaaatgta gttttgatat atgaatatct accattatac ataagtatat ctgaacatgg    240
tacaacttat gaaagctaaa tgtcaatact tgcaaagata taacaaatac aagttacatg    300
aataagagat gtgtgttgaa tttataagtg tcattttctt ttcactttaa aacaaacttc    360
atcttctttt gtttcttatg tgtcaaagtt gccacagttg ctctatttga gtctttcagt    420
gtcagtctca gtcactgtac tgatttttact ttttttttgtt gagtgtgcca atgatgacat    480
```

```
cactcccacg tcctccatcc gtcttctttt aacggtcacg tggctcccac cctcttttct    540
cgatgtcttt accgacttgt tctagcccaa cttacttggg ccatttagat tttttggtgg    600
cccaagttgc taaaagagga tttatcatag aaatctgaac ccgttgcagc gctcaacaca    660
tgtcacagtc ctgacaaaca cgtattcaaa tccttgttaa gtcccgccac ctgtcaccag    720
agcaccacga ggcaaactct gatcaggaca ccgtcgtact attatgtcgg aagacaggaa    780
agcttaatta agcttaaacc tgacgtattt aacttcgtta actctacctt actaaagggt    840
tttaatttaa aacttatcat ctcctcgtaa gaataaaaac tacttactct ataaatttaa    900
gcttcaagaa acctccaaaa gcagagaaat ggattacaga gaatccaccg gtgaaagtca    960
gtcaaagtac aaaggaatcc gtcgtcggaa atggggcaaa tgggtatcag agattagagt   1020
tccgggaact cgtgaccgtc tctgttaggt tcattctca acagcagaag gtgccgccgt   1080
agcacacgac gttgctttct tctgtttaca ccaacctgat tctttagaat ctctcaattt   1140
ccctcatttg cttaatcctt cactcgtttc cagaacttct ccgagatcta tccagcaagc   1200
tgcttctaac gccggcatgg ccattgacgc cggaatcgtc cacagtacca gcgtgaactc   1260
tggatgcgga gatacgacga cgtattacga gaatggagct gatcaagtgg agccgttgaa   1320
tatttcagtg tatgattatc tgggcggcca cgatcacgtt tga                     1363
```

<210> SEQ ID NO 35
<211> LENGTH: 895
<212> TYPE: DNA
<213> ORGANISM: artificial sequence
<220> FEATURE:
<223> OTHER INFORMATION: SEQ ID NO: 35 P26871 Drought inducible
      promoter-G47 combination vector, comprises the promoter sequence
      from the drought-inducible gene AT3G17520 fused to a G47 coding
      sequence lacking UTR sequences, and the plasmid also carries a
      kanamycin resistance marker

<400> SEQUENCE: 35

```
gggttttact tacaataagc ccttactatt cattgaaaag ctcactaaac ttgtttatga     60
aaagcccact ggttattgta tacaagccca ttagcttcac agatgtgttt cagttgaagc    120
ctctctttgt ttttgcgagt cggttttccg caaaaagcaa tcgcttgcct cgttgtttgt    180
gtaacacgtg tcaagaacca cttaacacga atccaaaatc gagaagccaa agaagctgg     240 tactcgccac gtacttagcc acgcgtccta aacctatctc ttttcaact aatacataac    300 agagaagcaa tcacagcacc attcctcgga gaacacatca cagtaaacag aggttttttt    360
cttcttctga aacttgatat aagttatata accatataat attttgtgtt cgattagtgt    420
aacaaaaatg gggttagaga ggaaagtgta cggtttggtt atggattaca gagaatccac    480
cggtgaaagt cagtcaaagt acaaaggaat ccgtcgtcgg aaatggggca atgggtatc    540 agagattaga gttccgggaa ctcgtgaccg tctctggtta ggttcattct caacagcaga    600
aggtgccgcc gtagcacacg acgttgcttt cttctgttta caccaacctg attctttaga    660
atctctcaat ttccctcatt tgcttaatcc ttcactcgtt tccagaactt ctccgagatc    720
tatccagcaa gctgcttcta acgccggcat ggccattgac gccggaatcg tccacagtac    780
cagcgtgaac tctggatgcg gagatacgac gacgtattac gagaatggag ctgatcaagt    840
ggagccgttg aatatttcag tgtatgatta tctgggcggc cacgatcacg tttga          895
```

<210> SEQ ID NO 36
<211> LENGTH: 1371
<212> TYPE: DNA

<213> ORGANISM: artificial sequence
<220> FEATURE:
<223> OTHER INFORMATION: SEQ ID NO: 36  P26870 Drought inducible
promoter-G47 combination vector, comprises the promoter sequence
from the drought-inducible gene AT4G09600 fused to a G47 coding
sequence lacking UTR sequences, and the plasmid also carries a
kanamycin resistance marker; DNA

<400> SEQUENCE: 36

| | | | | |
|---|---|---|---|---|
| gttaaatcct | cactaggatc | tctctttata | ttaatggtta | aaaacatatg catgttttgt | 60 |
| gttttttgcat | cttcttttc | atagacaaaa | gcaagatgag | tcttagaagg acatcaatgt | 120 |
| catagacatg | gctttagtat | cttttgagtg | tgctttaaat | gatgatgatt tacccctgaac | 180 |
| ctgaaatttt | acctattaat | taatttaagt | gtgcgttaaa | ccataaacca tatactctga | 240 |
| acctgaaatt | ggttctaaag | cacaacctaa | acttgagatt | ggagaatgct ttaaaaggaa | 300 |
| aaaaaaatca | aggaaaacca | ttaatgagcc | atcaaaaaat | attcactaat atgacaagat | 360 |
| gcattgttta | ttttctttt | cagaatcctc | agaaactacc | actaaactcc tcaaggaaca | 420 |
| aaaccatatc | atgaattagg | ctggcaattt | aactctgaga | cgtctttctt gtatagaaaa | 480 |
| taaaacatac | gcgtgtaaaa | gaaaacgcgt | gaatcgaatg | atgagtgtta acgttcgatc | 540 |
| gagatgccac | caaatctttt | cattaaaatg | aattgtggag | gacataccac ttttaacgag | 600 |
| gtcatttcca | ctgggtgaca | tgtggactct | actttgggtg | gcatgttcat atctttccac | 660 |
| atcaccatgt | aaacgtgaaa | acacccacca | cactcactta | catctcaaac acatgtcttc | 720 |
| attatcgtac | gtagctccaa | aaaaaaaaat | gaaaactagg | tttagtgatt ctatttcgca | 780 |
| atgtataata | tacaacttgt | aaaaataaaa | tatttgaata | agcattataa ataaacccaa | 840 |
| agaggtgtta | gatttatata | cttaattgta | gctactaaat | agagaatcag agagaatagt | 900 |
| tttatatctt | gcacgaaact | gcatgctttt | tgagacatgg | attacagaga atccaccggt | 960 |
| gaaagtcagt | caaagtacaa | aggaatccgt | cgtcggaaat | ggggcaaatg gtatcagag | 1020 |
| attagagttc | cgggaactcg | tgaccgtctc | tggttaggtt | cattctcaac agcagaaggt | 1080 |
| gccgccgtag | cacacgacgt | tgctttcttc | tgtttacacc | aacctgattc tttagaatct | 1140 |
| ctcaatttcc | ctcatttgct | taatccttca | ctcgtttcca | gaacttctcc gagatctatc | 1200 |
| cagcaagctg | cttctaacgc | cggcatggcc | attgacgccg | gaatcgtcca cagtaccagc | 1260 |
| gtgaactctg | gatgcggaga | tacgacgacg | tattacgaga | atggagctga tcaagtggag | 1320 |
| ccgttgaata | tttcagtgta | tgattatctg | ggcggccacg | atcacgtttg a | 1371 |

<210> SEQ ID NO 37
<211> LENGTH: 1351
<212> TYPE: DNA
<213> ORGANISM: artificial sequence
<220> FEATURE:
<223> OTHER INFORMATION: SEQ ID NO: 37  Drought inducible promoter-G1274
combination vector, comprises the promoter sequence from the
drought-inducible gene AT1G16850 fused to a G1274 coding sequence
lacking UTR sequences, and the plasmid also carries a kanamycin
resistance marker

<400> SEQUENCE: 37

| | | | | |
|---|---|---|---|---|
| attgggtacg | attttcatag | gtctttcctc | acgccagaag | tgttgtttta ttttgttgat | 60 |
| tgagttatta | attattggaa | gcttttcttt | caagcaaagt | aaaatgcgta ataatgatta | 120 |
| gtcacatcca | atggttagtc | agtctattac | accgttaatc | aagctctggt catataattt | 180 |
| ttttattttt | ggaactaaca | cttattagtt | taggttccca | tcacctattt aattcgtaat | 240 |
| tcttatacat | gcatataata | gagatacata | tatacaaatt | tatgatcatt tttgcacaac | 300 |

```
atgtgatctc attcattagt atgcattatg cgaaaacctc gacgcgcaaa agacacgtaa      360
tagctaataa tgttactcat ttataatgat tgaagcaaga cgaaaacaac aacatatata      420
tcaaattgta aactagatat ttcttaaaag tgaaaaaaaa caaagaaata taaaggacaa      480
ttttgagtca gtctcttaat attaaaacat atatacataa ataagcacaa acgtggttac      540
ctgtcttcat gcaatgtgga ctttagttta tctaatcaaa atcaaaataa aaggtgtaat      600
agttctcgtc attttcaaa ttttaaaaat cagaaccaag tgattttttgt ttgagtattg      660 atccattgtt taaacaattt aacacagtat atacgtctct tgagatgttg acatgatgat      720
aaaatacgag atcgtctctt ggttttcgaa ttttgaactt taatagatga atatctctca      780
aaaccctagc cctaatttta cgtacttctc cgatgaaaac tttattaatc cgtttatgga      840
taacaacgat ttctcaaatt tgatgttctt tgacatagat gaaggaggta acaatggatt      900
aatcgaggaa gagatctcat ctccgacaag catcgtttcg tcggagacat ttaccgggga      960
aagcggcgga tccggcagcg caacaacgtt gagtaaaaag gaatcaacta atagaggaag     1020
taaagagagt gatcagacga aggagacggg tcatcgagtt gcatttagaa cgagatcgaa     1080
gattgatgtg atggatgatg gttttaaatg gaggaagtat ggcaagaaat ctgtcaaaaa     1140
caacattaac aagaggaatt actacaaatg ctcaagtgaa ggttgctcgg tgaagaagag     1200
ggtagagaga gatggtgacg atgcagctta tgtaattaca acatatgaag gagtccataa     1260
ccatgagagt ctctctaatg tctattacaa tgaaatggtt ttatcttatg atcatgataa     1320
ctggaaccaa cactctcttc ttcgatctta a                                     1351

<210> SEQ ID NO 38
<211> LENGTH: 1190
<212> TYPE: DNA
<213> ORGANISM: artificial sequence
<220> FEATURE:
<223> OTHER INFORMATION: SEQ ID NO: 38  Drought inducible promoter-G1274
      combination vector, comprises the promoter sequence from the
      drought-inducible gene AT5G52300 fused to a G1274 coding sequence
      lacking UTR sequences, and the plasmid also carries a kanamycin
      resistance marker

<400> SEQUENCE: 38
tgatgatgat gatgaagaag agaacgaatt ttgaaattgg cggttttgaa ttttaagaa        60 attaaaaaat atccccgtc gatttcaaga gggagatgga gataccaaag caactctcgc      120
cacttgtcgt cttttaattt taattgagta cgttatgccg ttttaaatgt tcaaaacagc     180
acacagttga tagctgaatt gattttttct tttgccgttt tgttatattt aaacaacaca     240
cagtgcattt gccaaataac tacatgatgg gccaataaac gtggaccgac taaaactaaa     300
taatagaaga tacatcgata ggcttctcta aagatcggat aaaagataat gtcgcatagc     360
cacgtagaga gcaactggct gagacgtggc aggacgaaac ggacgcatcg tacgtgtcag     420
aatcctacag aagtaaagag acagaagcca gagagaggtg gttcggccat atgtcatcgt     480
tctctctata aactttatgg aactttgttc tgattttctc agagacacga aagaaagaa      540 aacaacacta gaacaaagag ggtttgattg attcacttga aaagagaaa acacagcttt      600 ggaaaatgaa tatctctcaa aaccctagcc ctaattttac gtacttctcc gatgaaaact     660
ttattaatcc gtttatggat aacaacgatt tctcaaattt gatgttcttt gacatagatg     720
aaggaggtaa caatggatta atcgaggaag agatctcatc tccgacaagc atcgtttcgt     780
cggagacatt taccggggaa agcggcggat ccggcagcgc aacaacgttg agtaaaaagg     840
```

```
aatcaactaa tagaggaagt aaagagagtg atcagacgaa ggagacgggt catcgagttg    900
catttagaac gagatcgaag attgatgtga tggatgatgg ttttaaatgg aggaagtatg    960
gcaagaaatc tgtcaaaaac aacattaaca agaggaatta ctacaaatgc tcaagtgaag   1020
gttgctcggt gaagaagagg gtagagagag atggtgacga tgcagcttat gtaattacaa   1080
catatgaagg agtccataac catgagagtc tctctaatgt ctattacaat gaaatggttt   1140
tatcttatga tcatgataac tggaaccaac actctcttct tcgatcttaa               1190
```

<210> SEQ ID NO 39
<211> LENGTH: 1492
<212> TYPE: DNA
<213> ORGANISM: artificial sequence
<220> FEATURE:
<223> OTHER INFORMATION: SEQ ID NO: 39  Drought inducible promoter-G1274
      combination vector, comprises the promoter sequence from the
      drought-inducible gene AT3G46230 fused to a G1274 coding sequence
      lacking UTR sequences, and the plasmid also carries a kanamycin
      resistance marker

<400> SEQUENCE: 39

```
ttatttattc tcaattttcc catacgaatt ttttgtcttt atatttatca caaaaaaaga     60
gtttgctctt taaaaaacta tactaatgta attttttttat tttattttct ctatcttaat   120
cggatattaa tccgactctt cttcttccca aaaattaata ttagtttcaa atccaaagca   180
acccacctca ttcaactttc cttcgatttt cttcaaattt ccagtttcca cttgctttca   240
ttgcttcttt cccgccgttt ctagatcttc aatcgagaaa gggatttgca acttttcaca   300
caaaaatctt agattaattg ttattaataa cttgttcatc aaaccactaa aaatcccgtg   360
tcatcttcga cttcttggtt aaaattcaat aaagagtgta acttttcatt gctataactt   420 aataaatttgt ttgtgagaag agaactctag tcttacaggg accaacacca acaatcaaaa   480
tttagataat gaagaatagt tgctgatgca tgattaagat tgaatttatc aacaaaagat   540
aagtgttcat tatacaacac gtgattaatt gcatggtgta ttaaggccca ttaacgaagt   600
ccatggtaaa atgaaacggc atggcgttca ctaccccacc taatgaactg catgtcgtct   660
caaccatcaa catagaagct tcttgaagcc acctgagaaa tctggtagcg acactcttga   720
aagacacgtt ataagaaac ggaaagaaga aacctgaaat ttcaagaaac ttgcagagct    780
ttctatctct tatcctcttc tctaccatca tttctcccta taaatacgcc aacgcacata   840 agtgttgca ttcgaagaga gttctagcaa aacaaaacaa aacagagcaa acagagtaag   900
cgaaacgatg aatatctctc aaaacccctag ccctaattttt acgtacttct ccgatgaaaa   960
ctttattaat ccgtttatgg ataacaacga tttctcaaat ttgatgttct ttgacataga   1020
tgaaggaggg aacaatggat taatcgagga agagatctca tctccgacaa gcatcgtttc   1080
gtcggagaca tttaccgggg aaagcggcgg atccggcagc gcaacaacgt tgagtaaaaa   1140
ggaatcaact aatagaggaa gtaaagagag tgatcagacg aaggagacgg gtcatcgagt   1200
tgcatttaga acgagatcga agattgatgt gatggatgat ggttttaaat ggaggaagta   1260
tggcaagaaa tctgtcaaaa acaacattaa caagaggaat tactacaaat gctcaagtga   1320
aggttgctcg gtgaagaaga gggtagagag agatggtgac gatgcagctt atgtaattac   1380
aacatatgaa ggagtccata accatgagag tctctctaat gtctattaca atgaaatggt   1440
tttatcttat gatcatgata actggaacca acactctctt cttcgatctt aa           1492
```

<210> SEQ ID NO 40
<211> LENGTH: 1365

<212> TYPE: DNA
<213> ORGANISM: artificial sequence
<220> FEATURE:
<223> OTHER INFORMATION: SEQ ID NO: 40 Drought inducible promoter-G1274
combination vector, comprises the promoter sequence from the
drought-inducible gene AT1G52690 fused to a G1274 coding sequence
lacking UTR sequences, and the plasmid also carries a kanamycin
resistance marker

<400> SEQUENCE: 40

| | | | | | |
|---|---|---|---|---|---|
| agaaagtgta | tattttagta | aaatcctaaa | tctaagcatt | acactaacac | gtggaaaata | 60 |
| acataccatt | gacgattgac | atggctaatt | ttttgtggag | gtgaatagtt | tgaggattta | 120 |
| ttaccctaac | gttgcttggt | caagaagtga | agtaggatga | caggcaatag | gaagatctta | 180 |
| aaccttttt | tccggtgaca | attatttatg | acttttatt | gttgtcaaaa | aatatattat | 240 |
| cagtaatata | tcaataacga | atacaataaa | aactcatccg | atcgattttc | aagaatttat | 300 |
| agctatatta | aaattacttc | gaatccatgt | aagaattgtg | tattggttct | ttttagaaaa | 360 |
| aagtaaatat | ctatgcagta | atggcggttg | cataatatat | gccttgagta | gatgaatatc | 420 |
| caatatcaag | ataacgtgag | tcaccacgtg | tctaacatct | tccgtagctc | cgttttacc | 480 |
| atgacgtgtc | acatagatat | aggtcatcat | gaaaacgaga | aacctaactt | taacactcgc | 540 |
| acataactcc | aagtttcgaa | acttcgtcac | atcaacctaa | tcggggcacg | tacctacaca | 600 |
| cctgtcgcga | aactgcaaca | cctatcttgt | tctctcgccg | accaagactt | gctataaata | 660 |
| actctgacta | acgagtcgga | gacaactcac | agttccaaac | acacaaaaaa | cacaagatct | 720 |
| aaaaaaaaaa | gcttttatca | tttagaaaaa | tttggtttcg | aatttcttcg | aagagtgaaa | 780 |
| atgaatatct | ctcaaaaccc | tagccctaat | tttacgtact | tctccgatga | aaactttatt | 840 |
| aatccgttta | tggataacaa | cgatttctca | aatttgatgt | tctttgacat | agatgaagga | 900 |
| ggtaacaatg | gattaatcga | ggaagagatc | tcatctccga | caagcatcgt | ttcgtcggag | 960 |
| acatttaccg | gggaaagcgg | cggatccggc | agcgcaacaa | cgttgagtaa | aaaggaatca | 1020 |
| actaatagag | gaagtaaaga | gagtgatcag | acgaaggaga | cgggtcatcg | agttgcattt | 1080 |
| agaacgagat | cgaagattga | tgtgatggat | gatggtttta | aatggaggaa | gtatggcaag | 1140 |
| aaatctgtca | aaaacaacat | taacaagagg | aattactaca | aatgctcaag | tgaaggttgc | 1200 |
| tcggtgaaga | agagggtaga | gagagatggt | gacgatgcag | cttatgtaat | tacaacatat | 1260 |
| gaaggagtcc | ataaccatga | gagtctctct | aatgtctatt | acaatgaaat | ggttttatct | 1320 |
| tatgatcatg | ataactggaa | ccaacactct | cttcttcgat | cttaa | | 1365 |

<210> SEQ ID NO 41
<211> LENGTH: 1032
<212> TYPE: DNA
<213> ORGANISM: artificial sequence
<220> FEATURE:
<223> OTHER INFORMATION: SEQ ID NO: 41 Drought inducible promoter-G1274
combination vector, comprises the promoter sequence from the
drought-inducible gene AT2G37870 fused to a G1274 coding sequence
lacking UTR sequences, and the plasmid also carries a kanamycin
resistance marker

<400> SEQUENCE: 41

| | | | | | |
|---|---|---|---|---|---|
| aaaccatatg | ttgttgtagc | ctactcattt | ctatctgttt | tactacattt | ccgttgttat | 60 |
| atctaataat | aagaattttc | agctcgaatg | ttgaatcctt | atagtgtcta | tattgaaaca | 120 |
| atgaaaacca | aaagtgttct | gaaacaaaga | gagtgcaaaa | agttgttgga | gcctgtttta | 180 |
| tgaaagaaaa | gtaaagagag | aaacaaaaac | aaacacgcaa | gaaatcaaac | gactaaacac | 240 |

```
acaacagatg gtgaaatcta atcaaagta agcataaatc aaatgattac agaatggggg      300
aaaaaattaa acggtataac cgtacacgtc accaaaacac aaccacccca ctaaaacatc      360
ttactagtta ctagtatata agaatcatca acgcactaag taagacactc aacaaaacaa      420
aacaagaagg agaatataag aagaagcatg aatatctctc aaaaccctag ccctaatttt      480
acgtacttct ccgatgaaaa ctttattaat ccgtttatgg ataacaacga tttctcaaat      540
ttgatgttct ttgacataga tgaaggaggt aacaatggat taatcgagga agagatctca      600
tctccgacaa gcatcgtttc gtcggagaca tttaccgggg aaagcggcgg atccggcagc      660
gcaacaacgt tgagtaaaaa ggaatcaact aatagaggaa gtaaagagag tgatcagacg      720
aaggagacgg gtcatcgagt tgcatttaga acgagatcga agattgatgt gatggatgat      780
ggttttaaat ggaggaagta tggcaagaaa tctgtcaaaa acaacattaa caagaggaat      840
tactacaaat gctcaagtga aggttgctcg gtgaagaaga gggtagagag agatggtgac      900
gatgcagctt atgtaattac aacatatgaa ggagtccata accatgagag tctctctaat      960
gtctattaca atgaaatggt tttatcttat gatcatgata actggaacca acactctctt     1020
cttcgatctt aa                                                         1032

<210> SEQ ID NO 42
<211> LENGTH: 1361
<212> TYPE: DNA
<213> ORGANISM: artificial sequence
<220> FEATURE:
<223> OTHER INFORMATION: SEQ ID NO: 42  Drought inducible promoter-G1274
     combination vector, comprises the promoter sequence from the
     drought-inducible gene AT5G43840 (G1947) fused to a G1274 coding
     sequence lacking UTR sequences, and the plasmid also carries a
     kanamycin resistance marker

<400> SEQUENCE: 42
cgattttcga ataaattatt tgagcttttcc aaactgtaat tcaagtatta ttacttatat      60
agtgttagtg tacttcaaaa gttaaagcat aaatttttctt atatttgaaa tgacctcttc     120
tttacaaaat cttcttaaaa ttatgcatta tcaatatatt aattgtatat atatatataa     180
tgtataattc tgcttgtgtc gtgcttaacc gtttgatttg gtgtggttag atctggtttt      240
cccccaaccc aattcaattg aatcaaggat caatcaaatt ttcaaaggat actcttgttc      300
tctacacaaa tctttcaaag ggttccacca aaaatcccat cattctgact tcagaataaa      360
caaacaaacc acgaaacgta tctctatgca ttcactacaa cgtgtcatgg gcgaaaacga      420
agcttataaa tgttggagca tagtcactaa atttataatg attaattaaa ttttagattt      480
tctgatattc atagaagaca aaagaacaca aaagtagcat cttccaatga atgtatgaca      540
ctatgatctc tcatttccat ttatagcaaa tcggctttgt ccacatcaaa gataactaat      600
aaatagactt atccaaaaca ctcaaaagca atacatttct atccaaaaat attaaacccc      660
aaaaatatag acagcataaa agcatcctca agcttcagct attcatcaca actattctct      720
cctctctctt ttttttattaa aaaagctcaa atttatatag gttttttgtt cacaaaatga      780
atatctctca aaaccctagc cctaattttta cgtacttctc cgatgaaaac tttattaatc      840
cgtttatgga taacaacgat ttctcaaatt tgatgttctt tgacatagat gaaggaggta      900
acaatggatt aatcgaggaa gagatctcat ctccgacaag catcgtttcg tcggagacat      960
ttaccgggga aagcggcgga tccggcagcg caacaacgtt gagtaaaaag gaatcaacta     1020
atagaggaag taaagagagt gatcagacga aggagacggg tcatcgagtt gcatttagaa     1080
cgagatcgaa gattgatgtg atggatgatg gttttaaatg gaggaagtat ggcaagaaat     1140
```

```
ctgtcaaaaa caacattaac aagaggaatt actacaaatg ctcaagtgaa ggttgctcgg    1200
tgaagaagag ggtagagaga gatggtgacg atgcagctta tgtaattaca acatatgaag    1260
gagtccataa ccatgagagt ctctctaatg tctattacaa tgaaatggtt ttatctttatg   1320 atcatgataa ctggaaccaa cactctcttc ttcgatctta a                        1361
```

<210> SEQ ID NO 43
<211> LENGTH: 1513
<212> TYPE: DNA
<213> ORGANISM: artificial sequence
<220> FEATURE:
<223> OTHER INFORMATION: SEQ ID NO: 43  P26867 Drought inducible
    promoter-G1274 combination vector, comprises the promoter sequence
    from the drought-inducible gene AT5G66780 fused to a G1274 coding
    sequence lacking UTR sequences, and the plasmid also carries a
    kanamycin resistance marker

<400> SEQUENCE: 43

```
tagtcttgtt gttttctcat tagataattt aaactggttt gcttctttat ttttggttgg     60
ataaagtgac cggttctggt catctgtttg agatgtaatt actatttcat aaaattagga    120
agttgaaagc caaatatatt tgtaactact cttttatttg taattttgct caaaaaagtg    180
atgaaatgta gttttgatat atgaatatct accattatac ataagtatat ctgaacatgg    240
tacaacttat gaaagctaaa tgtcaatact tgcaaagata taacaaatac aagttacatg    300
aataagagat gtgtgttgaa tttataagtg tcattttctt ttcactttaa aacaaacttc    360
atcttctttt gtttcttatg tgtcaaagtt gccacagttg ctctatttga gtctttcagt    420
gtcagtctca gtcactgtac tgattttact ttttttttgtt gagtgtgcca atgatgacat    480
cactcccacg tcctccatcc gtcttctttt aacggtcacg tggctcccac cctctttttct   540 cgatgtcttt accgacttgt tctagcccaa cttacttggg ccatttagat ttttttggtgg   600 cccaagttgc taaaagagga tttatcatag aaatctgaac ccgttgcagc gctcaacaca    660
tgtcacagtc ctgacaaaca cgtattcaaa tccttgttaa gtcccgccac ctgtcaccag    720
agcaccacga ggcaaactct gatcaggaca ccgtcgtact attatgtcgg aagacaggaa    780
agcttaatta agcttaaacc tgacgtattt aacttcgtta actctacctt actaaagggt    840
tttaatttaa aacttatcat ctcctcgtaa gaataaaaac tacttactct ataaatttaa    900
gcttcaagaa acctccaaaa gcagagaaat gaatatctct caaaaccta gccctaattt     960 tacgtacttc tccgatgaaa actttattaa tccgtttatg gataacaacg atttctcaaa   1020
tttgatgttc tttgacatag atgaaggagg taacaatgga ttaatcgagg aagagatctc   1080
atctccgaca agcatcgttt cgtcggagac atttaccggg gaaagcggcg gatccggcag   1140
cgcaacaact tgagtaaaaa ggaatcaac taatagagga agtaaagaga gtgatcagac    1200
gaaggagacg ggtcatcgag ttgcatttag aacgagatcg aagattgatg tgatggatga   1260
tggttttaaa tggaggaagt atggcaagaa atctgtcaaa aacaacatta acaagaggaa   1320
ttactacaaa tgctcaagtg aaggttgctc ggtgaagaag agggtagaga gagatggtga   1380
cgatgcagct tatgtaatta caacatatga aggagtccat aaccatgaga gtctctctaa   1440
tgtctattac aatgaaatgg ttttatctta tgatcatgat aactggaacc aacactctct   1500
tcttcgatct taa                                                      1513
```

<210> SEQ ID NO 44
<211> LENGTH: 1045
<212> TYPE: DNA

<213> ORGANISM: artificial sequence
<220> FEATURE:
<223> OTHER INFORMATION: SEQ ID NO: 44   P26866 Drought inducible
    promoter-G1274 combination vector, comprises the promoter sequence
    from the drought-inducible gene AT3G17520 fused to a G1274 coding
    sequence lacking UTR sequences, and the plasmid also carries a
    kanamycin resistance marker

<400> SEQUENCE: 44

```
gggtttttact tacaataagc ccttactatt cattgaaaag ctcactaaac ttgtttatga      60
aaagcccact ggttattgta tacaagccca ttagcttcac agatgtgttt cagttgaagc     120
ctctctttgt ttttgcgagt cggttttccg caaaaagcaa tcgcttgcct cgttgtttgt     180
gtaacacgtg tcaagaacca cttaacacga atccaaaatc gagaagccaa agaagctgg     240 tactcgccac gtacttagcc acgcgtccta aacctatctc tttttcaact aatacataac     300
agagaagcaa tcacagcacc attcctcgga gaacacatca cagtaaacag aggtttttt     360 cttcttctga aacttgatat aagttatata accatataat attttgtgtt cgattagtgt     420
aacaaaaatg gggttagaga ggaaagtgta cggtttggtt atgaatatct ctcaaaaccc     480
tagccctaat tttacgtact ctccgatga aactttatt aatccgttta tggataacaa      540
cgatttctca aatttgatgt tctttgacat agatgaagga ggtaacaatg gattaatcga     600
ggaagagatc tcatctccga caagcatcgt ttcgtcggag acatttaccg gggaaagcgg     660
cggatccggc agcgcaacaa cgttgagtaa aaaggaatca actaatagag gaagtaaaga     720
gagtgatcag acgaaggaga cgggtcatcg agttgcattt agaacgagat cgaagattga     780
tgtgatggat gatggtttta aatggaggaa gtatggcaag aaatctgtca aaacaacat     840 taacaagagg aattactaca aatgctcaag tgaaggttgc tcggtgaaga agagggtaga     900
gagagatggt gacgatgcag cttatgtaat tacaacatat gaaggagtcc ataaccatga     960
gagtctctct aatgtctatt acaatgaaat ggttttatct tatgatcatg ataactggaa    1020
ccaacactct cttcttcgat cttaa                                           1045
```

<210> SEQ ID NO 45
<211> LENGTH: 1521
<212> TYPE: DNA
<213> ORGANISM: artificial sequence
<220> FEATURE:
<223> OTHER INFORMATION: SEQ ID NO: 45   P26865 Drought inducible
    promoter-G1274 combination vector, comprises the promoter sequence
    from the drought-inducible gene AT4G09600 fused to a G1274 coding
    sequence lacking UTR sequences, and the plasmid also carries a
    kanamycin resistance marker

<400> SEQUENCE: 45

```
gttaaatcct cactaggatc tctctttata ttaatggtta aaaacatatg catgttttgt      60 gttttttgcat cttctttttc atagacaaaa gcaagatgag tcttagaagg acatcaatgt    120
catagacatg gctttagtat cttttgagtg tgctttaaat gatgatgatt taccctgaac    180
ctgaaatttt acctattaat taatttaagt gtgcgttaaa ccataaacca tatactctga    240
acctgaaatt ggttctaaag cacaacctaa acttgagatt ggagaatgct ttaaaaggaa    300
aaaaaaatca aaggaaacca ttaatgagcc atcaaaaaat attcactaat atgacaagat    360
gcattgttta ttttctttt cagaatcctc agaaactacc actaaactcc tcaaggaaca    420
aaaccatatc atgaattagg ctggcaattt aactctgaga cgtctttctt gtatagaaa    480 taaacatac gcgtgtaaaa gaaaacgcgt gaatcgaatg atgagtgtta acgttcgatc    540
gagatgccac caaatctttt cattaaaatg aattgtggag gacataccac ttttaacgag    600
```

```
gtcatttcca ctgggtgaca tgtggactct actttgggtg gcatgttcat atctttccac      660
atcaccatgt aaacgtgaaa acacccacca cactcactta catctcaaac acatgtcttc      720
attatcgtac gtagctccaa aaaaaaaaat gaaaactagg tttagtgatt ctatttcgca      780
atgtataata tacaacttgt aaaaataaaa tatttgaata agcattataa ataaacccaa      840
agaggtgtta gatttatata cttaattgta gctactaaat agagaatcag agagaatagt      900
tttatatctt gcacgaaact gcatgctttt tgagacatga atatctctca aaaccctagc      960
cctaatttta cgtacttctc cgatgaaaac tttattaatc cgtttatgga taacaacgat     1020
ttctcaaatt tgatgttctt tgacatagat gaaggaggta acaatggatt aatcgaggaa     1080
gagatctcat ctccgacaag catcgtttcg tcggagacat ttaccgggga aagcggcgga     1140
tccggcagcg caacaacgtt gagtaaaaag gaatcaacta atagaggaag taaagagagt     1200
gatcagacga aggagacggg tcatcgagtt gcatttagaa cgagatcgaa gattgatgtg     1260
atggatgatg gttttaaatg gaggaagtat ggcaagaaat ctgtcaaaaa caacattaac     1320
aagaggaatt actacaaatg ctcaagtgaa ggttgctcgg tgaagaagag ggtagagaga     1380
gatggtgacg atgcagctta tgtaattaca acatatgaag gagtccataa ccatgagagt     1440
ctctctaatg tctattacaa tgaaatggtt ttatcttatg atcatgataa ctggaaccaa     1500
cactctcttc ttcgatctta a                                              1521
```

<210> SEQ ID NO 46
<211> LENGTH: 1186
<212> TYPE: DNA
<213> ORGANISM: artificial sequence
<220> FEATURE:
<223> OTHER INFORMATION: SEQ ID NO: 46  Drought inducible promoter-G1792
      combination vector, comprises the promoter sequence from the
      drought-inducible gene AT1G16850 fused to a G1792 coding sequence
      lacking UTR sequences, and the plasmid also carries a kanamycin
      resistance marker

<400> SEQUENCE: 46

```
attgggtacg attttcatag gtctttcctc acgccagaag tgttgtttta ttttgttgat       60
tgagttatta attattggaa gcttttcttt caagcaaagt aaaatgcgta ataatgatta      120
gtcacatcca atggttagtc agtctattac accgttaatc aagctctggt catataattt      180
ttttattttt ggaactaaca cttattagtt taggtttcca tcacctattt aattcgtaat      240
tcttatacat gcatataata gagatacata tatacaaatt tatgatcatt tttgcacaac      300
atgtgatctc attcattagt atgcattatg cgaaaacctc gacgcgcaaa agacacgtaa      360
tagctaataa tgttactcat ttataatgat tgaagcaaga cgaaaacaac aacatatata      420
tcaaattgta aactagatat ttcttaaaag tgaaaaaaaa caaagaaata taaggacaa       480 ttttgagtca gtctcttaat attaaaacat atatacataa ataagcacaa acgtggttac      540
ctgtcttcat gcaatgtgga ctttagttta tctaatcaaa atcaaaataa aaggtgtaat      600
agttctcgtc atttttcaaa ttttaaaaat cagaaccaag tgattttttgt ttgagtattg      660 atccattgtt taaacaattt aacacagtat atacgtctct tgagatgttg acatgatgat      720
aaaatacgag atcgtctctt ggttttcgaa ttttgaactt taatagatgg agagctcaaa      780
caggagcagc aacaaccaat cacaagatga caagcaagct cgtttccggg gagttcgaag      840
aaggccttgg ggaaagtttg cagcagagat tcgagacccg tcgagaaacg gtgcccgtct      900
ttggctcggg acatttgaga ccgctgagga ggcagcaagg gcttatgacc gagcagcctt      960
```

```
taaccttagg ggtcatctcg ctatactcaa cttccctaat gagtattatc cacgtatgga    1020
cgactactcg cttcgccctc cttatgcttc ttcttcttcg tcgtcgtcat cgggttcaac    1080
ttctactaat gtgagtcgac aaaaccaaag agaagttttc gagtttgagt atttggacga    1140
taaggttctt gaagaacttc ttgattcaga agaaaggaag agataa                   1186
```

<210> SEQ ID NO 47
<211> LENGTH: 1025
<212> TYPE: DNA
<213> ORGANISM: artificial sequence
<220> FEATURE:
<223> OTHER INFORMATION: SEQ ID NO: 47 Drought inducible promoter-G1792
combination vector, comprises the promoter sequence from the
drought-inducible gene AT5G52300 fused to a G1792 coding sequence
lacking UTR sequences, and the plasmid also carries a kanamycin
resistance marker

<400> SEQUENCE: 47

```
tgatgatgat gatgaagaag agaacgaatt tgaaattgg cggttttgaa ttttaagaa      60 attaaaaaat atcccccgtc gatttcaaga gggagatgga gataccaaag caactctcgc   120
cacttgtcgt cttttaattt taattgagta cgttatgccg ttttaaatgt tcaaaacagc   180
acacagttga tagctgaatt gatttttttct tttgccgttt tgttatattt aaacaacaca   240
cagtgcattt gccaaataac tacatgatgg gccaataaac gtggaccgac taaaactaaa   300
taatagaaga tacatcgata ggcttctcta aagatcggat aaaagataat gtcgcatagc   360
cacgtagaga gcaactggct gagacgtggc aggacgaaac ggacgcatcg tacgtgtcag   420
aatcctacag aagtaaagag acagaagcca gagagaggtg gttcggccat atgtcatcgt   480
tctctctata aactttatgg aactttgttc tgatttttctc agagacacga aaagaaagaa   540
aacaacacta gaacaaagag ggtttgattg attcacttga aaaagagaaa acacagcttt   600
ggaaaatgga gagctcaaac aggagcagca acaaccaatc acaagatgac aagcaagctc   660
gtttccgggg agttcgaaga aggccttggg gaaagtttgc agcagagatt cgagacccgt   720
cgagaaacgg tgcccgtctt tggctcggga catttgagac cgctgaggag gcagcaaggg   780
cttatgaccg agcagccttt aaccttaggg gtcatctcgc tatactcaac ttccctaatg   840
agtattatcc acgtatggac gactactcgc ttcgccctcc ttatgcttct tcttcttcgt   900
cgtcgtcatc gggttcaact tctactaatg tgagtcgaca aaaccaaaga gaagttttcg   960
agtttgagta tttggacgat aaggttcttg aagaacttct tgattcagaa gaaaggaaga  1020
gataa                                                              1025
```

<210> SEQ ID NO 48
<211> LENGTH: 1327
<212> TYPE: DNA
<213> ORGANISM: artificial sequence
<220> FEATURE:
<223> OTHER INFORMATION: SEQ ID NO: 48 Drought inducible promoter-G1792
combination vector, comprises the promoter sequence from the
drought-inducible gene AT3G46230 fused to a G1792 coding sequence
lacking UTR sequences, and the plasmid also carries a kanamycin
resistance marker

<400> SEQUENCE: 48

```
ttatttattc tcaattttcc catacgaatt ttttgtcttt atatttatca caaaaaaga     60 gtttgctctt taaaaaacta tactaatgta attttttttat tttattttct ctatcttaat   120
cggatattaa tccgactctt cttcttccca aaaattaata ttagtttcaa atccaaagca   180
acccacctca ttcaactttc cttcgatttt cttcaaattt ccagtttcca cttgctttca   240
```

```
ttgcttcttt cccgccgttt ctagatcttc aatcgagaaa gggatttgca acttttcaca      300
caaaaatctt agattaattg ttattaataa cttgttcatc aaaccactaa aaatcccgtg      360
tcatcttcga cttcttggtt aaaattcaat aaagagtgta acttttcatt gctataactt      420
aataatttgt ttgtgagaag agaactctag tcttacaggg accaacacca acaatcaaaa      480
tttagataat gaagaatagt tgctgatgca tgattaagat tgaatttatc aacaaaagat      540
aagtgttcat tatacaacac gtgattaatt gcatggtgta ttaaggccca ttaacgaagt      600
ccatggtaaa atgaaacggc atggcgttca ctaccccacc taatgaactg catgtcgtct      660
caaccatcaa catagaagct tcttgaagcc acctgagaaa tctggtagcg acactcttga      720 aagcacgtt ataagaaac ggaagaaga aacctgaaat ttcaagaaac ttgcagagct         780
ttctatctct tatcctcttc tctaccatca tttctcccta taaatacgcc aacgcacata      840
agtgtttgca ttcgaagaga gttctagcaa acaaaacaa acagagcaa acagagtaag        900 cgaaacgatg gagagctcaa acaggagcag caacaaccaa tcacaagatg acaagcaagc      960
tcgtttccgg ggagttcgaa gaaggccttg gggaaagttt gcagcagaga ttcgagaccc     1020
gtcgagaaac ggtgcccgtc tttggctcgg acatttgag accgctgagg aggcagcaag       1080
ggcttatgac cgagcagcct ttaaccttag gggtcatctc gctatactca acttccctaa     1140
tgagtattat ccacgtatgg acgactactc gcttcgccct ccttatgctt cttcttcttc     1200
gtcgtcgtca tcgggttcaa cttctactaa tgtgagtcga caaaaccaaa gagaagtttt     1260
cgagtttgag tatttggacg ataaggttct tgaagaactt cttgattcag aagaaggaa      1320 gagataa                                                               1327
```

<210> SEQ ID NO 49
<211> LENGTH: 1200
<212> TYPE: DNA
<213> ORGANISM: artificial sequence
<220> FEATURE:
<223> OTHER INFORMATION: SEQ ID NO: 49 Drought inducible promoter-G1792 combination vector, comprises the promoter sequence from the drought-inducible gene AT1G52690 fused to a G1792 coding sequence lacking UTR sequences, and the plasmid also carries a kanamycin resistance marker

<400> SEQUENCE: 49

```
agaaagtgta tattttagta aaatcctaaa tctaagcatt acactaacac gtggaaaata       60
acataccatt gacgattgac atggctaatt ttttgtggag gtgaatagtt tgaggattta      120
ttaccctaac gttgcttggt caagaagtga agtaggatga caggcaatag gaagatctta      180
aacctttttt tccggtgaca attatttatg acttttttatt gttgtcaaaa aatatattat    240
cagtaatata tcaataacga atacaataaa aactcatccg atcgattttc aagaatttat     300
agctatatta aaattacttc gaatccatgt aagaattgtg tattggttct ttttagaaaa     360
aagtaaatat ctatgcagta atggcggttg cataatatat gccttgagta gatgaatatc     420
caatatcaag ataacgtgag tcaccacgtg tctaacatct tccgtagctc cgttttttacc    480 atgacgtgtc acatagatat aggtcatcat gaaaacgaga aacctaactt taacactcgc     540
acataactcc aagtttcgaa acttcgtcac atcaacctaa tcggggcacg tacctacaca     600
cctgtcgcga aactgcaaca cctatcttgt tctctcgccg accaagactt gctataaata     660
actctgacta acgagtcgga gacaactcac agttccaaac acacaaaaaa cacaagatct     720
aaaaaaaaaa gctttatca tttagaaaaa tttggtttcg aatttcttcg aagagtgaaa      780
```

```
atggagagct caaacaggag cagcaacaac caatcacaag atgacaagca agctcgtttc    840
cggggagttc gaagaaggcc ttggggaaag tttgcagcag agattcgaga cccgtcgaga    900
aacggtgccc gtctttggct cgggacattt gagaccgctg aggaggcagc aagggcttat    960
gaccgagcag cctttaacct tagggtcat ctcgctatac tcaacttccc taatgagtat   1020
tatccacgta tggacgacta ctcgcttcgc cctccttatg cttcttcttc ttcgtcgtcg   1080
tcatcgggtt caacttctac taatgtgagt cgacaaaacc aaagagaagt tttcgagttt   1140
gagtatttgg acgataaggt tcttgaagaa cttcttgatt cagaagaaag gaagagataa   1200
```

<210> SEQ ID NO 50
<211> LENGTH: 867
<212> TYPE: DNA
<213> ORGANISM: artificial sequence
<220> FEATURE:
<223> OTHER INFORMATION: SEQ ID NO: 50  Drought inducible promoter-G1792 combination vector, comprises the promoter sequence from the drought-inducible gene AT2G37870 fused to a G1792 coding sequence lacking UTR sequences, and the plasmid also carries a kanamycin resistance marker

<400> SEQUENCE: 50

```
aaaccatatg ttgttgtagc ctactcattt ctatctgttt tactacattt ccgttgttat     60
atctaataat aagaattttc agctcgaatg ttgaatcctt atagtgtcta tattgaaaca    120
atgaaaacca aaagtgttct gaaacaaaga gagtgcaaaa agttgttgga gcctgtttta    180
tgaaagaaaa gtaagagag aaacaaaaac aaacacgcaa gaaatcaaac gactaaacac    240
acaacagatg gtgaaatcta aatcaaagta agcataaatc aaatgattac agaatggggg    300
aaaaaattaa acggtataac cgtacacgtc accaaaacac aaccaccccca ctaaaacatc    360 ttactagtta ctagtatata agaatcatca acgcactaag taagacactc aacaaaacaa    420
aacaagaagg agaatataag aagaagcatg gagagctcaa acaggagcag caacaaccaa    480
tcacaagatg acaagcaagc tcgtttccgg ggagttcgaa gaaggccttg gggaaagttt    540
gcagcagaga ttcgagaccc gtcgagaaac ggtgcccgtc tttggctcgg gacatttgag    600
accgctgagg aggcagcaag ggcttatgac cgagcagcct ttaaccttag ggtcatctc    660 gctatactca acttccctaa tgagtattat ccacgtatgg acgactactc gcttcgccct    720
ccttatgctt cttcttcttc gtcgtcgtca tcgggttcaa cttctactaa tgtgagtcga    780
caaaaccaaa gagaagtttt cgagtttgag tatttggacg ataaggttct tgaagaactt    840
cttgattcag aagaaggaa gagataa                                         867
```

<210> SEQ ID NO 51
<211> LENGTH: 1196
<212> TYPE: DNA
<213> ORGANISM: artificial sequence
<220> FEATURE:
<223> OTHER INFORMATION: SEQ ID NO: 51 P26706 Drought inducible promoter-G1792 combination vector, comprises the promoter sequence from the drought-inducible gene AT5G43840 (G1947) fused to a G1792 coding sequence lacking UTR sequences, and the plasmid also carries a kanamycin resistance marker

<400> SEQUENCE: 51

```
cgattttcga ataaattatt tgagctttcc aaactgtaat tcaagtatta ttacttatat     60
agtgttagtg tacttcaaaa gttaaagcat aaatttctt atatttgaaa tgacctcttc    120
tttacaaaat cttcttaaaa ttatgcatta tcaatatatt aattgtatat atatataaa    180 tgtataattc tgcttgtgtc gtgcttaacc gtttgatttg gtgtggttag atctggtttt    240
```

-continued

```
cccccaaccc aattcaattg aatcaaggat caatcaaatt ttcaaaggat actcttgttc        300
tctacacaaa tctttcaaag ggttccacca aaaatcccat cattctgact tcagaataaa        360
caaacaaacc acgaaacgta tctctatgca ttcactacaa cgtgtcatgg gcgaaaacga        420
agcttataaa tgttggagca tagtcactaa atttataatg attaattaaa ttttagattt        480
tctgatattc atagaagaca aaagaacaca aaagtagcat cttccaatga atgtatgaca        540
ctatgatctc tcatttccat ttatagcaaa tcggctttgt ccacatcaaa gataactaat        600
aaatagactt atccaaaaca ctcaaaagca atacatttct atccaaaaat attaaacccc        660
aaaaatatag acagcataaa agcatcctca agcttcagct attcatcaca actattctct        720
cctctctctt tttttattaa aaaagctcaa atttatatag gttttttgtt cacaaaatgg        780
agagctcaaa caggagcagc aacaaccaat cacaagatga caagcaagct cgtttccggg        840
gagttcgaag aaggccttgg ggaaagtttg cagcagagat tcgagacccg tcgagaaacg        900
gtgcccgtct ttggctcggg acatttgaga ccgctgagga ggcagcaagg gcttatgacc        960
gagcagcctt taaccttagg ggtcatctcg ctatactcaa cttccctaat gagtattatc       1020
cacgtatgga cgactactcg cttcgccctc cttatgcttc ttcttcttcg tcgtcgtcat       1080
cgggttcaac ttctactaat gtgagtcgac aaaaccaaag agaagttttc gagtttgagt       1140
atttggacga taaggttctt gaagaacttc ttgattcaga agaaaggaag agataa          1196
```

<210> SEQ ID NO 52
<211> LENGTH: 1348
<212> TYPE: DNA
<213> ORGANISM: artificial sequence
<220> FEATURE:
<223> OTHER INFORMATION: SEQ ID NO: 52  P26691 Drought inducible
      promoter-G1792 combination vector, comprises the promoter sequence
      from the drought-inducible gene AT5G66780 fused to a G1792 coding
      sequence lacking UTR sequences, and the plasmid also carries a
      kanamycin resistance marker

<400> SEQUENCE: 52

```
tagtcttgtt gttttctcat tagataattt aaactggttt gcttctttat ttttggttgg         60
ataaagtgac cggttctggt catctgtttg agatgtaatt actatttcat aaaattagga        120
agttgaaagc caaatatatt tgtaactact cttttatttg taattttgct caaaaaagtg        180
atgaaatgta gttttgatat atgaatatct accattatac ataagtatat ctgaacatgg        240
tacaacttat gaaagctaaa tgtcaatact tgcaaagata taacaaatac aagttacatg        300
aataagagat gtgtgttgaa tttataagtg tcatttcttt ttcactttaa aacaaacttc        360
atcttctttt gtttcttatg tgtcaaagtt gccacagttg ctctatttga gtctttcagt        420
gtcagtctca gtcactgtac tgattttact tttttttgtt gagtgtgcca atgatgacat        480
cactcccacg tcctccatcc gtcttctttt aacggtcacg tggctcccac cctctttttct       540 cgatgtcttt accgacttgt tctagcccaa cttacttggg ccatttagat tttttggtgg        600
cccaagttgc taaaagagga tttatcatag aaatctgaac ccgttgcagc gctcaacaca        660
tgtcacagtc ctgacaaaca cgtattcaaa tccttgttaa gtcccgccac ctgtcaccag        720
agcaccacga ggcaaactct gatcaggaca ccgtcgtact attatgtcgg aagacaggaa        780
agcttaatta agcttaaacc tgacgtattt aacttcgtta actctacctt actaaagggt        840
tttaatttaa aacttatcat ctcctcgtaa gaataaaaac tacttactct ataaatttaa        900
gcttcaagaa acctccaaaa gcagagaaat ggagagctca acaggagca gcaacaacca        960
```

```
atcacaagat gacaagcaag ctcgtttccg gggagttcga agaaggcctt ggggaaagtt      1020
tgcagcagag attcgagacc cgtcgagaaa cggtgcccgt cttggctcg gacatttga       1080 gaccgctgag gaggcagcaa gggcttatga ccgagcagcc tttaacctta ggggtcatct      1140
cgctatactc aacttcccta atgagtatta tccacgtatg gacgactact cgcttcgccc      1200
tccttatgct tcttcttctt cgtcgtcgtc atcgggttca acttctacta atgtgagtcg      1260
acaaaaccaa agagaagttt tcgagtttga gtatttggac gataaggttc ttgaagaact      1320
tcttgattca gaagaaagga agagataa                                          1348
```

<210> SEQ ID NO 53
<211> LENGTH: 880
<212> TYPE: DNA
<213> ORGANISM: artificial sequence
<220> FEATURE:
<223> OTHER INFORMATION: SEQ ID NO: 53  P26690 Drought inducible
    promoter-G1792 combination vector, comprises the promoter sequence
    from the drought-inducible gene AT3G17520 fused to a G1792 coding
    sequence lacking UTR sequences, and the plasmid also carries a
    kanamycin resistance marker

<400> SEQUENCE: 53

```
gggtttact tacaataagc ccttactatt cattgaaaag ctcactaaac ttgtttatga       60
aaagcccact ggttattgta tacaagccca ttagcttcac agatgtgttt cagttgaagc      120
ctctctttgt ttttgcgagt cggttttccg caaaaagcaa tcgcttgcct cgttgtttgt     180
gtaacacgtg tcaagaacca cttaacacga atccaaaatc gagaagccaa agaagctgg      240 tactcgccac gtactagcc acgcgtccta aacctatctc ttttcaact aatacataac       300 agagaagcaa tcacagcacc attcctcgga gaacacatca cagtaaacag aggtttttt     360 cttcttctga aacttgatat aagttatata accatataat attttgtgtt cgattagtgt     420
aacaaaaatg gggttagaga ggaaagtgta cggtttggtt atggagagct caaacaggag     480
cagcaacaac caatcacaag atgacaagca agctcgtttc cggggagttc gaagaaggcc     540
ttggggaaag tttgcagcag agattcgaga cccgtcgaga aacggtgccc gtctttggct     600
cgggacattt gagaccgctg aggaggcagc aagggcttat gaccgagcag cctttaacct    660
taggggtcat ctcgctatac tcaacttccc taatgagtat tatccacgta tggacgacta     720
ctcgcttcgc cctccttatg cttcttcttc ttcgtcgtcg tcatcgggtt caacttctac     780
taatgtgagt cgacaaaacc aaagagaagt tttcgagttt gagtatttgg acgataaggt     840
tcttgaagaa cttcttgatt cagaagaaag gaagagataa                            880
```

<210> SEQ ID NO 54
<211> LENGTH: 1356
<212> TYPE: DNA
<213> ORGANISM: artificial sequence
<220> FEATURE:
<223> OTHER INFORMATION: SEQ ID NO: 54  P26689 Drought inducible
    promoter-G1792 combination vector, comprises the promoter sequence
    from the drought-inducible gene AT4G09600 fused to a G1792 coding
    sequence lacking UTR sequences, and the plasmid also carries a
    kanamycin resistance marker

<400> SEQUENCE: 54

```
gttaaatcct cactaggatc tctctttata ttaatggtta aaaacatatg catgttttgt      60 gttttttgcat cttctttttc atagacaaaa gcaagatgag tcttagaagg acatcaatgt    120
catagacatg gctttagtat cttttgagtg tgctttaaat gatgatgatt taccctgaac     180
ctgaaatttt acctattaat taatttaagt gtgcgttaaa ccataaacca tatactctga     240
```

-continued

```
acctgaaatt ggttctaaag cacaacctaa acttgagatt ggagaatgct ttaaaaggaa      300
aaaaaaatca aaggaaacca ttaatgagcc atcaaaaaat attcactaat atgacaagat      360
gcattgttta ttttctttt cagaatcctc agaaactacc actaaactcc tcaaggaaca      420
aaaccatatc atgaattagg ctggcaattt aactctgaga cgtctttctt gtatagagaa      480
taaaacatac gcgtgtaaaa gaaaacgcgt gaatcgaatg atgagtgtta acgttcgatc      540
gagatgccac caaatctttt cattaaaatg aattgtggag acataccac ttttaacgag       600 gtcatttcca ctgggtgaca tgtggactct actttgggtg gcatgttcat atctttccac      660
atcaccatgt aaacgtgaaa acacccacca cactcactta catctcaaac acatgtcttc      720
attatcgtac gtagctccaa aaaaaaaat gaaaactagg tttagtgatt ctatttcgca      780
atgtataata tacaacttgt aaaaataaaa tatttgaata agcattataa ataaacccaa      840
agaggtgtta gatttatata cttaattgta gctactaaat agagaatcag agagaatagt      900
tttatatctt gcacgaaact gcatgctttt tgagacatgg agagctcaaa caggagcagc      960
aacaaccaat cacaagatga caagcaagct cgtttccggg gagttcgaag aaggccttgg     1020
ggaaagtttg cagcagagat tcgagacccg tcgagaaacg gtgcccgtct ttggctcggg     1080
acatttgaga ccgctgagga ggcagcaagg gcttatgacc gagcagcctt taaccttagg     1140
ggtcatctcg ctatactcaa cttccctaat gagtattatc cacgtatgga cgactactcg     1200
cttcgccctc cttatgcttc ttcttcttcg tcgtcgtcat cgggttcaac ttctactaat     1260
gtgagtcgac aaaaccaaag agaagttttc gagtttgagt atttggacga taaggttctt     1320
gaagaacttc ttgattcaga agaaaggaag agataa                               1356
```

<210> SEQ ID NO 55
<211> LENGTH: 832
<212> TYPE: DNA
<213> ORGANISM: Arabidopsis thaliana
<220> FEATURE:
<223> OTHER INFORMATION: SEQ ID NO: 55  G481 cDNA (start codon begins at
       nucleotide 103)

<400> SEQUENCE: 55

```
gagcgtttcg tagaaaaatt cgatttctct aaagccctaa aactaaaacg actatcccca       60
attccaagtt ctagggtttc catcttcccc aatctagtat aaatggcgga tacgccttcg      120
agcccagctg gagatggcgg agaaagcggc ggttccgtta gggagcagga tcgataccct      180
cctatagcta atatcagcag gatcatgaag aaagcgttgc ctcctaatgg taagattgga      240
aaagatgcta aggatacagt tcaggaatgc gtctctgagt tcatcagctt catcactagc      300
gaggccagtg ataagtgtca aaagagaaa ggaaaactg tgaatggtga tgatttgttg       360
tgggcaatgg caacattagg atttgaggat tacctggaac ctctaaagat ataccctagcg     420 aggtacaggg agttggaggg tgataataag ggatcaggaa agagtggaga tggatcaaat      480
agagatgctg gtggcggtgt ttctggtgaa gaaatgccga gctggtaaaa gaagttgcaa     540
gtagtgatta agaacaatcg ccaaatgatc aagggaaatt agagatcagt gagttgttta      600
tagttgagct gatcgacaac tatttcgggt ttactctcaa tttcggttat gttagtttga     660
acgtttggtt tattgtttcc ggtttagttg gttgtattta agatttctc tgttagatgt       720 tgagaacact tgaatgaagg aaaaatttgt ccacatcctg ttgttatttt cgattcactt      780
tcggaatttc atagctaatt tattctcatt taataccaaa tccttaaatt aa              832
```

<210> SEQ ID NO 56
<211> LENGTH: 144
<212> TYPE: PRT
<213> ORGANISM: Arabidopsis thaliana
<220> FEATURE:
<223> OTHER INFORMATION: SEQ ID NO: 56  G481 polypeptide

<400> SEQUENCE: 56

```
Met Asp Tyr Arg Glu Ser Thr Gly Glu Ser Gln Ser Lys Tyr Lys Gly
1               5                   10                  15

Ile Arg Arg Arg Lys Trp Gly Lys Trp Val Ser Glu Ile Arg Val Pro
            20                  25                  30

Gly Thr Arg Asp Arg Leu Trp Leu Gly Ser Phe Ser Thr Ala Glu Gly
        35                  40                  45

Ala Ala Val Ala His Asp Val Ala Phe Phe Cys Leu His Gln Pro Asp
    50                  55                  60

Ser Leu Glu Ser Leu Asn Phe Pro His Leu Leu Asn Pro Ser Leu Val
65                  70                  75                  80

Ser Arg Thr Ser Pro Arg Ser Ile Gln Gln Ala Ser Asn Ala Gly
                85                  90                  95

Met Ala Ile Asp Ala Gly Ile Val His Ser Thr Ser Val Asn Ser Gly
            100                 105                 110

Cys Gly Asp Thr Thr Tyr Tyr Glu Asn Gly Ala Asp Gln Val Glu
        115                 120                 125

Pro Leu Asn Ile Ser Val Tyr Asp Tyr Leu Gly Gly His Asp His Val
    130                 135                 140
```

<210> SEQ ID NO 57
<211> LENGTH: 1327
<212> TYPE: DNA
<213> ORGANISM: Arabidopsis thaliana
<220> FEATURE:
<223> OTHER INFORMATION: SEQ ID NO: 57  G1073 cDNA (start codon begins
      at nucleotide 234, or 321 for truncated polypeptide)

<400> SEQUENCE: 57

```
tcaccgaccc agctctttca catatgtaga cctctctctc tctaattatt cagtaaggtt     60
ttgttctctc ttgtcgtctt cttgttttgt ccgtagcatt attaataatc aaactcagtc    120
tctgaaatac tctcagtgac aaaccacttc tgtcgacttt tgtctttgtc tctcactagc    180
tataaccaaa aaaatccaaa aacccaaacc acagtttctt gttttttgtta tcaatgtcta    240
gttatatgca ccctcttcta gggcaagaac tgcatctaca gagacctgaa gattccagaa    300
ccccacctga tcaaaataac atggaactta acagatctga agcagacgaa gcaaaggccg    360
agaccactcc caccggtgga gccaccagct cagccacagc ctctggctct tcctccggac    420
gtcgtccacg tggtcgtcct gcaggttcca aaaacaaacc caaacctccg acgattataa    480
ctagagatag tcctaacgtc cttagatcac acgttcttga agtcacctcc ggttcggaca    540
tatccgaggc agtctccacc tacgccactc gtcgcggctg cggcgtttgc attataagcg    600
gcacgggtgc ggtcactaac gtcacgatac ggcaacctgc ggctccggct ggtggaggtg    660
tgattacccct gcatggtcgg tttgacattt tgtctttgac cggtactgcg cttccaccgc    720
ctgcaccacc gggagcagga ggtttgacgg tgtatctagc cggaggtcaa ggacaagttg    780
taggagggaa tgtggctggt tcgttaattg cttcgggacc ggtagtgttg atggctgctt    840
cttttgcaaa cgcagtttat gataggttac cgattgaaga ggaagaaacc ccaccgccga    900
gaaccaccgg ggtgcagcag cagcagccgg aggcgtctca gtcgtcggag gttacgggga    960
```

```
gtggggccca ggcgtgtgag tcaaacctcc aaggtggaaa tggtggagga ggtgttgctt    1020
tctacaatct tggaatgaat atgaacaatt ttcaattctc cggggagat atttacggta     1080 tgagcggcgg tagcggagga ggtggtggcg gtgcgactag acccgcgttt tagagtttta    1140 gcgtttggt gacacctttt gttgcgtttg cgtgtttgac ctcaaactac taggctacta    1200
gctatagcgg ttgcgaaatg cgaatattag gttttattta tttattttt gtttctctta    1260 aaacttggtg tgtgaaaaaa gaaaacgaac gcttaaattt ccttttctg tttgttttta    1320 tgaggcc                                                              1327
```

<210> SEQ ID NO 58
<211> LENGTH: 299
<212> TYPE: PRT
<213> ORGANISM: Arabidopsis thaliana
<220> FEATURE:
<223> OTHER INFORMATION: SEQ ID NO: 58   G1073 polypeptide

<400> SEQUENCE: 58

```
Met Ser Ser Tyr Met His Pro Leu Leu Gly Gln Glu Leu His Leu Gln
1               5                   10                  15

Arg Pro Glu Asp Ser Arg Thr Pro Pro Asp Gln Asn Asn Met Glu Leu
            20                  25                  30

Asn Arg Ser Glu Ala Asp Glu Ala Lys Ala Glu Thr Thr Pro Thr Gly
        35                  40                  45

Gly Ala Thr Ser Ser Ala Thr Ala Ser Gly Ser Ser Ser Gly Arg Arg
    50                  55                  60

Pro Arg Gly Arg Pro Ala Gly Ser Lys Asn Lys Pro Lys Pro Pro Thr
65                  70                  75                  80

Ile Ile Thr Arg Asp Ser Pro Asn Val Leu Arg Ser His Val Leu Glu
                85                  90                  95

Val Thr Ser Gly Ser Asp Ile Ser Glu Ala Val Ser Thr Tyr Ala Thr
            100                 105                 110

Arg Arg Gly Cys Gly Val Cys Ile Ile Ser Gly Thr Gly Ala Val Thr
        115                 120                 125

Asn Val Thr Ile Arg Gln Pro Ala Ala Pro Ala Gly Gly Gly Val Ile
    130                 135                 140

Thr Leu His Gly Arg Phe Asp Ile Leu Ser Leu Thr Gly Thr Ala Leu
145                 150                 155                 160

Pro Pro Pro Ala Pro Pro Gly Ala Gly Gly Leu Thr Val Tyr Leu Ala
                165                 170                 175

Gly Gly Gln Gly Gln Val Val Gly Gly Asn Val Ala Gly Ser Leu Ile
            180                 185                 190

Ala Ser Gly Pro Val Val Leu Met Ala Ala Ser Phe Ala Asn Ala Val
        195                 200                 205

Tyr Asp Arg Leu Pro Ile Glu Glu Glu Thr Pro Pro Arg Thr
    210                 215                 220

Thr Gly Val Gln Gln Gln Pro Glu Ala Ser Gln Ser Ser Glu Val
225                 230                 235                 240

Thr Gly Ser Gly Ala Gln Ala Cys Glu Ser Asn Leu Gln Gly Gly Asn
                245                 250                 255

Gly Gly Gly Gly Val Ala Phe Tyr Asn Leu Gly Met Asn Met Asn Asn
            260                 265                 270

Phe Gln Phe Ser Gly Gly Asp Ile Tyr Gly Met Ser Gly Ser Gly
        275                 280                 285

Gly Gly Gly Gly Gly Ala Thr Arg Pro Ala Phe
```

<210> SEQ ID NO 59
<211> LENGTH: 585
<212> TYPE: DNA
<213> ORGANISM: Arabidopsis thaliana
<220> FEATURE:
<223> OTHER INFORMATION: SEQ ID NO: 59  G1274 cDNA (start codon begins
      at nucleotide 1)

<400> SEQUENCE: 59

```
atgaatatct ctcaaaaccc tagccctaat tttacgtact tctccgatga aactttatt      60
aatccgttta tggataacaa cgatttctca aatttgatgt tctttgacat agatgaagga    120
ggtaacaatg gattaatcga ggaagagatc tcatctccga caagcatcgt ttcgtcggag    180
acatttaccg gggaaagcgg cggatccggc agcgcaacaa cgttgagtaa aaaggaatca    240
actaatagag gaagtaaaga gagtgatcag acgaaggaga cgggtcatcg agttgcattt    300
agaacgagat cgaagattga tgtgatggat gatggtttta atggaggaa gtatggcaag    360
aaatctgtca aaacaacat taacaagagg aattactaca aatgctcaag tgaaggttgc    420
tcggtgaaga gagggtaga gagagatggt gacgatgcag cttatgtaat tacaacatat    480
gaaggagtcc ataaccatga gagtctctct aatgtctatt acaatgaaat ggttttatct    540
tatgatcatg ataactggaa ccaacactct cttcttcgat cttaa                    585
```

<210> SEQ ID NO 60
<211> LENGTH: 194
<212> TYPE: PRT
<213> ORGANISM: Arabidopsis thaliana
<220> FEATURE:
<223> OTHER INFORMATION: SEQ ID NO: 60  G1274 polypeptide

<400> SEQUENCE: 60

```
Met Asn Ile Ser Gln Asn Pro Ser Pro Asn Phe Thr Tyr Phe Ser Asp
1               5                   10                  15

Glu Asn Phe Ile Asn Pro Phe Met Asp Asn Asn Asp Phe Ser Asn Leu
            20                  25                  30

Met Phe Phe Asp Ile Asp Glu Gly Gly Asn Asn Gly Leu Ile Glu Glu
        35                  40                  45

Glu Ile Ser Ser Pro Thr Ser Ile Val Ser Ser Glu Thr Phe Thr Gly
    50                  55                  60

Glu Ser Gly Gly Ser Gly Ser Ala Thr Thr Leu Ser Lys Lys Glu Ser
65                  70                  75                  80

Thr Asn Arg Gly Ser Lys Glu Ser Asp Gln Thr Lys Glu Thr Gly His
                85                  90                  95

Arg Val Ala Phe Arg Thr Arg Ser Lys Ile Asp Val Met Asp Asp Gly
            100                 105                 110

Phe Lys Trp Arg Lys Tyr Gly Lys Lys Ser Val Lys Asn Asn Ile Asn
        115                 120                 125

Lys Arg Asn Tyr Tyr Lys Cys Ser Ser Glu Gly Cys Ser Val Lys Lys
    130                 135                 140

Arg Val Glu Arg Asp Gly Asp Asp Ala Ala Tyr Val Ile Thr Thr Tyr
145                 150                 155                 160

Glu Gly Val His Asn His Glu Ser Leu Ser Asn Val Tyr Tyr Asn Glu
                165                 170                 175

Met Val Leu Ser Tyr Asp His Asp Asn Trp Asn Gln His Ser Leu Leu
            180                 185                 190
```

Arg Ser

<210> SEQ ID NO 61
<211> LENGTH: 696
<212> TYPE: DNA
<213> ORGANISM: Arabidopsis thaliana
<220> FEATURE:
<223> OTHER INFORMATION: SEQ ID NO: 61   G1792 cDNA (start codon begins
      at nucleotide 77)

<400> SEQUENCE: 61

```
aatccataga tctcttatta ataacagtg ctgaccaagc tcttacaaag caaaccaatc      60
tagaacacca aagttaatgg agagctcaaa caggagcagc aacaaccaat cacaagatga    120
caagcaagct cgtttccggg gagttcgaag aaggccttgg ggaaagtttg cagcagagat    180
tcgagacccg tcgagaaacg gtgcccgtct ttggctcggg acatttgaga ccgctgagga    240
ggcagcaagg gcttatgacc gagcagcctt taaccttagg ggtcatctcg ctatactcaa    300
cttccctaat gagtattatc cacgtatgga cgactactcg cttcgccctc cttatgcttc    360
ttcttcttcg tcgtcgtcat cgggttcaac ttctactaat gtgagtcgac aaaaccaaag    420
agaagttttc gagtttgagt atttggacga taaggttctt gaagaacttc ttgattcaga    480
agaaaggaag agataatcac gattagtttt gttttgatat tttatgtggc actgttgtgg    540
ctacctacgt gcattatgtg catgtatagg tcgcttgatt agtactttat aacatgcatg    600
ccacgaccat aaattgtaag agaagacgta ctttgcgttt tcatgaaata tgaatgttag    660
atggtttgag tacaaaaaaa aaaaaaaaaa aaaaaa                               696
```

<210> SEQ ID NO 62
<211> LENGTH: 139
<212> TYPE: PRT
<213> ORGANISM: Arabidopsis thaliana
<220> FEATURE:
<223> OTHER INFORMATION: SEQ ID NO: 62   G1792 polypeptide

<400> SEQUENCE: 62

```
Met Glu Ser Ser Asn Arg Ser Asn Asn Gln Ser Gln Asp Asp Lys
1               5                   10                  15

Gln Ala Arg Phe Arg Gly Val Arg Arg Pro Trp Gly Lys Phe Ala
                20                  25                  30

Ala Glu Ile Arg Asp Pro Ser Arg Asn Gly Ala Arg Leu Trp Leu Gly
                35                  40                  45

Thr Phe Glu Thr Ala Glu Glu Ala Ala Arg Ala Tyr Asp Arg Ala Ala
            50                  55                      60

Phe Asn Leu Arg Gly His Leu Ala Ile Leu Asn Phe Pro Asn Glu Tyr
65                  70                  75                  80

Tyr Pro Arg Met Asp Asp Tyr Ser Leu Arg Pro Pro Tyr Ala Ser Ser
                85                  90                      95

Ser Ser Ser Ser Ser Ser Gly Ser Thr Ser Thr Asn Val Ser Arg Gln
                100                 105                     110

Asn Gln Arg Glu Val Phe Glu Phe Glu Tyr Leu Asp Asp Lys Val Leu
            115                 120                 125

Glu Glu Leu Leu Asp Ser Glu Glu Arg Lys Arg
        130                 135
```

<210> SEQ ID NO 63
<211> LENGTH: 785
<212> TYPE: DNA
<213> ORGANISM: Arabidopsis thaliana

```
<220> FEATURE:
<223> OTHER INFORMATION: SEQ ID NO: 63  G47 cDNA (start codon begins at
      nucleotide 38)

<400> SEQUENCE: 63
cttcttcttc acatcgatca tcatacaaca acaaaaaatg gattacagag aatccaccgg    60
tgaaagtcag tcaaagtaca aaggaatccg tcgtcggaaa tggggcaaat gggtatcaga   120
gattagagtt ccgggaactc gtgaccgtct ctggttaggt tcattctcaa cagcagaagg   180
tgccgccgta gcacacgacg ttgctttctt ctgtttacac caacctgatt ctttagaatc   240
tctcaatttc cctcatttgc ttaatccttc actcgtttcc agaacttctc cgagatctat   300
ccagcaagct gcttctaacg ccggcatggc cattgacgcc ggaatcgtcc acagtaccag   360
cgtgaactct ggatgcggag atacgacgac gtattacgag aatggagctg atcaagtgga   420
gccgttgaat atttcagtgt atgattatct gggcggccac gatcacgttt gatttatctc   480
gacggtcatg atcacgtttg atcttctttt gagtaagatt ttgtaccata atcaaaacag   540
gtgtggtgct aaaatcttac tcaaaacaag attaggtacc acagagaaac aatcaaatgg   600
ttgtgaatat acattataag gttttgatta atgtttgttt cactgattta gtgaagtttg   660
gtccattgta tacaaatcta ttcaagaaac ctagcgcgag atcatgtttc gtgattgaag   720
attgagattt ttaagtattc gtaatatttt tgtaaaatac aaataaaaaa aaaaaaaaaa   780
aaaaa                                                                785

<210> SEQ ID NO 64
<211> LENGTH: 144
<212> TYPE: PRT
<213> ORGANISM: Arabidopsis thaliana
<220> FEATURE:
<223> OTHER INFORMATION: SEQ ID NO: 64  G47 polypeptide

<400> SEQUENCE: 64

Met Asp Tyr Arg Glu Ser Thr Gly Glu Ser Gln Ser Lys Tyr Lys Gly
1               5                   10                  15

Ile Arg Arg Arg Lys Trp Gly Lys Trp Val Ser Glu Ile Arg Val Pro
            20                  25                  30

Gly Thr Arg Asp Arg Leu Trp Leu Gly Ser Phe Ser Thr Ala Glu Gly
        35                  40                  45

Ala Ala Val Ala His Asp Val Ala Phe Phe Cys Leu His Gln Pro Asp
    50                  55                  60

Ser Leu Glu Ser Leu Asn Phe Pro His Leu Leu Asn Pro Ser Leu Val
65                  70                  75                  80

Ser Arg Thr Ser Pro Arg Ser Ile Gln Gln Ala Ala Ser Asn Ala Gly
                85                  90                  95

Met Ala Ile Asp Ala Gly Ile Val His Ser Thr Ser Val Asn Ser Gly
            100                 105                 110

Cys Gly Asp Thr Thr Thr Tyr Tyr Glu Asn Gly Ala Asp Gln Val Glu
        115                 120                 125

Pro Leu Asn Ile Ser Val Tyr Asp Tyr Leu Gly Gly His Asp His Val
    130                 135                 140

<210> SEQ ID NO 65
<211> LENGTH: 3158
<212> TYPE: DNA
<213> ORGANISM: artificial sequence
<220> FEATURE:
<223> OTHER INFORMATION: SEQ ID NO: 65  pMEN65 expression vector
<220> FEATURE:
```

```
<221> NAME/KEY: misc_feature
<222> LOCATION: (7)..(10)
<223> OTHER INFORMATION: n is a, c, g, or t
<220> FEATURE:
<221> NAME/KEY: misc_feature
<222> LOCATION: (17)..(52)
<223> OTHER INFORMATION: n is a, c, g, or t

<400> SEQUENCE: 65
aagcttnnnn ctgcagnnnn nnnnnnnnnn nnnnnnnnnn nnnnnnnnnn nntcggattc      60
cattgcccag ctatctgtca ctttattgtg aagatagtga aaaagaaggt ggctcctaca     120
aatgccatca ttgcgataaa ggaaaggcca tcgttgaaga tgcctctgcc gacagtggtc     180
ccaaagatgg accccacccc acgaggagca tcgtggaaaa agaagacgtt ccaaccacgt     240
cttcaaagca agtggattga tgtgatggtc cgattgagac ttttcaacaa agggtaatat     300
ccggaaacct cctcggattc cattgcccag ctatctgtca ctttattgtg aagatagtgg     360
aaaaggaagg tggctcctac aaatgccatc attgcgataa aggaaaggcc atcgttgaag     420
atgcctctgc cgacagtggt cccaaagatg accccacc cacgaggagc atcgtggaaa      480
aagaagacgt tccaaccacg tcttcaaagc aagtggattg atgtgatatc tccactgacg     540
taagggatga cgcacaatcc cactatcctt cgcaagaccc ttcctctata taggaagtt     600
catttcattt ggagaggaca cgctgacaag ctgactctag cagatctggt accgtcgacg     660
gtgagctccg cggccgctct agacaggcct cgtaccggat cctctagcta gagctttcgt     720
tcgtatcatc ggtttcgaca acgttcgtca agttcaatgc atcagtttca ttgcgcacac     780
accagaatcc tactgagttt gagtattatg cattgggaa aactgttttt cttgtaccat      840
ttgttgtgct tgtaatttac tgtgtttttt attcggtttt cgctatcgaa ctgtgaaatg     900
gaaatggatg gagaagagtt aatgaatgat atggtccttt tgttcattct caaattaata     960
ttatttgttt tttctcttat ttgttgtgtg ttgaatttga aattataaga gatatgcaaa    1020
cattttgttt tgagtaaaaa tgtgtcaaat cgtggcctct aatgaccgaa gttaatatga    1080
ggagtaaaac acttgtagtt gtaccattat gcttattcac taggcaacaa atatattttc    1140
agacctagaa aagctgcaaa tgttactgaa tacaagtatg tcctcttgtg ttttagacat    1200
ttatgaactt tcctttatgt aatttttccag aatccttgtc agattctaat cattgcttta    1260
taattatagt tatactcatg gatttgtagt tgagtatgaa atatttttt aatgcatttt     1320
atgacttgcc aattgattga caacatgcat caatcgacct gcagccactc gaagcggccg    1380
gccgccactc gagatcatga gcggagaatt aagggagtca cgttatgacc ccgccgatg     1440
acgcgggaca agccgtttta cgtttggaac tgacagaacc gcaacgttga aggagccact    1500
cagccgcggg tttctggagt ttaatgagct aagcacatac gtcagaaacc attattgcgc    1560
gttcaaaagt cgcctaaggt cactatcagc tagcaaatat ttcttgtcaa aaatgctcca    1620
ctgacgttcc ataaattccc ctcggtatcc aattagagtc tcatattcac tctcaatcca    1680
aataatctgc accggatctg gatcgtttcg catgattgaa caagatggat tgcacgcagg    1740
ttctccggcc gcttgggtgg agaggctatt cggctatgac tgggcacaac agacaatcgg    1800
ctgctctgat gccgccgtgt tccggctgtc agcgcagggg cgcccggttc tttttgtcaa    1860
gaccgacctg tccggtgccc tgaatgaact gcaggacgag gcagcgcggc tatcgtggct    1920
ggccacgacg ggcgttcctt gcgcagctgt gctcgacgtt gtcactgaag cgggaaggga    1980
ctggctgcta ttgggcgaag tgccggggca ggatctcctg tcatctcacc ttgctcctgc    2040
cgagaaagta tccatcatgg ctgatgcaat gcggcggctg catacgcttg atccggctac    2100
```

```
ctgcccattc gaccaccaag cgaaacatcg catcgagcga gcacgtactc ggatggaagc    2160
cggtcttgtc gatcaggatg atctggacga agagcatcag gggctcgcgc cagccgaact    2220
gttcgccagg ctcaaggcgc gcatgcccga cggcgaggat ctcgtcgtga cccatggcga    2280
tgcctgcttg ccgaatatca tggtggaaaa tggccgcttt tctggattca tcgactgtgg    2340
ccggctgggt gtggcggacc gctatcagga catagcgttg gctacccgtg atattgctga    2400
agagcttggc ggcgaatggg ctgaccgctt cctcgtgctt tacggtatcg ccgctcccga    2460
ttcgcagcgc atcgccttct atcgccttct tgacgagttc ttctgagcgg gactctgggg    2520
ttcgaaatga ccgaccaagc gacgcccaac ctgccatcac gagatttcga ttccaccgcc    2580
gccttctatg aaaggttggg cttcggaatc gttttccggg acgccggctg gatgatcctc    2640
cagcgcgggg atctcatgct ggagttcttc gcccacggga tctctgcgga acaggcggtc    2700
gaaggtgccg atatcattac gacagcaacg gccgacaagc acaacgccac gatcctgagc    2760
gacaatatga tcgggcccgg cgtccacatc aacggcgtcg gcggcgactg cccaggcaag    2820
accgagatgc accgcgatat cttgctgcgt tcggatattt tcgtggagtt cccgccacag    2880
acccggatga tccccgatcg ttcaaacatt tggcaataaa gtttcttaag attgaatcct    2940
gttgccggtc ttgcgatgat tatcatataa tttctgttga attacgttaa gcatgtaata    3000
attaacatgt aatgcatgac gttatttatg agatgggttt ttatgattag agtcccgcaa    3060
ttatacattt aatacgcgat agaaaacaaa atatagcgcg caaactagga taaattatcg    3120
cgcgcggtgt catctatgtt actagatcgg gctcgaga                            3158

<210> SEQ ID NO 66
<211> LENGTH: 1351
<212> TYPE: DNA
<213> ORGANISM: artificial sequence
<220> FEATURE:
<223> OTHER INFORMATION: SEQ ID NO: 66

<400> SEQUENCE: 66
tcgacaggaa tgcgtctctg agttcatcag cttcgtcacc agcgaggcta gtgataagtg      60
ccaaagagag aaaaggaaga ccatcaatgg agatgatttg ctttgggcta tggtcacttt     120
aggatttgag gattacgcgg ccgcggagca agacaggttc ttaccgatcg ctaacgttag     180
caggatcatg aagaaagcac ttcctgcgaa cgcaaaaatc tctaaggatg ctaaagaaac     240
gatgcaggag tgtgtgaatt cggtagccca attggtaagg aaataattat tttctttttt     300 cctttagta taaaatagtt aagtgatgtt aattagtatg attataataa tatagttgtt     360
ataattgtga aaaataatt tataaatata ttgtttacat aaacaacata gtaatgtaaa     420
aaaatatgac aagtgatgtg taagacgaag aagataaaag ttgagagtaa gtatattatt     480
tttaatgaat ttgatcgaac atgtaagatg atatactagc attaatatttt gttttaatca     540 taatagtaat tctagctggt ttgatgaatt aaatatcaat gataaaatac tatagtaaaa     600
ataagaataa ataaattaaa ataatatttt tttatgatta atagtttatt atataattaa     660
atatctatac cattactaaa tattttagtt taaaagttaa taaatatttt gttagaaatt     720
ccaatctgct tgtaatttat caataaacaa atatattaaat aacaagctaa agtaacaaat     780
aatatcaaac taatagaaac agtaatctaa tgtaacaaaa cataatctaa tgctaatata     840
acaaagcgca agatctatca attttatata gtattatttt tcaatcaaca ttcttattaa     900
tttctaaata atacttgtag ttttattaac ttctaaatgg attgactatt aattaaatga     960
```

| | |
|---|---|
| attagtcgaa catgaataaa caaggtaaca tgatagatca tgtcattgtg ttatcattga | 1020 |
| tattacattt ggattgatta cagttgggaa attgggttcg aaatcgataa gcttgcggcc | 1080 |
| gctctagaga attcacacac tcctgcatcg tttctttagc atccttagag attttgcgt | 1140 |
| tcgcaggaag tgctttcttc atgatcctgc taacgttagc gatcggtaag aacctgtctt | 1200 |
| gctccgcggc cgcgtaatcc tcaaatccta aagtgaccat agcccaaagc aaatcatctc | 1260 |
| cattgatggt cttccttttc tctctttggc acttatcact agcctcgctg gtgacgaagc | 1320 |
| tgatgaactc agagacgcat tcctgtcgac g | 1351 |

<210> SEQ ID NO 67
<211> LENGTH: 528
<212> TYPE: DNA
<213> ORGANISM: Arabidopsis thaliana
<220> FEATURE:
<223> OTHER INFORMATION: SEQ ID NO: 67  G2345 cDNA

<400> SEQUENCE: 67

| | |
|---|---|
| atggccgaat cgcaaaccgg tggtggtggt ggtggaagcc atgagagtgg cggtgatcag | 60 |
| agcccgaggt ctttgaatgt tcgtgagcag acaggtttc ttccgattgc taacataagc | 120 |
| cgtatcatga gagaggtttt acctctaaat ggcaaaatcg ctaaagatgc taaagagact | 180 |
| atgcaggaat gtgtctctga attcatcagc ttcgtcacca gcgaggctag tgataagtgc | 240 |
| caaagagaga aaggaagac catcaatgga gatgatttgc tttgggctat ggccacttta | 300 |
| ggattcgaag attcatcga tccctcaag gtttacctga tgcgatatag agagatggag | 360 |
| ggtgacacta aaggatcagg aaaaggcggg gaatcgagtg caaagagaga tggtcaacca | 420 |
| agccaagtgt ctcagttctc gcaggttcct caacaaggct cattctcaca gggtccttat | 480 |
| ggaaactctc aaggttcgaa tatgatggtt caaatgccgg gcacagag | 528 |

<210> SEQ ID NO 68
<211> LENGTH: 483
<212> TYPE: DNA
<213> ORGANISM: Arabidopsis thaliana
<220> FEATURE:
<223> OTHER INFORMATION: SEQ ID NO: 68  G485 cDNA

<400> SEQUENCE: 68

| | |
|---|---|
| atggcggatt cggacaacga ttcaggagga cacaaagacg gtggaaatgc ttcgacacgt | 60 |
| gagcaagata ggtttctacc gatcgctaac gttagcagga tcatgaagaa agcacttcct | 120 |
| gcgaacgcaa aaatctctaa ggatgctaaa gaaacggttc aagagtgtgt atcggaattc | 180 |
| ataagtttca tcaccggtga ggcttctgac aagtgtcaga gagagaagag gaagacaatc | 240 |
| aacggtgacg atcttctttg ggcgatgact acgctaggt ttgaggacta cgtggagcct | 300 |
| ctcaaggttt atctgcaaaa gtatagggag gtggaaggag agaagactac tacggcaggg | 360 |
| agacaaggcg ataaggaagg tggaggagga ggcggtggag ctggaagtgg aagtggagga | 420 |
| gctccgatgt acggtggtgg catggtgact acgatggac atcaattttc ccatcatttt | 480 |
| tct | 483 |

<210> SEQ ID NO 69
<211> LENGTH: 131
<212> TYPE: DNA
<213> ORGANISM: Arabidopsis thaliana
<220> FEATURE:
<223> OTHER INFORMATION: SEQ ID NO: 69  base pairs 185-315 from the
    G2345 cDNA start codon

```
<400> SEQUENCE: 69
aggaatgtgt ctctgaattc atcagcttcg tcaccagcga ggctagtgat aagtgccaaa      60
gagagaaaag gaagaccatc aatggagatg atttgctttg ggctatggcc actttaggat    120
tcgaagatta c                                                          131

<210> SEQ ID NO 70
<211> LENGTH: 110
<212> TYPE: DNA
<213> ORGANISM: Arabidopsis thaliana
<220> FEATURE:
<223> OTHER INFORMATION: SEQ ID NO: 70  base pairs 61-170 from the G485
      cDNA start codon

<400> SEQUENCE: 70
gagcaagata ggtttctacc gatcgctaac gttagcagga tcatgaagaa agcacttcct      60
gcgaacgcaa aaatctctaa ggatgctaaa gaaacggttc aagagtgtgt                110

<210> SEQ ID NO 71
<211> LENGTH: 154
<212> TYPE: DNA
<213> ORGANISM: artificial sequence
<220> FEATURE:
<223> OTHER INFORMATION: SEQ ID NO: 71  P26884 carries KanR and a
      35S::miR169d fusion and is an overexpression construct for
      ath-miR169d, one of the precursors to miR169 which targets NF-YA
      HAP2 class transcription factor genes

<400> SEQUENCE: 71
gtatcataga gtcttgcatg gaaaaattaa agaatgagat tgagccaagg atgacttgcc      60
gatgttatca acaaatctta actgattttg gtgtccggca agttgaccttt ggctctgttt    120 ccttcttttc ttttcaatgt caaactctag atat                                 154

<210> SEQ ID NO 72
<211> LENGTH: 217
<212> TYPE: DNA
<213> ORGANISM: artificial sequence
<220> FEATURE:
<223> OTHER INFORMATION: SEQ ID NO: 72  P26885 carries KanR and a
      35S::miR169d fusion and is an overexpression construct for
      ath-miR169e, one of the precursors to miR169 which targets NF-YA
      HAP2 class transcription factor genes

<400> SEQUENCE: 72
tgatgatgat gatgagtcac taattaattg tatcatagag tcttgcatgg aaaaatagaa      60
aatgagattg agccaaggat gacttgccga ttttctcaac gaatcttact gattatggta    120
tccggcaagt tgactttggc tctgtttcct tcccttcttt tcgatgtcaa actctagata    180
cctaaccaca tatcatatat atcatcatca ttcatca                             217

<210> SEQ ID NO 73
<211> LENGTH: 167
<212> TYPE: DNA
<213> ORGANISM: artificial sequence
<220> FEATURE:
<223> OTHER INFORMATION: SEQ ID NO: 73  P26886 carries KanR and a
      35S::miR169d fusion and is an overexpression construct for
      ath-miR169f, one of the precursors to miR169 which targets NF-YA
      HAP2 class transcription factor genes

<400> SEQUENCE: 73
gggtcttgca tgaaggaata acgaatggaa ttgagccaag gatgacttgc cggtttaaac      60
ccaaccggtt tatgaccatt gatttggtct cattcacaat ctgttgattc gtgtctggca    120
```

```
agttgaccttggctctgcttcgttctctattcttccatgttagattc         167

<210> SEQ ID NO 74
<211> LENGTH: 379
<212> TYPE: DNA
<213> ORGANISM: artificial sequence
<220> FEATURE:
<223> OTHER INFORMATION: SEQ ID NO: 74  P26887 carries KanR and a
      35S::miR169d fusion and is an overexpression construct for
      ath-miR169g, one of the precursors to miR169 which targets NF-YA
      HAP2 class transcription factor genes

<400> SEQUENCE: 74
tgcctataaa taccttcatc acgagtatga caagatcaca agacaagaaa agaaaggtag     60
agaaaacatg ataatgatga ttacgatgat gagagtctct agttgtatca gagggtcttg    120
catggaagaa tagagaatga ggttgagcca aggatgactt gccgggtttt tttaccaatg    180
aatctaatta actgattctg gtgtccggca agttgacctt ggctctgttt ccttctcttc    240
ttttggatgt cagactccaa gatatctatc atcatgaatc gtgatcaaac tttgtaattt    300
cattgaaatg tgttttcttt gatgcgaatt ttttggctta cggtttttcg atttgaatga    360
tcagattttt gttttgca                                                  379
```

WATER DEFICIT-INDUCIBLE PROMOTERS

Figure 1:
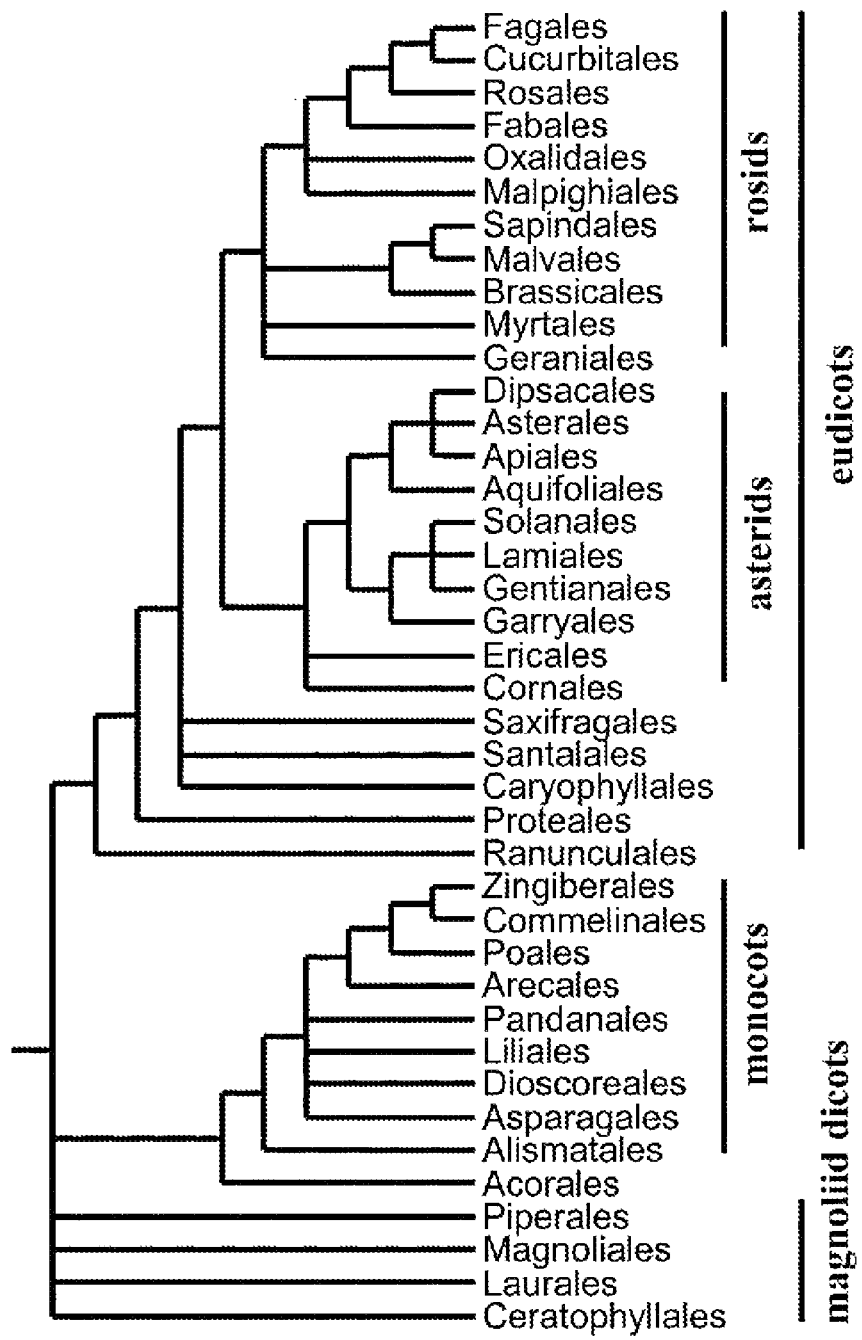

This is a U.S. National Phase patent application of PCT/US2008/053354, filed Feb. 7, 2008, which claims priority to U.S. Provisional patent application Ser. No. 60/900,497 filed Feb. 8, 2007, all of which are hereby incorporated by reference in the present disclosure in their entirety.

JOINT RESEARCH AGREEMENT

The present invention, in the field of functional genomics and the characterization of plant genes for the improvement of plants, was made by or on behalf of Mendel Biotechnology, Inc. and Monsanto Corporation as a result of activities undertaken within the scope of a joint research agreement in effect on or before the date the present invention was made.

FIELD OF THE INVENTION

The present invention relates to plant genomics and more specifically pertains to water deficit-inducible promoters that mediate gene expression during a plant's response to water deficit.

BACKGROUND OF THE INVENTION

In the natural environment, plants often grow under unfavorable conditions, including water deficit conditions such as drought, a severe form of low water availability generally characterized as a prolonged period of water deficit. Water deficit, or water deprivation, can delay growth and development, reduce productivity, and in extreme cases, cause the plant to die. Low water availability is a major factor in crop yield reduction worldwide. Problems for plants caused by low water availability include mechanical stresses caused by the withdrawal of cellular water. Drought also causes plants to become more susceptible to various diseases (Simpson, ed. (1981) "The Value of Physiological Knowledge of Water Stress in Plants", in *Water Stress on Plants*, Praeger, NY, pp. 235-265).

A number of polypeptides, including, for example, transcription factors (TFs), have been shown to improve the tolerance of plant species to water deficit conditions (for examples, see publication no. WO2004076638). However, important limitations in the use of various proteins that confer water deficit tolerance to crop species when the proteins are overexpressed may include negative side effects associated with constitutive overexpression of these polypeptides. Possible pleiotropic effects such as small size, delayed growth, increased disease sensitivity, and development and alteration in flowering time are common. It has been proposed that genes conferring tolerance to water deficit impose a cost on overall fitness and development. To overcome these limitations, the present studies were initiated to discover and assess the utility of numerous promoter sequences that respond to water deficit conditions. These promoter sequences can be used to regulate protein expression during periods of drought or other water deficit conditions, and therefore may be used to induce overexpression of polypeptides that can confer improved water deficit tolerance when they are needed without the adverse developmental or morphological effects that may be associated with their constitutive overexpression. Numerous transgenic plants using these promoter sequences to regulate polypeptides were developed and the plants were analyzed for their tolerance to water deficit conditions. Many of these promoter sequences can be used to produce commercially valuable plants and crops as well as the methods for making them and using them.

The present invention thus relates to methods and compositions for producing transgenic plants, where water deficit-inducible overexpression of transcription factors confers enhanced tolerance to water deficit with reduced or no impact on yield, appearance, quality or fitness, as compared to plants constitutively overexpressing the same transcription factors. Other aspects and embodiments of the invention are described below and can be derived from the teachings of this disclosure as a whole.

SUMMARY OF THE INVENTION

The present invention is directed to promoter sequences that may be used to transform a plant. The promoter sequences are able to respond to water deficit conditions and can be used to drive the expression of a polynucleotide sequence that encodes a polypeptide that can confer increased tolerance to water deficit, including drought, desiccation, dehydration, or a related hyperosmotic stress (for example, freezing or high salt concentration). Thus, the polypeptide may be expressed in a water-deficit inducible manner.

The invention also provides an isolated nucleic acid comprising a water deficit-inducible promoter that includes any of the promoter sequences provided by SEQ ID NOs: 1-9. A water deficit-inducible promoter of the invention may comprise a functional part thereof, provided the functional part also includes a water-deficit-inducible promoter function. The functional part of the promoter may have about 50, 100, 125, 150, 175, 200, 225, 250, 275, 300, 325, 350, 375, 400, 425, 447, 450, 460, 475, 500, 525, 550, 575, 600, 605, 625, 650, 675, 700, 725, 750, 766, 775, 776, 780, 800, 825, 850, 875, 900, 907, 928 or 936 contiguous nucleotides of the nucleic acid sequences of SEQ ID NOs: 1-9, as well as all lengths of contiguous nucleotides within such sizes.

The invention also pertains to expression vectors that can comprise a promoter sequence of the invention. The water deficit-inducible promoter may comprise any of SEQ ID NOs: 1 to 9, or a functional part thereof, provided the functional part also includes a water-deficit-inducible promoter function. The promoter comprises a transcription initiation domain having an RNA polymerase binding site. The promoter is located 5' relative to and is operably linked to a coding sequence encoding a polypeptide that confers to a plant increased tolerance to water deficit conditions. Many of the expression vectors provided as SEQ ID NOs: 10 to 54 (each of which comprises a promoter of any of SEQ ID NOs: 1-9, as well as a nucleic acid sequence encoding a polypeptide that confers increased tolerance to water deficit) have been introduced into plants, and the plants not only have been shown to have greater water deficit tolerance than a control plant, but the transformed plants are often of wild-type or near-wild type morphology and development (many polypeptides that contribute to improved water deficit tolerance can also cause undesirable morphological and/or developmental traits when the polypeptides are constitutively overexpressed).

The invention encompasses a host plant cell comprising a water deficit-inducible promoter of the invention, comprising any of SEQ ID NOs: 1 to 9 or a functional part thereof, wherein the functional part includes a promoter function.

The invention also encompasses a transgenic plant comprising a water deficit-inducible promoter of the invention, comprising any of SEQ ID NOs: 1 to 9 or a functional part thereof, wherein the functional part includes a promoter function, and transgenic seed produced by the transgenic plants of the invention.

Methods for producing a transgenic plant having greater tolerance to water deficit conditions than a control plant, or for increasing the tolerance of a plant to water deficit, are provided. The method steps include the generation of an expression vector that comprises a promoter sequence of any of SEQ ID NOs: 1-9 or a functional part thereof, wherein the functional part includes a promoter function. The promoter sequence is operably linked to a nucleotide sequence that encodes a polypeptide that increases the water deficit tolerance in a plant, and during water deficit conditions the promoter sequence drives expression of the nucleotide sequence that encodes the polypeptide. A target plant is then transformed with the expression vector to produce a transgenic plant. When the polypeptide is overexpressed in the transformed plant (for example, during periods of water deficit), the transformed plant will have greater tolerance to water deficit conditions than the control plant. A transgenic plant that is produced by this method may be crossed with itself, a plant from the same line as the transgenic plant, a non-transgenic plant, a wild-type plant, or another transgenic plant from a different transgenic line of plants, to produce a transgenic seed that comprises the expression vector.

BRIEF DESCRIPTION OF THE SEQUENCE LISTING AND DRAWINGS

The Sequence Listing provides exemplary polynucleotide and polypeptide sequences of the invention. The traits associated with the use of the sequences are included in the Examples.

CD-ROMs Copy 1 and Copy 2, and the CRF copy of the Sequence Listing are read-only memory computer-readable compact discs. Each contains a copy of the Sequence Listing in ASCII text format. The Sequence Listing is named "MBI0079P.ST25.txt", the electronic file of the Sequence Listing contained on each of these CD-ROMs was created on Feb. 7, 2007, and is 127 kilobytes in size. The copies of the Sequence Listing on the CD-ROM discs are hereby incorporated by reference in their entirety.

FIG. 1 shows a conservative estimate of phylogenetic relationships among the orders of flowering plants (modified from Soltis et al. (1997) *Ann. Missouri Bot. Gard.* 84: 1-49). Those plants with a single cotyledon (monocots) are a monophyletic Glade nested within at least two major lineages of dicots; the eudicots are further divided into rosids and asterids. *Arabidopsis* is a rosid eudicot classified within the order Bras sicales; rice is a member of the monocot order Poales. FIG. 1 was adapted from Daly et al. (2001) *Plant Physiol.* 127: 1328-1333.

Figure 2:
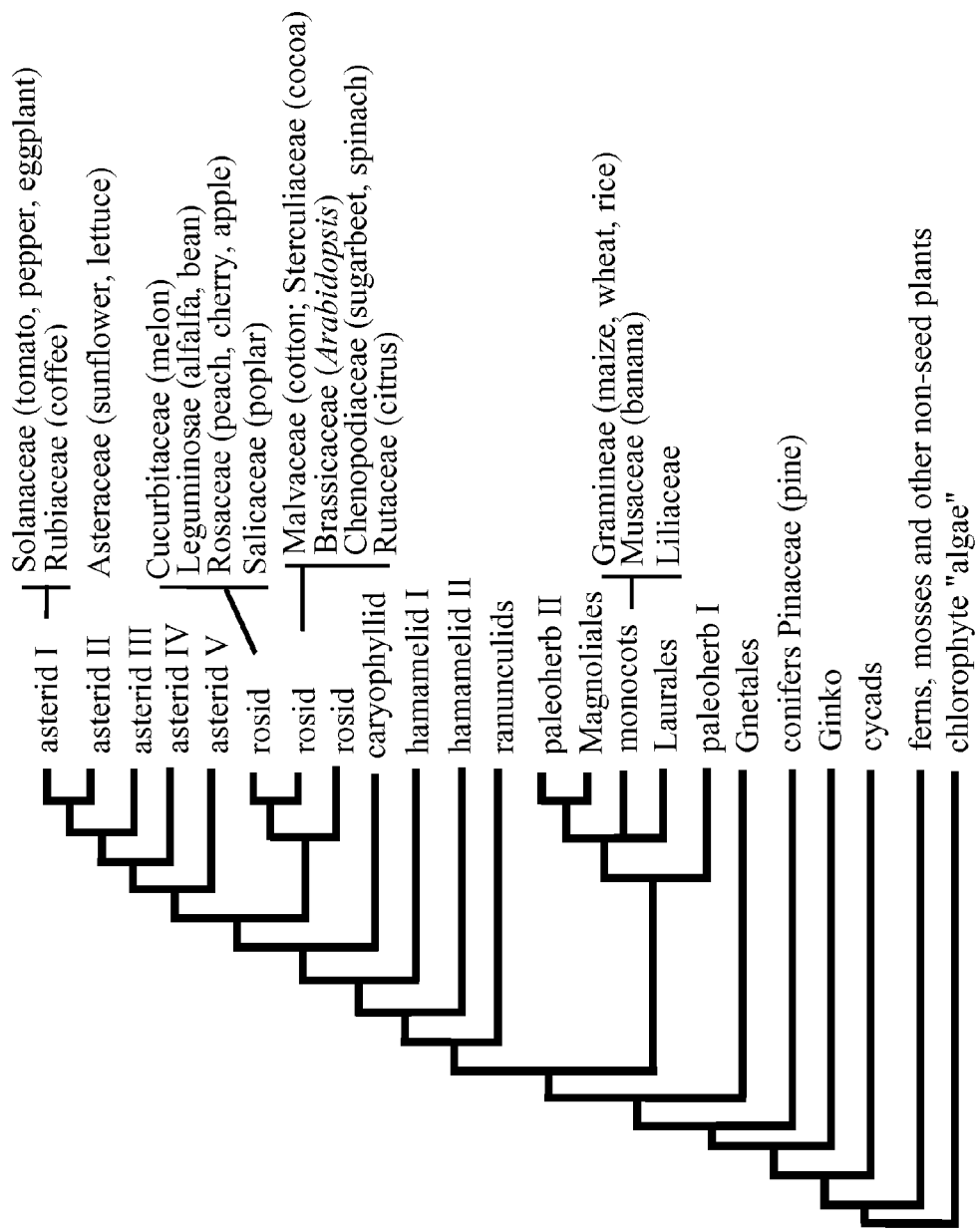

FIG. 2 shows a phylogenic dendogram depicting phylogenetic relationships of higher plant taxa, including clades containing tomato and *Arabidopsis*; adapted from Ku et al. (2000) *Proc. Natl. Acad. Sci.* USA 97: 9121-912; and Chase et al. (1993) *Ann. Missouri Bot. Gard.* 80: 528-580.

Figure 3:
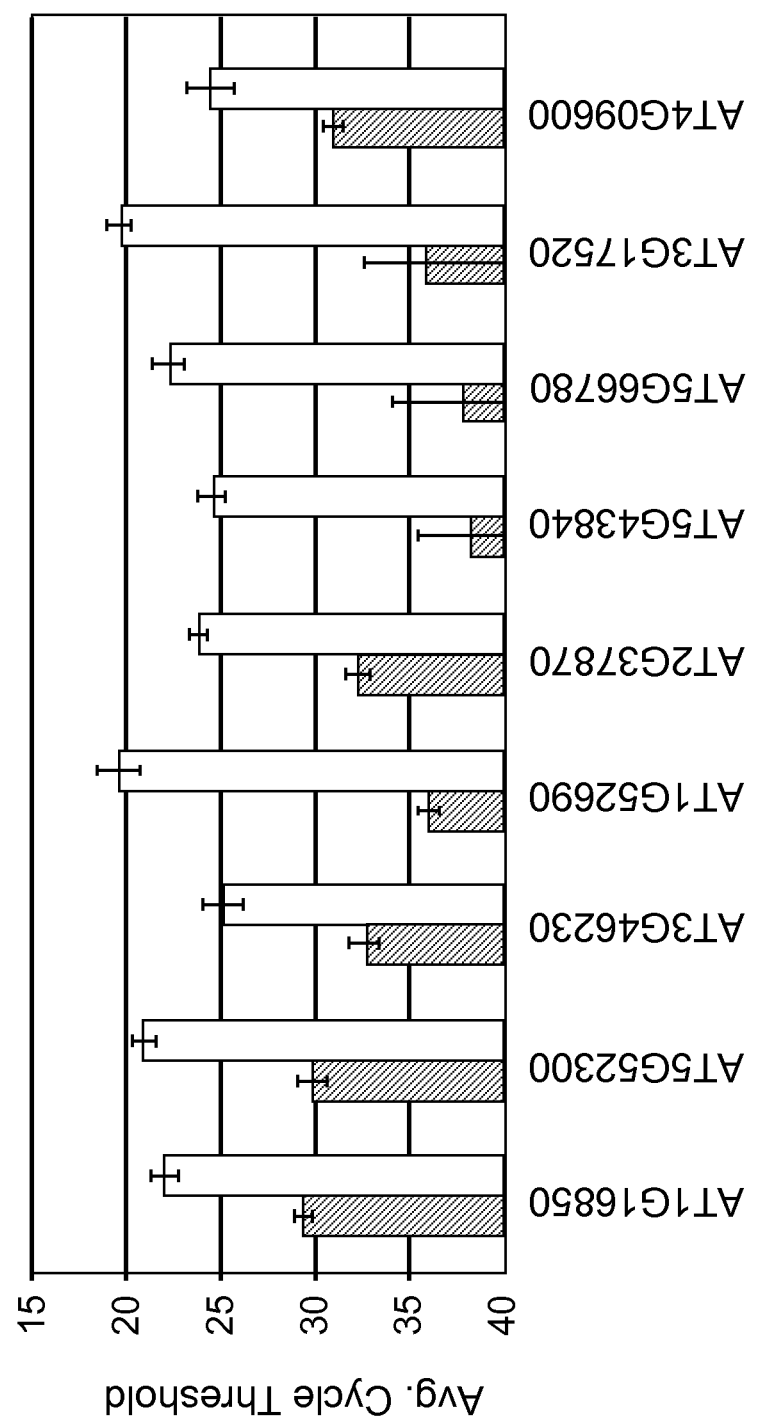

FIG. 3 shows the induction of *Arabidopsis* native genes corresponding to nine drought-promoters in a clay pot drought assay. Drought stressed and well-watered pMEN65 (empty vector) wild-type control plants were used for this experiment. Plants were drought stressed to the wilting point (as is typical for the clay pot assay to the point where they would normally be re-watered), and RT-PCR was performed using gene-specific primers for each of the genes indicated on the x-axis. The cycle threshold counts value was the real-time PCR cycle number at which the RNA transcript of interest was detectable above background. were normalized with 18S RNA. The checkered bars represent the average cycle threshold value for well-watered plants. The solid bars indicate the average cycle threshold value for the drought-stressed plants.

DETAILED DESCRIPTION

The present invention relates to polynucleotides and polypeptides for modifying phenotypes of plants, particularly promoter sequences associated with increased tolerance to water deficit such as desiccation, dehydration or drought, with respect to a control plant (for example, a genetically unaltered or non-transgenic plant such as a wild-type plant of the same species, or a transgenic plant line that comprises an empty expression vector). Throughout this disclosure, various information sources are referred to and/or are specifically incorporated. The information sources include scientific journal articles, patent documents, textbooks, and World Wide Web page addresses. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the invention.

As used herein and in the appended claims of the invention, the singular forms "a", "an", and "the" include the plural reference unless the context clearly dictates otherwise. Thus, for example, a reference to "a host cell" includes a plurality of such host cells, and a reference to "a stress" is a reference to one or more stresses and equivalents thereof known to those skilled in the art, and so forth.

DEFINITIONS

"Nucleic acid molecule" refers to an oligonucleotide, polynucleotide or any fragment thereof. It may be DNA or RNA of genomic or synthetic origin, double-stranded or single-stranded, and combined with carbohydrate, lipids, protein, or other materials to perform a particular activity such as transformation or form a useful composition such as a peptide nucleic acid (PNA).

"Polynucleotide" is a nucleic acid molecule comprising a plurality of polymerized nucleotides, e.g., at least about 15 consecutive polymerized nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single-stranded or double-stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single-stranded.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

An "isolated polynucleotide" is a polynucleotide, whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found with an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and that may be used to determine the limits of the genetically active unit (Rieger et al. (1976) *Glossary of Genetics and Cytogenetics: Classical and Molecular*, 4th ed., Springer Verlag, Berlin). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

A "promoter" or "promoter region" refers to an RNA polymerase binding site on a segment of DNA, generally found upstream or 5' relative to a coding sequence under the regulatory control of the promoter. The promoter will generally comprise response elements that are recognized by transcription factors. Transcription factors bind to the promoter sequences, recruiting RNA polymerase, which synthesizes RNA from the coding region. Dissimilarities in promoter sequences account for different efficiencies of transcription initiation and hence different relative expression levels of different genes.

"Promoter function" includes regulating expression of the coding sequences under a promoter's control by providing a recognition site for RNA polymerase and/or other factors, such as transcription factors, all of which are necessary for the start of transcription at a transcription initiation site. A "promoter function" may also include the extent to which a gene coding sequence is transcribed to the extent determined by a promoter sequence.

A promoter or promoter region may include variations of promoters found in the present Sequence Listing, which may be derived by ligation to other regulatory sequences, random mutagenesis, controlled mutagenesis, and/or by the addition or duplication of enhancer sequences. Promoters disclosed in the present Sequence Listing and biologically functional equivalents or variations thereof may drive the transcription of operably-linked coding sequences when comprised within an expression vector and introduced into a host plant. Promoters such as those found in the Sequence Listing (i.e., SEQ ID NOs: 1-9) may be used to generate similarly functional promoters containing essential promoter elements. Functional promoters of the invention may also include a functional part of any of SEQ ID NO: 1-9, provided the functional part also includes a water-deficit-inducible promoter function.

A "polypeptide" is an amino acid sequence comprising a plurality of consecutive polymerized amino acid residues e.g., at least about 15 consecutive polymerized amino acid residues. In many of the instances referred to in this application, a polypeptide comprises a polymerized amino acid residue sequence that is a transcription factor or a domain or portion or fragment thereof. Additionally, the polypeptide may comprise: (i) a localization domain; (ii) an activation domain; (iii) a repression domain; (iv) an oligomerization domain; (v) a DNA-binding domain; or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide or portions thereof whether naturally occurring or synthetic.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value therebetween. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical, matching or corresponding nucleotides at positions shared by the polynucleotide sequences. A degree of identity of polypeptide sequences is a function of the number of identical amino acids at corresponding positions shared by the polypeptide sequences. A degree of homology or similarity of polypeptide sequences is a function of the number of amino acids at corresponding positions shared by the polypeptide sequences.

"Complementary" refers to the natural hydrogen bonding by base pairing between purines and pyrimidines. For example, the sequence A-C-G-T (5'->3') forms hydrogen bonds with its complements A-C-G-T (5'->3') or A-C-G-U (5'->3'). Two single-stranded molecules may be considered partially complementary, if only some of the nucleotides bond, or "completely complementary" if all of the nucleotides bond. The degree of complementarity between nucleic acid strands affects the efficiency and strength of hybridization and amplification reactions. "Fully complementary" refers to the case where bonding occurs between every base pair and its complement in a pair of sequences, and the two sequences have the same number of nucleotides.

The terms "paralog" and "ortholog" are defined below in the section entitled "Orthologs and Paralogs". In brief, orthologs and paralogs are evolutionarily related genes that have similar sequences and functions. Orthologs are structurally related genes in different species that are derived by a speciation event. Paralogs are structurally related genes within a single species that are derived by a duplication event.

The term "equivalog" describes members of a set of homologous proteins that are conserved with respect to function since their last common ancestor. Related proteins are grouped into equivalog families, and otherwise into protein families with other hierarchically defined homology types. This definition is provided at the Institute for Genomic Research (TIGR) World Wide Web (www) website, "tigr.org" under the heading "Terms associated with TIGRFAMs".

In general, the term "variant" refers to molecules with some differences, generated synthetically or naturally, in their base or amino acid sequences as compared to a reference (native) polynucleotide or polypeptide, respectively. These differences include substitutions, insertions, deletions or any desired combinations of such changes in a native polynucleotide of amino acid sequence.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations may result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Also within the scope of the invention is a variant of a gene promoter listed in the Sequence Listing, that is, one having a sequence that differs from one of the polynucleotide sequences in the Sequence Listing, or a complementary sequence.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae (see for example, FIG. 1, adapted from Daly et al. (2001) supra, FIG. 2, adapted from Ku et al. (2000) supra; and see also Tudge (2000) in *The Variety of Life*, Oxford University Press, New York, N.Y. pp. 547-606.

A "control plant" as used in the present invention refers to a plant cell, seed, plant component, plant tissue, plant organ or whole plant used to compare against transgenic or genetically modified plant for the purpose of identifying an enhanced phenotype in the transgenic or genetically modified plant. A control plant may in some cases be a transgenic plant line that comprises an empty vector or marker gene, but does not contain the recombinant polynucleotide of the present invention that is expressed in the transgenic or genetically modified plant being evaluated. In general, a control plant is a plant of the same line or variety as the transgenic or genetically modified plant being tested. A suitable control plant would include a genetically unaltered or non-transgenic plant of the parental line used to generate a transgenic plant herein.

A "transgenic plant" refers to a plant that contains genetic material not found in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding sequence operably linked (i.e., under regulatory control of) to an inducible regulatory sequence, such as a promoter of the invention, that allows for the controlled expression of polypeptide. The expression cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which expression of a polypeptide, such as a transcription factor polypeptide, is altered, e.g., in that it has been overexpressed or ectopically expressed.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to a form of water deficit such as drought, or particular salt or sugar concentrations, or by the observation of the expression level of a gene or genes, e.g., by employing Northern analysis, RT-PCR, microarray gene expression assays, or reporter gene expression systems, or by agricultural observations such as extent of wilting, turgor, hyperosmotic stress tolerance or yield. Any technique can be used to measure the amount of, comparative level of, or difference in any selected chemical compound or macromolecule in the transgenic plants, however.

"Trait modification" refers to a detectable difference in a characteristic in a plant ectopically expressing a polynucleotide or polypeptide of the present invention relative to a plant not doing so, such as a wild-type plant. In some cases, the trait modification can be evaluated quantitatively. For example, the trait modification can entail at least about a 2% increase or decrease, or an even greater difference, in an observed trait as compared with a control or wild-type plant. It is known that there can be a natural variation in the modified trait. Therefore, the trait modification observed entails a change of the normal distribution and magnitude of the trait in the plants as compared to control or wild-type plants.

When two or more plants are "morphologically similar" they have comparable forms or appearances, including analogous features such as dimension, height, width, mass, root mass, shape, glossiness, color, stem diameter, leaf size, leaf dimension, leaf density, internode distance, branching, root branching, number and form of inflorescences, and other macroscopic characteristics at a particular stage of growth. If the plants are morphologically similar at all stages of growth, they are also "developmentally similar". It may be difficult to distinguish two plants that are genotypically distinct but morphologically similar based on morphological characteristics alone.

The term "transcript profile" refers to the expression levels of a set of genes in a cell in a particular state, particularly by comparison with the expression levels of that same set of genes in a cell of the same type in a reference state. For example, the transcript profile of a particular transcription factor protein in a suspension cell is the expression levels of a set of genes in a cell knocking out or overexpressing that transcription factor protein compared with the expression levels of that same set of genes in a suspension cell that has normal levels of that transcription factor protein. The transcript profile can be presented as a list of those genes whose expression level is significantly different between the two treatments, and the difference ratios. Differences and similarities between expression levels may also be evaluated and calculated using statistical and clustering methods.

"Ectopic expression or altered expression" in reference to a polynucleotide indicates that the pattern of expression in, e.g., a transgenic plant or plant tissue, is different from the expression pattern in a wild-type plant or a reference plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more transcription factor proteins are under the control of a strong promoter (e.g., the cauliflower mosaic virus 35S transcription initiation region). Overexpression may also under the control of an inducible promoter such as a water deficit-inducible promoter. Thus, overexpression may occur throughout a plant or in the presence of particular environmental signals, depending on the promoter used.

Overexpression may take place in plant cells normally lacking expression of polypeptides functionally equivalent or identical to a polypeptide that can confer increased water deficit tolerance. Overexpression may also occur in plant cells where endogenous expression of the present proteins that confer enhanced water deficit tolerance, or functionally equivalent molecules, normally occurs, but such normal expression is at a lower level. Overexpression thus results in a greater than normal production, or "overproduction" of the protein that confers improved water deficit tolerance in the plant, cell or tissue.

The term "transcription regulating region" refers to a DNA regulatory sequence that regulates expression of one or more genes in a plant when a transcription factor having one or more specific binding domains binds to the DNA regulatory sequence. Transcription factors of the present invention possess an conserved domain. Transcription factors of the invention also comprise an amino acid subsequence that forms a transcription activation domain that regulates expression of one or more biotic stress resistance genes in a plant when the transcription factor binds to the regulating region.

DESCRIPTION OF THE SPECIFIC EMBODIMENTS

A number of polypeptides produced by plants are involved in numerous pathways that can confer enhanced tolerance to water deprivation. We have shown that overexpression of transcription factors can lead to enhanced water deficit tolerance in *Arabidopsis* plants. However, overexpression of these transcription factors may come at a price; the overexpressing plant may be small, may have increased disease susceptibility, or may have other undesirable developmental effects such as delayed development, low yield or fertility. This raises an obvious question: can regulation of transcription factor pathways be controlled in a manner that confers water deficit tolerance and yet avoids much or all of the growth and developmental penalty? Overexpression and associated water deficit tolerance without significant adverse morphological effects would make these transcription factors available as effective commercial tools for enhancing water deficit tolerance. One such means is the use of drought-inducible promoters that can confer water deficit tolerance while mitigating the undesirable effects of constitutive overexpression of transcription factors responsible for that tolerance.

The development of effective water deficit tolerance in these plants is likely to require a promoter(s) that responds rapidly to low water availability, as well as sustained expression throughout the period of low water availability to maximize effectiveness. The selection strategy for identifying commercially valuable drought-inducible promoters thus considered the following criteria. Promoters of interest would be:

- expressed at a low basal level, that is, in the absence of water deficit;
- induced strongly and at a sustained induction level early in the course of reduced water availability; and
- specific to the response to water deficit (the ability to be induced by other environmental factors increases frequency of expression and the likelihood that the plant would have reduced size or yield).

Transcript profiling (TxP) is a powerful tool for promoter discovery, providing a global insight into gene expression, regulation and induction levels in the plant's response to water deficit. As outlined below, water deficit-inducible promoters have been identified in microarrays by transcript profiling of plants exposed to water deficit-related challenges. When a polynucleotide sequence that encodes a polypeptide (for example, a transcription factor) known to confer water deficit tolerance but which also causes significant adverse morphological consequences was overexpressed, and the polynucleotide expression was under the regulatory control of water deficit-inducible promoters, the result was often the production of water deficit tolerance plants of normal (i.e., wild type) or near-normal stature and development.

Promoters showing early induction in a water deficit-related stress and little or no background expression could be used to drive expression of transcription factors to provide enhanced water deficit tolerance with little yield loss ("drag"). Promoters of genes that are induced relatively late in responding to water deficit are less likely to be effective, since they reflect a late induction of response factors. Therefore, we concentrated on early time points and early events following recognition of water deficit-derived stress response proteins.

Promoters of the invention are provided as SEQ ID NO: 1-9, and examples of expression vectors that have been or may be constructed using these promoters that may be able to confer improved water deficit tolerance include SEQ ID NOs: 10-54. The invention also encompasses a water deficit-inducible promoter that comprises a functional part of any of SEQ ID NOs: 1-9, provided that the functional part of the promoter also includes a water-deficit-inducible promoter function. The functional part of the promoter may have about 100, 150, 200, 250, 300, 350, 400, 447, 450, 460, 500, 550, 600, 605, 650, 700, 750, 766, 776, 780, 800, 850, 900, 907, 928 or 936 contiguous nucleotides of the nucleic acid sequences of SEQ ID NOs: 1-9, as well as all lengths of contiguous nucleotides within such sizes, provided that the functional part of the promoter includes a water-deficit-inducible promoter function.

Promoters that are similar to those listed in the Sequence Listing may be made that have some alterations in the nucleotide sequence and yet retain the function of the listed sequences. At the nucleotide level, the promoter sequences of the invention will typically share at least about 90%, 91%, 92%, 93%, 94%, 95%, 96%, 97%, 98%, 99% or 100% nucleotide sequence identity with any of SEQ ID NOs: 1-9, or with constructs SEQ ID NOs: 10-54.

Percent identity can be determined electronically, e.g., by using the MEGALIGN program (DNASTAR, Inc. Madison, Wis.). The MEGALIGN program can create alignments between two or more sequences according to different methods, for example, the clustal method (see, for example, Higgins and Sharp (1988). The clustal algorithm groups sequences into clusters by examining the distances between all pairs. The clusters are aligned pairwise and then in groups. Other alignment algorithms or programs may be used, including FASTA, BLAST, or ENTREZ, FASTA and BLAST, and which may be used to calculate percent similarity. These are available as a part of the GCG sequence analysis package (University of Wisconsin, Madison, Wis.), and can be used with or without default settings. ENTREZ is available through the National Center for Biotechnology Information. In one embodiment, the percent identity of two sequences can be determined by the GCG program with a gap weight of 1 (see U.S. Pat. No. 6,262,333).

Software for performing BLAST analyses is publicly available, e.g., through the National. Center for Biotechnology Information (see the world wide web internet website at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990); Altschul et al. (1993)). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always 0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved. value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989)). Unless otherwise indicated for comparisons of predicted polynucleotides, "sequence identity" refers to the % sequence identity generated from a tblastx using the NON version of the algorithm at the default settings using gapped alignments with the filter "off" (see, for example, the world wide web internet website at ncbi.nlm.nih.gov),

EXAMPLES

Example I

Microarray Time Course Experiments and Selection Criteria

Candidate drought-inducible promoters were primarily selected based on a drought time course TxP experiment performed. In this experiment, clay pots of well-watered late-rosette stage *Arabidopsis* plants grown under short day conditions were transferred to absorbent paper, and further watering was withheld during the subsequent drought period. Data were generated for five physiologically determined drought stages: mild stress, moderate stress, severe stress, and two stages after re-watering. The stress state of each plant was determined by measuring physiological indicators of drought, including relative water content, photosynthetic carbon assimilation, as well as ABA and proline levels. Leaf tissue samples during a two week drought period were collected daily, and sample from plants that had similar physiology for each pre-defined state were pooled for microarray analysis. Well-watered controls were also sampled each day. For each of the five physiological states analyzed, one microarray replicate consisted of leaf tissue pooled from six plants (18 leaves). Two replicates of each drought stage were analyzed on microarrays, and the resulting data were averaged. Expression ratios were generated by comparing each drought stage sample to an appropriate (age-matched) well-watered control.

Promoter candidates were selected based on the following criteria: 1) strong expression during at least moderate and severe stages of water deficit, and a return to well-watered baseline levels within 24 hr of re-watering, 2) low basal expression level in most non-stressed *Arabidopsis* tissues, and 3) similar drought inducibility for orthologous soybean genes, if these data were available.

Example II

Drought-Induction of Native Candidate Promoter Genes

Drought-inducible promoter candidates were initially identified based on a wild-type baseline drought transcription profile (TxP) experiment. In assessing the effectiveness of drought-inducible-transcription factor combinations, it was essential to ensure that the drought imposed on plants during the water deficit treatment (we used a clay pot, soil-based drought assay) was sufficient to drive inducible gene expression via the promoters in a similar manner as observed in the original drought TxP experiment. The nine endogenous genes in FIG. 3 showed strong induction upon drought treatment. These results confirmed that the clay pot soil-based drought assay was sufficient for water deficit-based induction of promoter candidate genes. Most of these genes are expressed at undetectable or extremely low levels in non-stressed plants. In most cases, however, there is considerably high expression in maturing seeds, due to the drought-like drying process inherent during this developmental stage. Additionally, several of the genes showed a response to ABA, osmotic, or cold treatment. Only one gene (AT3G46230) showed a response to heat treatment. This gene encodes a 17.4 kDa heat shock protein, so it is not surprising that in addition to drought induction, this gene also shows temperature regulation.

Drought stressed and well-watered pMen65 empty vector control plants were examined for induction of the candidate promoter genes on the x-axis of FIG. 3. Plants were drought stressed to the wilting point and RT-PCR was performed using gene-specific primers for each of the genes indicated on the x-axis of FIG. 3. Cycle threshold counts were normalized with 18S RNA.

Example III

Preparation of Transgenic Plants

Promoter Cloning.

For genes showing appropriate patterns of regulation, approximately 1.2 kb of upstream sequence were cloned by PCR (unless this region contained another gene, in which case the upstream sequence up to the next gene was cloned). Each promoter was cloned into an expression vector (vectors used in this study may include SEQ ID NOs: 10-54, and SEQ ID NO: 10-27, 33-36, 43-45, and 51-54 have been tested in plants) in front of either green fluorescent protein (GFP) or a polynucleotide encoding a transcription factor, such as SEQ ID NOs: 55, 57, 59, 61, or 59, that has been shown to provide increased tolerance to water deficit. In some of these cases, the transcription factors also produce deleterious morphological effects in the plants when they are constitutively overexpressed.

Transformation.

Transformation of *Arabidopsis* was performed by an *Agrobacterium*-mediated protocol based on the method of Bechtold and Pelletier (1998) *Methods Mol. Biol.* 82: 259-266. Unless otherwise specified, all experimental work was performed using the Columbia ecotype.

Plant Preparation.

*Arabidopsis* seeds were sown on mesh covered pots. The seedlings were thinned so that 6-10 evenly spaced plants remained on each pot 10 days after planting. The primary bolts were cut off a week before transformation to break apical dominance and encourage auxiliary shoots to form. Transformation was typically performed at 4-5 weeks after sowing.

Bacterial Culture Preparation.

*Agrobacterium* stocks were inoculated from single colony plates or from glycerol stocks and grown with the appropriate antibiotics and grown until saturation. On the morning of transformation, the saturated cultures were centrifuged and bacterial pellets are re-suspended in Infiltration Media (0.5× MS, 1×B5 Vitamins, 5% sucrose, 1 mg/ml benzylaminopurine riboside, 200 µl/L Silwet L77) until an A600 reading of 0.8 was reached.

Transformation and Seed Harvest.

The *Agrobacterium* solution was poured into dipping containers. All flower buds and rosette leaves of the plants were immersed in this solution for 30 seconds. The plants were laid on their side and wrapped to keep the humidity high. The plants were kept this way overnight at 4° C. and then the pots were turned upright, unwrapped, and moved to the growth racks.

The plants were maintained on the growth rack under 24-hour light until seeds were ready to be harvested. Seeds were harvested when 80% of the siliques of the transformed plants were ripe (approximately 5 weeks after the initial transformation). This seed was deemed T0 seed, since it was obtained from the T0 generation, and was later plated on selection plates (either kanamycin or sulfonamide). Resistant plants that were identified on such selection plates comprise the T1 generation.

For polynucleotides encoding transcription factors used in these experiments (SEQ ID NOs: 55, 57, 59, 61 or 63, encoding SEQ ID NOs: 56, 58, 60, 62 or 64, respectively), RT-PCR may be performed to confirm the ability of cloned promoter fragments to drive expression of the transcription factor transgene in plants transformed with the vectors.

T1 plants transformed with promoter-TF combinations listed in the Sequence Listing (those designated with a construct designation (SEQ ID NO: 10-27, 33-36, 43-45, and 51-54), were subjected to morphological analysis. Promoters that produced a substantial amelioration of the negative effects of TF overexpression were subjected to further analysis by propagation into the T2 generation, where the plants were analyzed for water deficit tolerance.

Example IV

GFP Fusion Expression Patterns

While the majority of cloned promoter fragments were shown to have the necessary sequences to drive drought-inducible expression of RNA, it was unknown if the elements required for efficient protein translation during stress were also included in these constructs. To assess this, promoter-GFP fusions were used to measure visually the accumulation of GFP protein during and after water deficit treatment. All nine promoters were examined, and three promoters in particular, prAT1G52690 (from a LEA protein), prAT5G52300 (from RD29B), and prAt5G43840 (from heat shock TF G1947), were found to drive high levels of detectable protein during water deficit stress.

The promoter from prAT1G52690 (SEQ ID NO: 4) was reliably and strongly induced upon drought in multiple events. The expression level, as measured by GFP fluorescence, was stronger than that of either the constitutively expressed cauliflower mosaic (CaMV) 35S promoter or the RD29A stress-inducible promoter. Upon re-watering, there was a slight decrease in the expression level over time, but levels were still well-above background expression. In terms of tissue-specific expression, in addition to leaves, this promoter was found to drive expression in flowers, especially floral guard cells.

Promoter prAT5G52300 from AT5G52300 (RD29B; SEQ ID NO: 2), produced some variable penetrance, but lines could be obtained that produced relatively stronger expression upon induction than either constitutive 35S or stress-inducible RD29A reference promoters. This indicates that the promoter from prAT5G52300 may be easily influenced by the insertion point in the genome. Expression from this promoter was persistent after re-watering, and, except for expression in leaves, no tissue-specific expression was noted.

Promoter prAt5G43840 from At5G43840 (heat shock TF G1947; SEQ ID NO: 6) also produced variably penetrant lines in terms of strong drought-inducibility, but again, strong lines could be isolated. The expression from this promoter was very slightly weakened after re-watering, and except for leaf tissue no tissue-specific expression was noted.

Example V

Promoter-G481 Fusion Expression Patterns

These experiments, conducted with the G481 protein (SEQ ID NO: 56) illustrate the types of experiments that can be used to identify promoters that effectively induce water deficit-related protein expression.

In addition to characterizing the ability of these promoters to drive GFP protein expression, the drought-inducible accumulation of the G481 protein was also examined in lines transformed with three different promoter-G481 combinations, the promoters being prAT1G52690 (SEQ ID NO: 4), prAT5G52300 (SEQ ID NO: 2), and prAT2G37870 (SEQ ID NO: 5). The first two of these promoters, prAT1G52690 and prAT5G52300, had shown strong GFP induction when *Arabidopsis* plants were subjected to drought treatment. Protein from well-watered or drought-treated plants was subjected to gel electrophoresis and the gels were then probed with an antibody to the G481 protein. Coomassie blue staining was used to verify equivalent protein loading. G481 was found to accumulate to high levels upon water deficit treatment when expressed under the regulatory control of either prAT1G52690 or prAT5G52300, similar to what was expected from GFP experiments in which it was shown that either of these promoters effectively induced G481 expression. The third promoter tested (G481 under the regulatory control of prAT2G37870), did not provide significant drought-inducible G481 protein expression. Again, this result is similar to what was observed with GFP experiments.

Example VI

Soil-Based Water Deficit Assays

The soil-based water deficit assays (also referred to as "drought assays") were performed in clay pots and were based on the procedure described by Haake et al. (2002) *Plant Physiol.* 130: 639-648.

Seeds were sterilized by a 2 minute ethanol treatment followed by 20 minutes in 30% bleach/0.01% Tween and five washes in distilled water. Seeds were sown on MS agar in 0.1% agarose and stratified for 3 days at 4° C., before transfer to growth cabinets with a temperature of 22° C. After 7 days of growth on selection plates, seedlings were transplanted to 3.5 inch diameter clay pots containing 80 g of a 50:50 mix of vermiculite:perlite topped with 80 g of ProMix. Typically, each pot contained 14 seedlings, and plants of the transgenic line being tested were in separate pots to the wild-type controls. Pots containing the transgenic line versus control pots were interspersed in the growth room, maintained under 24-hour light conditions (18-23° C., and 90-100 $\mu Em^{-2}s^{-1}$) and watered for a period of 14 days. Water was then withheld and pots were placed on absorbent paper for a period of 8-10 days. After this period, a visual qualitative "drought score" from 0-6 was assigned to record the extent of visible drought stress symptoms. A score of "6" corresponded to no visible symptoms whereas a score of "0" corresponded to extreme wilting and the leaves having a "crispy" texture. At the end of the drought period, pots were re-watered and scored after 5-6 days; the number of surviving plants in each pot was counted, and the proportion of the total plants in the pot that survived was calculated.

Analysis of Results.

Typically, 6 or more pots of a transgenic line were compared with 6 or more pots of the appropriate control plants. The mean drought score and mean proportion of plants surviving (survival rate) were calculated for both the transgenic line and the wild-type pots. In each case, a p-value that indicated the significance of the difference between the two mean values was calculated. The results for each transgenic line across each planting for a particular project were then presented in a results table.

Calculation of p-Values.

Survival was analyzed with a logistic regression to account for the fact that the random variable was a proportion between 0 and 1. The reported p-value was the significance of the experimental proportion contrasted to the control, based upon regressing the logit-transformed data.

Drought score, being an ordered factor with no real numeric meaning, was analyzed with a non-parametric test between the experimental and control groups. The p-value was calculated with a Mann-Whitney rank-sum test. Significance was indicated if the experimental line performed better or worse than controls at p<0.11.

Example VII

Water Deficit Tolerance of Transgenic Plants Transformed with Transcription Factors Under the Regulatory Control of Drought-Inducible Promoters Generally, for the water deficit assays described in this example, three lines of overexpressors were tested, and the results are presented if they were determined to be statistically significant (p<0.11). In a typical set of experiments, lines that were wild-type in appearance were chosen for soil drought assays, except as noted below.

G481 (SEQ ID NOs: Polynucleotide 55 and Polypeptide 56)

G481 is a CAAT family transcription factor sequence that has been shown to confer improved drought tolerance when constitutively expressed. However, unwelcome morphological or physical characteristics may be associated with constitutive overexpression of G481 (for example, late flowering). It is believed that a drought-inducible promoter regulating G481 expression may provide drought tolerance in plants, as well as a normal morphology and development.

Lines for each promoter-G481 combination generally appeared wild-type, although some lines showed changes in flowering time, possibly indicating low level background expression of G481.

In general, many of the drought inducible promoter-G481 combinations performed no better or worse than controls in water deficit experiments. However, some lines for five of the constructs tested (prAT5G15240, prG1947, prAT5G66780, prAT3G46230, and prAT2G37870) were shown to be more tolerant to water deficit than controls on at least one of two plant dates, as noted below.

One line of prAT5G15240::G481 overexpressors recovered from water deficit treatment better than controls in one of two runs of the assay. No obvious induction of the G481 transgene was evident in an RT-PCR experiment.

One line of prG1947::G481 overexpressors was more tolerant to water deficit treatment in one of two runs of the assay. Drought induction of the G481 transgene was seen in the RT-PCR experiment.

One line of prAT3G46230::G481 overexpressors recovered from water deficit treatment better than controls in one of two runs of the assay. Very mild drought induction of the G481 transgene was seen in the RT-PCR experiment.

One line of prAT5G66780::G481 overexpressors was statistically more tolerant to water deficit treatment in one of two runs and a separate planting of this line recovered from water deficit treatment better than controls. Drought induction of the G481 transgene was seen in the RT-PCR experiment Two lines of prAT2G37870::G481 overexpressors demonstrated a statistically better performance in drought assays than controls on separate planting dates. For the first line, plants from one of the planting dates were both more tolerant to water deficit than controls and recovered better than controls. For the second line, plants in two separate experiments were more tolerant to water deficit than controls and/or recovered better from the treatment than controls. Drought induction of the G481 transgene has not been examined by RT-PCR.

G1073 (SEQ ID NOs: Polynucleotide 57 and Polypeptide 58)

G1073 is a member of the AT-hook family transcription factors and has been shown to confer improved drought tolerance when constitutively expressed. However, unwelcome morphological or physical characteristics such as large size (which may be a disadvantage under some circumstances) may be associated with constitutive overexpression of G1073. It is believed that a drought-inducible promoter regulating G1073 expression may provide drought tolerance in plants, as well as a more normal morphology and development.

T2 lines tested in clay pot drought assays for the different promoter-G1073 combinations generally appeared wild-type. However, in the T1 generation, modest alterations in flowering time and size were observed for some of the constructs, possibly indicating low level background expression of G1073.

In general, many of the drought inducible promoter-G1073 combinations performed no better or worse than controls in water deficit experiments. However, a number of individual lines for five of the constructs did show a better performance than controls on at least one of two plant dates (prAT5G15240, prAT5G66780, prG1947, prAT3G17520 and prAT5G52300).

One line of prAT5G15240::G1073 overexpressors recovered better from a water deficit treatment in one of two runs of the assay. No induction of the G1073 transgene was observed in RT-PCR experiments.

One line of prAT5G66780::G1073 overexpressors recovered better from a water deficit treatment in one of two runs of the assay. Induction of the G1073 transgene by the drought treatment was confirmed by RT-PCR.

One line of prG1947::G1073 overexpressors performed better than controls in the water deficit tolerance and in their recovery from the treatment in one of two runs of the assay. Induction of the G1073 transgene by the drought treatment was confirmed by RT-PCR.

One line of prAT3G17520::G1073 overexpressors recovered from water deficit better than controls in two separate experiments. Induction of the G1073 transgene by the drought treatment has been confirmed.

One line of prAT5G52300::G1073 overexpressors recovered from water deficit better than controls in one of two runs of the assay. Induction of the G1073 transgene by the drought treatment has been confirmed.

G1274 (SEQ ID NOs: Polynucleotide 59 and Polypeptide 60)

G1274 is a member of the WRKY family of transcription factors and has been shown to confer improved drought tolerance when constitutively expressed. However, unwelcome morphological or physical characteristics such as effects on size (both small and large plants have been observed, both of which may be disadvantageous under some circumstances) may be associated with constitutive overexpression of G1274. It is believed that a drought-inducible promoter regulating G1274 expression may provide drought tolerance in plants with more normal morphology and development.

Overall, the drought-inducible promoter-G1274 lines did not show any consistent differences from wild-type morphology, with the exception of some inconsistent variation in flowering time. Besides prAT5G15240, all other promoters were confirmed to produce drought-induced G1274 transcript, as measured by RT-PCR.

In general, many of the lines transformed with G1274 under the regulatory control of a drought-inducible promoter performed no better or even worse than controls in drought assays. However, a number of individual lines for three of the five constructs tested, prAT5G66780, prAT3G17520 and prAT4G09600 did show a better performance than controls in water deficit experiments on one of two plant dates, as noted below.

One line of prAT5G66780::G1274 overexpressors recovered from water deficit treatment better than controls in one of two runs of the assay. Induction of the G1274 transgene by the drought treatment was confirmed by RT-PCR.

In one of two runs of a water deficit assay, one of the prAT3G17520::G1274 lines of overexpressors recovered from water deficit better than controls. Induction of the G1274 transgene by the drought treatment was confirmed by RT-PCR.

One line of prAT4G09600::G1274 overexpressors also recovered from water deficit treatment better than controls in one of two runs of the assay. Induction of the G1274 transgene by the drought treatment was confirmed by RT-PCR.

G1792 (SEQ ID NOs: Polynucleotide 61 and Polypeptide 62)

G1792 is a member of the AP2 family transcription factors and has been shown to confer improved drought tolerance when constitutively expressed. However, unwelcome morphological or physical characteristics such as small size and reduced fertility may be associated with constitutive overexpression of G1792. It is believed that a drought-inducible promoter regulating G1792 expression may provide drought tolerance in plants with more normal morphology and development.

Lines for each promoter-G1792 combination generally appeared wild-type, although a minority of the T1 plants for each promoter showed dark green and/or late flowering phenotypes, indicating leaky expression of G1792 in these lines.

Lines for five different drought inducible promoters directly fused to G1792 have been through two runs of the soil drought clay pot assay. These drought inducible promoter combinations did not produce compelling results with G1792, and many lines performed the same, or worse, than controls in this water deficit assay. However, one line for one of the five constructs did show a better performance than controls on one of two plant dates, as noted below.

One line of prAT4G09600::G1792 overexpressors recovered from the water deficit treatment better than controls in one of two runs of the assay. Drought induction of the G1792 transgene was seen in the RT-PCR experiment.

G47 (SEQ ID NOs: Polynucleotide 63 and Polypeptide 64)

G47 is a member of the AP2 family transcription factors and has been shown to confer improved drought tolerance when constitutively expressed. However, unwelcome morphological or physical characteristics such as small size and reduced fertility may be associated with constitutive overexpression of G47. It is believed that a drought-inducible promoter regulating G47 expression may provide drought tolerance in plants with more normal morphology and development.

Two of the promoter-G47 combinations tested, prAT5G66780, prG1947, resulted in plants that were somewhat late developing, possible indicating leaky expression of G47 in these lines.

Lines for five different drought inducible promoters directly fused to G47 were tested in two runs of the soil drought clay pot assay. A number of individual lines for four of the five constructs, comprising prAT5G15240, prAT3G17520, prAT4G09600 and prG1947, showed a better performance than controls on at least one of two plant dates, as noted below.

One line of prAT5G15240::G47 overexpressors recovered better from a water deficit treatment, and another line was visibly more tolerant and recovered better from the water deficit treatment than control plants in one of two runs of the assay. Drought-based induction of the G47 transgene was not confirmed by RT-PCR.

One line of prAT3G17520::G47 overexpressors recovered better from a water deficit treatment than controls in one of two runs of the assay. Induction of the G47 transgene by the drought treatment was confirmed by RT-PCR.

One line of prAT4G09600::G47 overexpressors recovered better from a water deficit treatment than controls in one of two runs of the assay. A second line was visibly more tolerant to water deficit (observed in one run of the assay) and recovered better from the treatment than control plants (observed in both runs of the assay). Induction of the G47 transgene by the drought treatment was confirmed by RT-PCR.

One line of prG1947::G47 overexpressors recovered better from a water deficit treatment than controls in one of two runs of the assay. A second line was visibly more tolerant to water deficit and recovered better from the treatment than control plants in one of the two runs of the assay. Induction of the G47 transgene by the drought treatment was confirmed by RT-PCR in the former of these lines but did not confirm induction in the latter.

Example VIII

Regulating Expression of Polynucleotides Encoding RNA Species Which Act at a Non-Protein Level In addition to use of the water deficit inducible promoters to regulate the expression of a polynucleotide encoding a polypeptide, these promoters can also be used to regulate the expression of a polynucleotide encoding a non-coding RNA species (that is, one which acts at a non-protein level), such as a microRNA, a microRNA precursor, or a sequence designed to act through RNA interference (RNAi). For example, a substantial number of microRNA (miRNA) species have been implicated in stress responses and these molecules have been shown to be involved in the control of many aspects of plant growth and development (Bartel and Bartel (2003) *Plant Physiol.* 132: 709-717; Aukerman and Sakai (2003). *Plant Cell* 15: 2730-2741; Bartel (2004) *Cell* 116: 281-297; Juarez et al. (2004) *Nature* 428: 84-88; Bowman (2004) *Bioessays* 26: 938-942; Sunkar and Zhu (2004) *Plant Cell* 16: 2001-2019).

It should be noted that, for particular families of highly related plant transcription factors, overexpression of one or more of the family members produces a comparable phenotype to that obtained from reducing expression (for example, by mutation or knockdown approaches such as antisense or RNA interference) of one or more of the family members. For instance, overexpression of the CBF family proteins has been widely demonstrated to confer tolerance to drought and low temperature stress (e.g., Jaglo et al. (2001) *Plant Physiol.* 127: 910-917). Nonetheless, Novillo et al. (2004) *Proc. Natl. Acad. Sci. USA* 101: 3985-3990, showed that homozygous cbf2 mutant *Arabidopsis* plants carrying a disruption in the CBF2 gene also exhibit enhanced freezing tolerance. Such results can be accounted for by cross regulation between the genes encoding different transcription factor family members. In the study by Novillo et al, (2004) supra, CBF2 was shown to be a negative transcriptional regulator of the CBF1 and CBF3 genes. Comparable mechanisms likely account for the fact that we have observed stress tolerance from both overexpression and from knockdown approaches with certain NF-Y family genes.

We have shown using a 35S promoter that overexpression of precursors for miRNA169 (SEQ ID NOs: 71, 72, 73 or 74), which targets NF-YA (HAP2 class transcription factor genes; Bartel and Bartel, supra; Jones-Rhoades and Bartel (2004) *Mol. Cell* 14: 787-799) produces tolerance to dehydration and osmotic stress, but this is often accompanied by developmental changes such as alterations in flowering time or reduced size. Expression of miRNA169 using a drought inducible promoter is therefore expected to produce water deficit tolerance without undesirable effects on development. We have obtained similar results from overexpression of a polynucleotide (P21305, SEQ ID NO: 66) designed to effect RNA interference on Non-LEC1-like NF-YB proteins; The RNAi construct P21305 (carrying KanR) targets the G481 clade (this clade is comprised of sequences that are closely and evolutionarily related to G481, SEQ ID NO: 55 encoding polypeptide SEQ ID NO: 56). It contains two fragments each comprised of G481 clade sequences from G2345, SEQ ID NO: 67 (base pairs 185-315 from the start codon; this fragment is represented by SEQ ID NO: 69) and G485 SEQ ID NO: 68 (base pairs 61-170 from the start codon, this fragment is represented by SEQ ID NO: 70). A number of bases were mutated in order to increase the percentage homology with the other clade members. The bases that appear as capital letters in the two sequence fragments listed below indicate positions where the point mutations were introduced in the cloning primers to increase the percentage homology with other clade members.

G2345 fragment (bases 185-315),
SEQ ID NO: 69
aggaatgTgtctctgaAttcatcagcttcgtcaccagcgaggctagtgat aagtgccaaagagagaaAaggaagaccatcaatggagatgatttgctttg ggctatggccactttaggattCgaAgattac G485 fragment (bases 61-170),
SEQ ID NO: 70
gagcaagataggtttctAccgatcgctaacgttagcaggatcatgaagaa agcacttcctgcgaacgcaaaaatctctaaGgatgcTaaagaAacggttc aagagtgtgt The fragments are expected to form a hairpin structure as follows: 35S::sense_fragment(G2345-G485)::pdkintron::antisense_fragment(G2345-G485). Transgenic *Arabidopsis* lines overexpressing P21305 showed improved tolerance to water deficit and heat stress, but exhibited developmental abnormalities and changes in flowering time. Expression of such a polynucleotide using a drought inducible promoter is therefore expected to produce stress tolerance without undesirable effects on development and/or morphology.

Example IX

Transformation of Dicots to Produce Increased Water Deficit Stress Tolerance

Crop species including tomato and soybean plants that overexpress transcription factor polypeptides that confer increased tolerance to water deficit, including dehydration, desiccation, drought or another hyperosmotic stress such as high salt or sugar concentrations, may produce plants with increased water deficit tolerance when placed under the regulatory control of water deficit-inducible promoters of the invention. These observations indicate that these genes, when overexpressed, will result in improved quality and larger yields than non-transformed plants in stressed conditions, which may occur in the field to even a low, imperceptible degree at any time in the growing season.

Thus, promoter sequences listed in the Sequence Listing recombined into, for example, one of the expression vectors of the invention, or another suitable expression vector, may be transformed into a plant for the purpose of regulating water response sequences and modifying plant traits for the purpose of improving yield and/or quality. The cloning vector may be introduced into a variety of plants by means well known in the art such as, for example, direct DNA transfer or *Agrobacterium tumefaciens*-mediated transformation. It is now routine to produce transgenic plants using most dicot plants (see Weissbach and Weissbach, (1989) *Methods for Plant Molecular Biology*, Academic Press; Gelvin et al. (1990) *Plant Molecular Biology Manual*, Kluwer Academic Publishers; Herrera-Estrella et al. (1983) *Nature* 303: 209; Bevan (1984) *Nucleic Acids Res.* 12: 8711-8721; and Klee (1985) *Bio/Technology* 3: 637-642). Methods for analysis of traits are routine in the art and examples are disclosed above.

Numerous protocols for the transformation of tomato and soy plants have been previously described, and are well known in the art. Gruber et al. (1993) in *Methods in Plant Molecular Biology and Biotechnology*, p. 89-119, and Glick and Thompson ((1993) *Methods in Plant Molecular Biology and Biotechnology*. CRC Press., Boca Raton, Fla.) describe several expression vectors and culture methods that may be used for cell or tissue transformation and subsequent regeneration. For soybean transformation, methods are described by Miki et al. (1993) in *Methods in Plant Molecular Biology and Biotechnology*, p. 67-88, Glick and Thompson, eds., CRC Press, Inc., Boca Raton; and U.S. Pat. No. 5,563,055, (Townsend and Thomas), issued Oct. 8, 1996.

There are a substantial number of alternatives to *Agrobacterium*-mediated transformation protocols, other methods for the purpose of transferring exogenous genes into soybeans or tomatoes. One such method is microprojectile-mediated transformation, in which DNA on the surface of microprojectile particles is driven into plant tissues with a biolistic device (see, for example, Sanford et al. (1987) *Part. Sci. Technol.* 5:27-37; Christou et al. (1992) *Plant. J.* 2: 275-281; Sanford (1993) *Methods Enzymol.* 217: 483-509; Klein et al. (1987) *Nature* 327: 70-73; U.S. Pat. No. 5,015,580 (Christou et al), issued May 14, 1991; and U.S. Pat. No. 5,322,783 (Tomes et al.), issued Jun. 21, 1994).

Alternatively, sonication methods (see, for example, Zhang et al. (1991) *Bio/Technology* 9: 996-997); direct uptake of DNA into protoplasts using CaCl2 precipitation, polyvinyl alcohol or poly-L-ornithine (Hain et al. (1985) *Mol. Gen. Genet.* 199: 161-168; Draper et al. (1982) *Plant Cell Physiol.* 23: 451-458); liposome or spheroplast fusion (see, for example, Deshayes et al. (1985) *EMBO J.*: 4: 2731-2737; Christou et al. (1987) *Proc. Natl. Acad. Sci. USA* 84: 3962-3966); and electroporation of protoplasts and whole cells and tissues (see, for example, Donn et al. (1990) in *Abstracts of VIIth International Congress on Plant Cell and Tissue Culture IAPTC*, A2-38: 53; D'Halluin et al. (1992) *Plant Cell* 4: 1495-1505; and Spencer et al. (1994) *Plant Mol. Biol.* 24: 51-61) have been used to introduce foreign DNA and expression vectors into plants.

After a plant or plant cell is transformed (and the latter regenerated into a plant), the transformed plant may be crossed with itself or a plant from the same line, a non-transformed or wild-type plant, or another transformed plant from a different transgenic line of plants. Crossing provides the advantages of producing new and often stable transgenic varieties. Genes and the traits they confer that have been introduced into a tomato or soybean line may be moved into distinct line of plants using traditional backcrossing techniques well known in the art. Transformation of tomato plants may be conducted using the protocols of Koornneef et al (1986) in *Tomato Biotechnology*: Alan R. Liss, Inc., 169-178, and in U.S. Pat. No. 6,613,962, the latter method described in brief here. Eight day old cotyledon explants are precultured for 24 hours in Petri dishes containing a feeder layer of Petunia hybrida suspension cells plated on MS medium with 2% (w/v) sucrose and 0.8% agar supplemented with 10 µM α-naphthalene acetic acid and 4.4 µM 6-benzylaminopurine. The explants are then infected with a diluted overnight culture of *Agrobacterium tumefaciens* containing an expression vector comprising a polynucleotide of the invention for 5-10 minutes, blotted dry on sterile filter paper and cocultured for 48 hours on the original feeder layer plates. Culture conditions are as described above. Overnight cultures of *Agrobacterium tumefaciens* are diluted in liquid MS medium with 2% (w/v/) sucrose, pH 5.7) to an OD600 of 0.8.

Following cocultivation, the cotyledon explants are transferred to Petri dishes with selective medium comprising MS medium with 4.56 µM zeatin, 67.3 µM vancomycin, 418.9 µM cefotaxime and 171.6 µM kanamycin sulfate, and cultured under the culture conditions described above. The explants are subcultured every three weeks onto fresh medium. Emerging shoots are dissected from the underlying callus and transferred to glass jars with selective medium without zeatin to form roots. The formation of roots in a kanamycin sulfate-containing medium is a positive indication of a successful transformation.

Transformation of soybean plants may be conducted using the methods found in, for example, U.S. Pat. No. 5,563,055 (Townsend et al., issued Oct. 8, 1996), described in brief here. In this method soybean seed is surface sterilized by exposure to chlorine gas evolved in a glass bell jar. Seeds are germinated by plating on 1/10 strength agar solidified medium without plant growth regulators and culturing at 28° C. with a 16 hour day length. After three or four days, seed may be prepared for cocultivation. The seedcoat is removed and the elongating radicle removed 3-4 mm below the cotyledons.

Overnight cultures of *Agrobacterium tumefaciens* harboring the expression vector comprising a polynucleotide of the invention are grown to log phase, pooled, and concentrated by centrifugation. Inoculations are conducted in batches such that each plate of seed was treated with a newly resuspended pellet of *Agrobacterium*. The pellets are resuspended in 20 ml inoculation medium. The inoculum is poured into a Petri dish containing prepared seed and the cotyledonary nodes are macerated with a surgical blade. After 30 minutes the explants are transferred to plates of the same medium that has been solidified. Explants are embedded with the adaxial side up and level with the surface of the medium and cultured at 22° C. for three days under white fluorescent light. These plants may then be regenerated according to methods well established in the art, such as by moving the explants after three days to a liquid counter-selection medium (see U.S. Pat. No. 5,563,055).

The explants may then be picked, embedded and cultured in solidified selection medium. After one month on selective media transformed tissue becomes visible as green sectors of regenerating tissue against a background of bleached, less healthy tissue. Explants with green sectors are transferred to an elongation medium. Culture is continued on this medium with transfers to fresh plates every two weeks. When shoots are 0.5 cm in length they may be excised at the base and placed in a rooting medium.

Example X

Transformation of Monocots to Produce Increased Water Deficit Stress Tolerance

Cereal plants and other grasses such as, but not limited to, corn, wheat, rice, sorghum, barley, Miscanthus, and switchgrass may be transformed with the present promoter sequences such as those presented in the present Sequence Listing, cloned into a vector such as pGA643 and containing a kanamycin-resistance marker, and inducibly express, for example, a transcription factor that confers improved water deficit tolerance. The expression vectors may be one found in the Sequence Listing, or any other suitable expression vector that incorporates a promoter sequence of the invention, may be similarly used. For example, pMEN020 may be modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

The cloning vector may be introduced into a variety of cereal plants by means well known in the art including direct DNA transfer or *Agrobacterium tumefaciens*-mediated transformation. The latter approach may be accomplished by a variety of means, including, for example, that of U.S. Pat. No. 5,591,616, in which monocotyledon callus is transformed by contacting dedifferentiating tissue with the *Agrobacterium* containing the cloning vector.

The sample tissues are immersed in a suspension of 3×10-9 cells of *Agrobacterium* containing the cloning vector for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants are then analyzed for the presence of the NPTII gene/kanamycin resistance by ELISA, using the ELISA NPTII kit from 5Prime-3Prime Inc. (Boulder, Colo.).

It is also routine to use other methods to produce transgenic plants of most cereal crops (Vasil (1994) *Plant Mol. Biol.* 25: 925-937) such as corn, wheat, rice, sorghum (Cassas et al. (1993) *Proc. Natl. Acad. Sci. USA* 90: 11212-11216), and barley (Wan and Lemeaux (1994) *Plant Physiol.* 104: 37-48). DNA transfer methods such as the microprojectile method can be used for corn (Fromm et al. (1990) *Bio/Technol.* 8: 833-839; Gordon-Kamm et al. (1990) *Plant Cell* 2: 603-618; Ishida (1990)) *Nature Biotechnol.* 14:745-750, wheat (Vasil et al. (1992) *Bio/Technol.* 10:667-674; Vasil et al. (1993) *Bio/Technol.* 11:1553-1558; Weeks et al. (1993) *Plant Physiol.* 102:1077-1084), and rice (Christou (1991) *Bio/Technol.* 9:957-962; Hiei et al. (1994) *Plant J.* 6:271-282; Aldemita and Hodges (1996) *Planta* 199: 612-617; and Hiei et al. (1997) *Plant Mol. Biol.* 35:205-218). For most cereal plants, embryogenic cells derived from immature scutellum tissues are the preferred cellular targets for transformation (Hiei et al. (1997) supra; Vasil (1994) supra). For transforming corn embryogenic cells derived from immature scutellar tissue using microprojectile bombardment, the A188XB73 genotype is the preferred genotype (Fromm et al. (1990) supra; Gordon-Kamm et al. (1990) supra). After microprojectile bombardment the tissues are selected on phosphinothricin to identify the transgenic embryogenic cells (Gordon-Kamm et al. (1990) supra). Transgenic plants are regenerated by standard corn regeneration techniques (Fromm et al. (1990) supra; Gordon-Kamm et al. (1990) supra). *Agrobacterium*-mediated transformation of switchgrass has also been reported by Somleva et al. (2002) *Crop Sci.* 42: 2080-2087.

Example XI

Transcription Factor Expression and Analysis of Water Deficit Stress Tolerance Northern blot analysis, RT-PCR or microarray analysis of the regenerated, transformed plants may be used to show expression of a transcription factor polypeptide of the invention and related genes that are capable of inducing improved water deficit stress tolerance as compared to a control plant.

To verify the ability to confer increased water deficit tolerance, mature plants overexpressing a transcription factor under the regulatory control of a water deficit-inducible promoter of the invention, or alternatively, seedling progeny of these plants, may be challenged by a stress such as a dehydration, drought, desiccation, or a related hyperosmotic stress tolerance such as salt or mannitol. Alternatively, these plants may challenged in a hyperosmotic stress condition that may also measure altered sugar sensing, such as a high sugar (e.g., sucrose) condition. By comparing control plants (for example, wild type or parental line untransformed plants, or plants transformed with an empty vector or one lacking the transcription factor) and transgenic plants similarly treated, the transgenic plants may be shown to have greater tolerance to the particular water deficit-related stress.

After a dicot plant, monocot plant or plant cell has been transformed (and the latter regenerated into a plant) and shown to have greater size or tolerance to water deficit-related stress, or produce greater yield or quality relative to a control plant under the stress conditions, the transformed monocot plant may be crossed with itself or a plant from the same line, a non-transformed or wild-type monocot plant, or another transformed monocot plant from a different transgenic line of plants.

These experiments would demonstrate that transcription factor polypeptides of the invention can be identified and shown to confer greater water deficit-related stress tolerance, greater yield, or greater quality in dicots or monocots, including tolerance to more than one water deficit-related stresses.

Example XII

Sequences that Confer Significant Improvements to Non-*Arabidopsis* Species The function of promoter sequences of the invention has been analyzed and may be further characterized and the sequences may be incorporated into crop plants. The ectopic overexpression of transcription factor sequences, or any other sequence that may confer increased tolerance to water-deficit related stress (e.g., to drought, desiccation, dehydration and/or other hyperosmotic stress) may be regulated using regulatory elements of the invention. In addition to these sequences, it is expected that newly discovered polynucleotide sequences from, for example, other species having similar sequences, may be closely related to polynucleotide sequences found in the Sequence Listing can also confer improved water deficit tolerance in a similar manner to the sequences found in the Sequence Listing, when transformed into a any of a considerable variety of plants of different species, and including dicots and monocots. The polynucleotide and polypeptide sequences derived from monocots (e.g., the rice sequences) may be used to transform both monocot and dicot plants, and those derived from dicots (e.g., the *Arabidopsis* and soy genes) may be used to transform either group, although some of these sequences may function best if the gene is transformed into a plant from the same class as that from which the sequence is derived.

The results presented in the Examples above indicate that proteins such as transcription factors that confer improved water deficit tolerance may do so when they are overexpressed under the regulatory control of a promoter sequence of the invention, without having a significant adverse impact on plant morphology and/or development. The lines that display useful traits may be selected for further study or commercial development.

Monocotyledonous plants, including rice, corn, wheat, rye, sorghum, barley and others, may be transformed with a plasmid containing a transcription factor polynucleotide. The transcription factor gene sequence may include dicot or monocot-derived sequences such as those presented herein. These transcription factor genes may be cloned into an expression vector containing a kanamycin-resistance marker, and then expressed in an inducible manner under the regulatory control of a promoter sequence of the invention.

The cloning vector may be introduced into monocots by, for example, means described in the previous Example, including direct DNA transfer or *Agrobacterium tumefaciens*-mediated transformation. The latter approach may be accomplished by a variety of means, including, for example, that of U.S. Pat. No. 5,591,616, in which monocotyledon callus is transformed by contacting dedifferentiating tissue with the *Agrobacterium* containing the cloning vector.

The sample tissues are immersed in a suspension of $3 \times 10-9$ cells of *Agrobacterium* containing the cloning vector for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants are then analyzed for the presence of the NPTII gene/kanamycin resistance by ELISA, using the ELISA NPTII kit from 5Prime-3Prime Inc. (Boulder, Colo.).

Northern blot analysis, RT-PCR or microarray analysis of the regenerated, transformed plants may be used to show expression of a transcription factor polypeptide of the invention that is capable of conferring improved water deficit-related stress tolerance, or increased yield or quality, in the transformed plants.

To verify the ability to confer improved water deficit-related stress tolerance, mature plants or seedling progeny of these plants expressing a monocot-derived equivalog gene may be challenged using methods described herein. By comparing control plants and the transgenic plants, the latter are shown be more tolerant to one or more water deficit-related stresses such as drought, dehydration, desiccation, or other hyperosmotic stress, as compared to control plants similarly treated. As an example of a first step to determine water deficit-related tolerance, seeds of transgenic plants may be subjected to germination assays to measure sucrose sensing. For example, sterile dicot seeds including, but not limited to soybean and alfalfa, are sown on 80% MS medium plus vitamins with 9.4% sucrose; control media lack sucrose. All assay plates are then incubated at 22° C. under 24-hour light, 120-130 µEin/m2/s, in a growth chamber. Evaluation of germination and seedling vigor is then conducted three days after planting. Plants overexpressing proteins that confer improved tolerance to water deficit, where the proteins are under the regulatory control of promoters of the invention, may be found to be more tolerant to high sucrose by having better germination, longer radicles, and more cotyledon expansion, than control plants in the presence of the sugar concentration. It is expected that closely related and structurally similar promoter sequences, may also confer altered sugar sensing or improved hyperosmotic stress tolerance.

Plants overexpressing proteins that confer increased tolerance to water deficit, where the proteins are under the regulatory control of the promoter sequences of the invention, may also be subjected to soil-based drought assays to identify those lines that are more tolerant to water deprivation than control plants. For example, drought experiments in a greenhouse may be conducted. Pre-germinated seedlings of transgenic plants (progeny of a heterozygous transgenic plant that inherit the exogenous transcription factor DNA construct) and wild type plants (progeny of a heterozygous transgenic plant that inherit the exogenous transcription factor DNA construct) are planted in soil. The plants are well watered for one week and then allowed to dry for 4 days. An equal number of transgenic and wild type plants are selected based on matched height. A drought assay is then started by measuring plant heights and resuming daily watering for "wet" pots. "Dry" pots are generated by maintaining the average "dry" pot weight (e.g., about 400 g) well below that of the "wet" pots (e.g., about 500 g or more); water is added to the "dry" pots when necessary to maintain the "dry" pots at around the average "dry" pot weight. The height of transgenic plants and controls are measured for nine days, after which full watering is resumed for the "dry" flat pots for three days, after which heights are again measured. Recovered plants may be subjected to a second round of drought as described above. A number of the lines of plants transformed with sequences of the invention will be significantly larger and greener, with less wilting or desiccation, than control plants, particularly after a period of water deficit is followed by rewatering and a subsequent incubation period. Unlike plants constitutively overexpressing the proteins that confer increased tolerance to water deficit, transgenic plants overexpressing these proteins under the regulatory control of the water deficit-inducible promoters described herein will be morphologically and developmentally similar to control plants such as wild type or plants transformed with an "empty" vector.

It is expected that the same methods may be applied to identify other useful and valuable promoter sequences, and the sequences may be derived from a diverse range of species.

We claim:

1. A plant cell comprising a recombinant polynucleotide comprising a nucleotide sequence and a promoter that has water deficit-inducible promoter activity, wherein the promoter is operably linked to the nucleotide sequence to which it is not operably linked in nature, wherein said promoter has at least 98% identity to the polynucleotide sequence of SEQ ID NO: 6.

2. The plant cell of claim 1, wherein the recombinant polynucleotide comprises SEQ ID NO:15.

3. The plant cell of claim 1, wherein the recombinant polynucleotide comprises an RNA polymerase binding site located 5' relative to and operably linked to a coding sequence encoding a polypeptide that confers increased tolerance to water deficit conditions in a transgenic plant compared to a control plant.

4. The plant cell of claim 1, wherein the water deficit-inducible promoter regulates expression of a polynucleotide encoding a polypeptide that confers increased tolerance to water deficit conditions.

5. The plant cell of claim 4, wherein the polypeptide is a transcription factor.

6. The plant cell of claim 5, wherein the transcription factor is selected from the group consisting of SEQ ID NOs:56, 58, 60, 62 and 64.

7. A transgenic plant comprising a recombinant polynucleotide comprising a nucleotide sequence and a promoter that has a water deficit-inducible promoter activity, wherein the promoter is operably linked to the nucleotide sequence to which it is not operably linked in nature,
   wherein said promoter has at least 98% identity to the sequence of SEQ ID NO: 6.

8. The transgenic plant of claim 7, wherein the recombinant polynucleotide is operably linked to a coding sequence encoding a polypeptide that confers increased tolerance to water deficit conditions in a transgenic plant compared to a control plant.

9. The transgenic plant of claim 7, wherein said recombinant polynucleotide is operably linked to and regulates a polynucleotide encoding a polypeptide that confers increased tolerance to water deficit conditions in a transgenic plant compared to a control plant.

10. The transgenic plant of claim 9, wherein the polypeptide is SEQ ID NO: 56.

11. The transgenic plant of claim 9, wherein the transgenic plant has greater tolerance to water deficit conditions than a control plant.

12. A transgenic seed produced by the transgenic plant of claim 7.

13. A transgenic plant comprising a recombinant polynucleotide comprising a nucleotide sequence and a promoter that has a water deficit-inducible promoter activity, wherein the promoter is operably linked to the nucleotide sequence to which it is not operably linked in nature, wherein said promoter has at least 98% identity to the polynucleotide sequence of SEQ ID NO: 6.

14. The transgenic plant of claim 13, wherein the recombinant polynucleotide is operably linked to and regulates a polynucleotide encoding a polypeptide that confers increased tolerance to water deficit conditions as compared to a control plant.

15. The transgenic plant of claim 13, wherein the recombinant polynucleotide comprises SEQ ID NO: 15.

16. The transgenic plant of claim 14, wherein the transgenic plant has greater tolerance to water deficit conditions than the control plant.

17. A transgenic seed produced by the transgenic plant of claim 13.

18. A transgenic plant comprising SEQ ID NO: 15.

19. The transgenic plant of claim 18, wherein the transgenic plant has greater tolerance to water-deficit conditions.

* * * * *